United States Patent
Priceman et al.

(10) Patent No.: US 12,129,286 B2
(45) Date of Patent: Oct. 29, 2024

(54) MEMBRANE-BOUND IL-12 FOR CELLULAR IMMUNOTHERAPY

(71) Applicant: CITY OF HOPE, Duarte, CA (US)

(72) Inventors: Saul J. Priceman, Valley Village, CA (US); John P. Murad, Diamond Bar, CA (US); Eric Lee, Diamond Bar, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 18/612,579

(22) Filed: Mar. 21, 2024

(65) Prior Publication Data

US 2024/0254183 A1 Aug. 1, 2024

Related U.S. Application Data

(63) Continuation of application No. PCT/US2023/064180, filed on Mar. 10, 2023.

(60) Provisional application No. 63/423,479, filed on Nov. 7, 2022, provisional application No. 63/318,753, filed on Mar. 10, 2022.

(51) Int. Cl.
 *C12N 15/24* (2006.01)
 *C07K 14/54* (2006.01)
 *C12N 5/0783* (2010.01)

(52) U.S. Cl.
 CPC ........ *C07K 14/5434* (2013.01); *C12N 5/0636* (2013.01); *C07K 2319/02* (2013.01)

(58) Field of Classification Search
 None
 See application file for complete search history.

(56) References Cited

U.S. PATENT DOCUMENTS

| | | | |
|---|---|---|---|
| 5,891,680 | A | 4/1999 | Lieschke et al. |
| 10,960,024 | B2 * | 3/2021 | Klingemann .. A61K 39/464412 |
| 11,421,010 | B2 * | 8/2022 | Li .................. A61K 39/464429 |
| 2019/0091310 | A1 | 3/2019 | Wright et al. |
| 2020/0048322 | A1 | 2/2020 | Li et al. |
| 2021/0145879 | A1 | 5/2021 | Lee et al. |
| 2021/0230547 | A1 | 7/2021 | Lee et al. |

FOREIGN PATENT DOCUMENTS

| | | |
|---|---|---|
| CN | 103230600 | 8/2013 |
| WO | WO 2016/048903 | 3/2016 |
| WO | WO 2017/015490 | 1/2017 |
| WO | WO 2017/062628 | 4/2017 |
| WO | WO 2017/079694 | 5/2017 |
| WO | WO 2017/192924 | 11/2017 |

(Continued)

OTHER PUBLICATIONS

Abate-Daga et al., "CAR models: next-generation CAR modifications for enhanced T-cell function," Mol Ther Oncolytics, May 2016, vol. 3, 16014, 7 pages.

(Continued)

*Primary Examiner* — Claire Kaufman
(74) *Attorney, Agent, or Firm* — Fish & Richardson P.C.

(57) ABSTRACT

This disclosure relates to, inter alia, cells expressing both a chimeric antigen receptor (CAR) and membrane bound IL-12 and the use of these cells to target and treat cancers (e.g., solid tumors and cancers expressing CD19, CD22, BCMA, PSCA, HER2, TAG-72, and PSCA). The disclosure also relates to cells expressing a membrane bound IL-12.

14 Claims, 32 Drawing Sheets

Specification includes a Sequence Listing.

(56) References Cited

FOREIGN PATENT DOCUMENTS

| WO | WO 2018/068008 | 4/2018 |
|---|---|---|
| WO | WO 2018/102761 | 6/2018 |
| WO | WO 2020/028656 | 2/2020 |
| WO | WO 2020/028721 | 2/2020 |
| WO | WO 2020/037206 | 2/2020 |
| WO | WO 2020/123716 | 6/2020 |
| WO | WO 2021/154218 | 8/2021 |
| WO | WO 2021/154263 | 8/2021 |
| WO | WO 2021/233317 | 11/2021 |
| WO | WO 2022/228492 | 11/2022 |

OTHER PUBLICATIONS

Adusumilli et al., "A phase I trial of regional mesothelin-targeted CAR T-cell therapy in patients with malignant pleural disease, in combination with the anti-PD-1 agent pembrolizumab," Cancer Discov, Nov. 2021, 11(11):2748-2763.
Adusumilli et al., "Regional delivery of mesothelin-targeted CAR T cell therapy generates potent and long-lasting CD4-dependent tumor immunity," Sci Transl Med, Nov. 2014, 6(261):1-14.
Agarwal et al., "Intratumourally injected alum-tethered cytokines elicit potent and safer local and systemic anticancer immunity," Nat Biomed Eng, Feb. 2022, 6(2):129-143 (19 pages including supplemental material).
Alizadeh et al., "IFNgamma is critical for CAR T cell-mediated myeloid activation and induction of endogenous immunity," Cancer Discov, Sep. 2021, 11(9):2248-2265.
Bell et al., "Engineered cytokine signaling to improve CAR T cell effector function," Front Immunol, Jun. 2021, vol. 12, Article 684642, 16 pages.
Bridgeman et al., "The optimal antigen response of chimeric antigen receptors harboring the CD3zeta transmembrane domain is dependent upon incorporation of the receptor into the endogenous TCR/CD3 complex," J Immunol, Jun. 2010, 184(12):6938-6949.
Brown et al., "Optimization of IL 13Ralpha2-targeted chimeric antigen receptor T cells for improved anti-tumor efficacy against glioblastoma," Mol Ther, Jan. 2018, 26(1): 31-44.
Brown et al., "Regression of glioblastoma after chimeric antigen receptor T-cell therapy," N Engl J Med, Dec. 2016, 375(26):2561-2569.
Ferrone et al., Adjuvanticity of plasmid DNA encoding cytokines fused to immunoglobulin Fc domains, Clin Cancer Res, Sep. 2006, 12(18):5511-5519.
Frigault et al., "State of the art in CAR T cell therapy for CD19+ B cell malignancies," J Clin Invest, Apr. 2020, 130(4):1586-1594.
Fujiwara et al., "Hinge and transmembrane domains of chimeric antigen receptor regulate receptor expression and signaling threshold," Cells, May 2020, 9(5), 1182, 17 pages.
Ge et al., "Oncolytic vaccinia virus delivering tethered IL-12 enhances antitumor effects with improved safety," J Immunother Cancer, Mar. 2020, 8(10):1-8.
GenBank Accession No. AAL77817.1, "single chain interleukin-12 [synthetic construct]," Mar. 11, 2010, 2 pages.
GenBank Accession No. J04132.1, "Human T cell receptor zeta-chain mRNA, complete cds," Jun. 23, 2010, 2 pages.
GenBank Accession No. M35160.1, "Human T4 surface glycoprotein CD4 gene, complete cds," Jun. 23, 2010, 2 pages.
GenBank Accession No. NC_000003.12, "*Homo sapiens* chromosome 3, GRCh38.p13 Primary Assembly," Mar. 1, 2021, 3 pages.
GenBank Accession No. NC_000005.10, "*Homo sapiens* chromosome 5, GRCh38.p13 Primary Assembly," Mar. 1, 2021, 3 pages.
GenBank Accession No. NM_001561.6, "*Homo sapiens* TNF receptor superfamily member 9 (TNFRSF9), mRNA," Feb. 21, 2021, 6 pages.
GenBank Accession No. NM_001768.7, "*Homo sapiens* CD8a molecule (CD8A), transcript variant 1, mRNA," Dec. 15, 2020, 4 pages.
GenBank Accession No. NM_003327.4, "*Homo sapiens* TNF receptor superfamily member 4 (TNFRSF4), mRNA," Feb. 15, 2021, 4 pages.
GenBank Accession No. NM_006139.4, "*Homo sapiens* CD28 molecule (CD28), transcript variant 1, mRNA," Feb. 16, 2021, 6 pages.
GenBank Accession No. NM_007360.4, "*Homo sapiens* killer cell lectin like receptor K1 (KLRK1), mRNA," Feb. 16, 2021, 4 pages.
GenBank Accession No. NM_016382.4, "*Homo sapiens* CD244 molecule (CD244), transcript variant 1, mRNA," Feb. 15, 2021, 6 pages.
Giordano-Attianese et al., "A computationally designed chimeric antigen receptor provides a small-molecule safety switch for T-cell therapy," Nat Biotechnol, Apr. 2020, 38(4):426-432 (14 pages including the supplemental material).
Guedan et al., "Engineering and design of chimeric antigen receptors," Mol Ther Methods Clin Dev, Dec. 2018, vol. 12, pp. 145-156.
Guedan et al., "Single residue in CD28-costimulated CAR-T cells limits long-term persistence and antitumor durability," J Clin Invest, Jun. 2020, 130(6):3087-3097.
Hege et al., "Safety, tumor trafficking and immunogenicity of chimeric antigen receptor (CAR)-T cells specific for TAG-72 in colorectal cancer," J Immunother Cancer, Mar. 2017, 5:22, 14 pages.
Heitzeneder et al., "GPC2-CAR T cells tuned for low antigen density mediate potent activity against neuroblastoma without toxicity," Cancer Cell, Jan. 2022, 40(10):53-69, e1-e9.
Henry et al., "IL-12 produced by dendritic cells augments CD8+ T cell activation through the production of the chemokines CCL 1 and CCL17," J Immunol, Dec. 2008, 181(12):8576-8584.
Hong et al., "Engineering CAR-T cells for next-generation cancer therapy," Cancer Cell, Oct. 2020, 38(4):473-488.
Hu et al., "Cell membrane-anchored and tumor-targeted IL-12 (attIL12)-T cell therapy for eliminating large and heterogeneous solid tumors," J Immunother Cancer, Jan. 2022, 10(1), e003633, pp. 1-15.
Huang et al., "Engineering light-controllable CAR T cells for cancer immunotherapy," Sci Adv, Feb. 2020, vol. 6, Issue 8, eaay9209, 13 pages.
Hurton et al., "Tethered IL-15 augments antitumor activity and promotes a stem-cell memory subset in tumor-specific T cells," Proc Natl Acad Sci U S A, Nov. 2016, 113(48):E7788-E7797.
International Search Report and Written Opinion in International Appln. No. PCT/US2023/064180, mailed on Jun. 1, 2023, 13 pages.
Jain et al., "Tumor interferon signaling and suppressive myeloid cells are associated with CAR T-cell failure in large B-cell lymphoma," Blood, May 2021, 137(19):2621-2633.
Jonnalagadda et al., "Chimeric antigen receptors with mutated IgG4 Fc spacer avoid fc receptor binding and improve T cell persistence and antitumor efficacy," Mol Ther, Apr. 2015, 23(4):757-768.
June et al., "Chimeric antigen receptor therapy," N Engl J Med, Jul. 2018, 379(1):64-73.
Kern et al., "Epression purification, and functional analysis of murine ectodomain fragments of CD8αα and CD8αl3 dimers," J Biol Chem, Sep. 1999, 274(38):27237-27243.
Kochenderfer et al., "Adoptive transfer of syngeneic T cells transduced with a chimeric antigen receptor that recognizes murine CD19 can eradicate lymphoma and normal B cells," Blood, Nov. 2010, 116(19):3875-3886.
Koneru et al., "IL-12 secreting tumor-targeted chimeric antigen receptor T cells eradicate ovarian tumors in vivo," Oncoimmunology, Jan. 2015, 24(3):e994446-1-11.
Kunkele et al., "Functional tuning of CARs reveals signaling threshold above which CD8+ CTL antitumor potency Is attenuated due to cell Fas-FasL-Dependent AICD," Cancer Immunol Res, Apr. 2015, 3(4):368-379.
Larson et al., "Recent advances and discoveries in the mechanisms and functions of CAR T cells," Nat Rev Cancer, Mar. 2021, 21(3):145-161.
Lee et al., "Preclinical optimization of a CD20-specific chimeric antigen receptor vector and culture conditions," J Immunother, Jan. 2018, 41(1):19-31, 13 pages.

(56) References Cited

OTHER PUBLICATIONS

Lieschke et al., "Bioactive murine and human interleukin-12 fusion proteins which retain antitumor activity in vivo," Nat Biotechnol, Jan. 1997, 15(1):35-40.
Lim et al., "The principles of engineering immune cells to treat cancer," Cell, Feb. 2017, 168(4):724-740.
Liu, X. et al. "Affinity-tuned ErbB2 or EGFR chimeric antigen receptor T cells exhibit an increased therapeutic index against tumors in mice," Cancer Res, Sep. 2015, 75(17):3596-3607.
Long et al., "4-1 BB costimulation ameliorates T cell exhaustion induced by tonic signaling of chimeric antigen receptors," Nat Med, Jun. 2015, 21(6):581-590 (13 pages including the supplemental material).
Luo et al., "Coexression of IL7 and CCL21 increases efficacy of CAR-T cells in solid tumors without requiring preconditioned lymphodepletion," Clin Cancer Res, Oct. 2020, 26(20):5494-5505.
Miller et al., "Enhanced intratumoural activity of CART cells engineered to produce immunomodulators under photothermal control," Nat Biomed Eng, Nov. 2021, 5(11):1348-1359.
Murad et al., "Effective targeting of TAG72(+) peritoneal ovarian tumors via regional delivery of CAR-engineered T cells," Front Immunol, Nov. 2018, vol. 9, Article 2268, pp. 1-13.
Murad et al., "Pre-conditioning modifies the TME to enhance solid tumor CAR T;cell efficacy and endogenous protective immunity," Mol Ther, Jul. 2021, 29(7):2335-2349.
Neman et al., "Human breast cancer metastases to the brain display GABAergic properties in the neural niche," Proc Natl Acad Sci U S A, Jan. 2014, 111(3):984-989.
Ogawa et al., "ST6GALNAC1 plays important roles in enhancing cancer stem phenotypes of colorectal cancer via the Akt pathway," Oncotarget, Nov. 2017, 8(68):112550-112564.
Pan et al., "Cancer immunotherapy using a membrane-bound interleukin-12 with B7-1 transmembrane and cytoplasmic domains," Mol Ther, May 2012, 20(5):927-937.
Park et al., "Effective combination immunotherapy using oncolytic viruses to deliver CAR targets to solid tumors," Sci Transl Med, Sep. 2020, 12(559), eaaz1863, 13 pages.
Peng et al., "A single-chain IL-12 IgG3 antibody fusion protein retains antibody specificity and IL-12 bioactivity and demonstrates antitumor activity," J Immunol, Jul. 1999, 163(1):250-258.
Priceman et al., "Co-stimulatory signaling determines tumor antigen sensitivity and persistence of CAR T cells targeting PSCA+ metastatic prostate cancer," Oncoimmunology, Oct. 2017, 7(2):e1380764-1-13.
Priceman et al., "Regional delivery of chimeric antigen receptor-engineered T cells effectively targets HER2(+) breast cancer metastasis to the brain," Clin Cancer Res, Jan. 2018, 24(1):95-105.
Priceman et al., "Smart CARs engineered for cancer immunotherapy," Curr Opin Oncol, Nov. 2015, 27(6):466-474.
Prinzing et al., "Hypoxia-inducible CAR expression: An answer to the on-target/off-tumor dilemma?" Cell Rep Med, Apr. 2021, vol. 2, Issue 4, 100244, 2 pages.
Rafiq et al. "Engineering strategies to overcome the current roadblocks in CAR T cell therapy," Nat Rev Clin Oncol, Mar. 2020, 17(3):147-167.
Roybal et al., "Precision tumor recognition by T cells with combinatorial antigen-sensing circuits, " Cell, Feb. 2016, 164(4):770-779.
Sadelain et al., "Therapeutic T cell engineering," Nature, May 2017, 545(7655):423-431.
Salter et al., "Phosphoproteomic analysis of chimeric antigen receptor signaling reveals kinetic and quantitative differences that affect cell function," Sci Signal, Aug. 2018, 11(544), eaat6753, 17 pages.
Schmidts et al., "Making CART cells a solid option for solid tumors," Front Immunol, Nov. 2018, vol. 9, Article 2593, pp. 1-10.
Siddiqi et al., "CD19-directed CAR T-cell therapy for treatment of primary CNS lymphoma," Blood Adv., Oct. 2021, 5(20):4059-4063.
Sridhar et al., "Regional delivery of chimeric antigen receptor (CAR) T-cells for cancer therapy," Cancers (Basel), Jul. 2017, 9(7), 92, 10 pages.
Srivastava et al., "Logic-gated ROR1 chimeric antigen receptor expression rescues T cell-mediated toxicity to normal tissues and enables selective tumor targeting," Cancer Cell, Mar. 2019, 35(3):489-503, e1-e8.
Sterner et al., "CAR-T cell therapy: current limitations and potential strategies," Blood Cancer J, Apr. 2021, 11(4), 69, 11 pages.
Tchou et al., "Safety and efficacy of intratumoral injections of chimeric antigen receptor (CAR) T cells in metastatic breast cancer," Cancer Immunol Res, Dec. 2017, 5(12):1152-1161.
Textor et al., "Efficacy of CAR T-cell therapy in large tumors relies upon stromal targeting by IFNgamma," Cancer Res, Dec. 2014, 74(23):6796-6805.
Van der Stegen et al., "The pharmacology of second generation chimeric antigen receptors," Nat Rev Drug Discov, Jul. 2015, 14(7):499-509.
Wang et al., "The cerebroventricular environment modifies CART cells for potent activity against both central nervous system and systemic lymphoma," Cancer Immunol Res, Jan. 2021, 9(1): 75-88.
Wiesinger et al., "Clinical-Scale Production of CAR-T Cells for the Treatment of Melanoma Patients by mRNA Transfection of a CSPG4-Specific CAR under Full GMP Compliance," Cancers (Basel), Aug. 2019, 11(8), 1198, 18 pages.
Yeku et al., "Armored CART cells enhance antitumor efficacy and overcome the tumor microenvironment," Sci Rep, Sep. 2017, 7(1):1-14.
Yoon et al., "Construction, affinity maturation, and biological characterization of an anti-tumor-associated glycoprotein-72 humanized antibody," J Biol Chem, Mar. 2006, 281(11):6985-6992.
Yu et al., "Next generation chimeric antigen receptor T cells: safety strategies to overcome toxicity," Mol Cancer, Aug. 2019, 18(1), 125, 13 pages.
Zhang et al., "Enhanced efficacy and limited systemic cytokine exposure with membrane-anchored interleukin-12 T-cell therapy in murine tumor models," J Immunother Cancer, Jan. 2020, 8(1):e000210, pp. 1-12.
Zhang et al., "Improving adoptive T cell therapy by targeting and controlling IL-12 expression to the tumor environment," Mol Ther, Apr. 2011, 19(4):751-759.
Zhang et al., "Tumor-infiltrating lymphocytes genetically engineered with an inducible gene encoding interleukin-12 for the immunotherapy of metastatic melanoma," Clin Cancer Res, May 2015, 21(10):2278-2288.
Zhao et al., "Structural design of engineered costimulation determines tumor rejection kinetics and persistence of CAR T cells," Cancer Cell, Oct. 2015, 28(4):415-428.

* cited by examiner

SEQUENCE LISTING

```
Sequence total quantity: 89
SEQ ID NO: 1            moltype = AA  length = 306
FEATURE                 Location/Qualifiers
source                  1..306
                        mol_type = protein
                        organism = Homo sapiens
SEQUENCE: 1
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                            306

SEQ ID NO: 2            moltype = AA  length = 198
FEATURE                 Location/Qualifiers
source                  1..198
                        mol_type = protein
```

```
                             organism = Homo sapiens
SEQUENCE: 2
ARNLPVATPD PGMFPCLHHS QNLLRAVSNM LQKARQTLEF YPCTSEEIDH EDITKDKTST    60
VEACLPLELT KNESCLNSRE TSFITNGSCL ASRKTSFMMA LCLSSIYEDS KMYQVEFKTM   120
NAKLLMDPKR QIFLDQNMLA VIDELMQALN FNSETVPQKS SLEEPDFYKT KIKLCILLHA   180
FRIRAVTIDR VMSYLNAS                                                 198

SEQ ID NO: 3                 moltype = AA  length = 198
FEATURE                      Location/Qualifiers
source                       1..198
                             mol_type = protein
                             organism = Homo sapiens
SEQUENCE: 3
ARNLPVATPD PGMFPCLHHS QNLLRAVSNM LQKARQTLEF YPCTSEEIDH EDITKDKTST    60
VEACLPLELT KNESCLNSRE TSFITNGSCL ASRKTSFMMA LCLSSIYEDL KMYQVEFKTM   120
NAKLLMDPKR QIFLDQNMLA VIDELMQALN FNSETVPQKS SLEEPDFYKT KIKLCILLHA   180
FRIRAVTIDR VMSYLNAS                                                 198

SEQ ID NO: 4                 moltype = AA  length = 10
FEATURE                      Location/Qualifiers
source                       1..10
                             mol_type = protein
                             organism = synthetic construct
SEQUENCE: 4
VPGVGVPGVG                                                           10

SEQ ID NO: 5                 moltype = AA  length = 4
FEATURE                      Location/Qualifiers
source                       1..4
                             mol_type = protein
                             organism = Homo sapiens
SEQUENCE: 5
RSKR                                                                  4

SEQ ID NO: 6                 moltype = AA  length = 548
FEATURE                      Location/Qualifiers
source                       1..548
                             mol_type = protein
                             organism = synthetic construct
SEQUENCE: 6
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSVPGV GVPGVGARNL PVATPDPGMF PCLHHSQNLL RAVSNMLQKA RQTLEFYPCT   360
SEEIDHEDIT KDKTSTVEAC LPLELTKNES CLNSRETSFI TNGSCLASRK TSFMMALCLS   420
SIYEDSKMYQ VEFKTMNAKL LMDPKRQIFL DQNMLAVIDE LMQALNFNSE TVPQKSSLEE   480
PDFYKTKIKL CILLHAFRIR AVTIDRVMSY LNASGGGFWV LVVVGGVLAC YSLLVTVAFI   540
IFWVRSKR                                                            548

SEQ ID NO: 7                 moltype = AA  length = 548
FEATURE                      Location/Qualifiers
source                       1..548
                             mol_type = protein
                             organism = synthetic construct
SEQUENCE: 7
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSVPGV GVPGVGARNL PVATPDPGMF PCLHHSQNLL RAVSNMLQKA RQTLEFYPCT   360
SEEIDHEDIT KDKTSTVEAC LPLELTKNES CLNSRETSFI TNGSCLASRK TSFMMALCLS   420
SIYEDLKMYQ VEFKTMNAKL LMDPKRQIFL DQNMLAVIDE LMQALNFNSE TVPQKSSLEE   480
PDFYKTKIKL CILLHAFRIR AVTIDRVMSY LNASGGGFWV LVVVGGVLAC YSLLVTVAFI   540
IFWVRSKR                                                            548

SEQ ID NO: 8                 moltype = AA  length = 570
FEATURE                      Location/Qualifiers
source                       1..570
                             mol_type = protein
                             organism = synthetic construct
SEQUENCE: 8
MCHQQLVISW FSLVFLASPL VAIWELKKDV YVVELDWYPD APGEMVVLTC DTPEEDGITW    60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
```

```
RKNASISVRA QDRYYSSSWS EWASVPCSVP GVGVPGVGAR NLPVATPDPG MFPCLHHSQN    360
LLRAVSNMLQ KARQTLEFYP CTSEEIDHED ITKDKTSTVE ACLPLELTKN ESCLNSRETS    420
FITNGSCLAS RKTSFMMALC LSSIYEDSKM YQVEFKTMNA KLLMDPKRQI FLDQNMLAVI    480
DELMQALNFN SETVPQKSSL EEPDFYKTKI KLCILLHAFR IRAVTIDRVM SYLNASGGGF    540
WVLVVVGGVL ACYSLLVTVA FIIFWVRSKR                                     570

SEQ ID NO: 9            moltype = AA   length = 570
FEATURE                 Location/Qualifiers
source                  1..570
                        mol_type = protein
                        organism = synthetic construct
SEQUENCE: 9
MCHQQLVISW FSLVFLASPL VAIWELKKDV YVVELDWYPD APGEMVVLTC DTPEEDGITW     60
TLDQSSEVLG SGKTLTIQVK EFGDAGQYTC HKGGEVLSHS LLLLHKKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYYSSSWS EWASVPCSVP GVGVPGVGAR NLPVATPDPG MFPCLHHSQN    360
LLRAVSNMLQ KARQTLEFYP CTSEEIDHED ITKDKTSTVE ACLPLELTKN ESCLNSRETS    420
FITNGSCLAS RKTSFMMALC LSSIYEDLKM YQVEFKTMNA KLLMDPKRQI FLDQNMLAVI    480
DELMQALNFN SETVPQKSSL EEPDFYKTKI KLCILLHAFR IRAVTIDRVM SYLNASGGGF    540
WVLVVVGGVL ACYSLLVTVA FIIFWVRSKR                                     570

SEQ ID NO: 10           moltype = AA   length = 22
FEATURE                 Location/Qualifiers
source                  1..22
                        mol_type = protein
                        organism = synthetic construct
SEQUENCE: 10
MCHQQLVISW FSLVFLASPL VA                                              22

SEQ ID NO: 11           moltype = AA   length = 22
FEATURE                 Location/Qualifiers
source                  1..22
                        mol_type = protein
                        organism = synthetic construct
SEQUENCE: 11
MLLLVTSLLL CELPHPAFLL IP                                              22

SEQ ID NO: 12           moltype = AA   length = 17
FEATURE                 Location/Qualifiers
source                  1..17
                        mol_type = protein
                        organism = synthetic construct
SEQUENCE: 12
SSGGGGSGGG GSGGGGS                                                    17

SEQ ID NO: 13           moltype = AA   length = 4
FEATURE                 Location/Qualifiers
source                  1..4
                        mol_type = protein
                        organism = synthetic construct
SEQUENCE: 13
GGGS                                                                   4

SEQ ID NO: 14           moltype = AA   length = 5
FEATURE                 Location/Qualifiers
source                  1..5
                        mol_type = protein
                        organism = synthetic construct
SEQUENCE: 14
GGGGS                                                                  5

SEQ ID NO: 15           moltype = AA   length = 21
FEATURE                 Location/Qualifiers
source                  1..21
                        mol_type = protein
                        organism = Homo sapiens
SEQUENCE: 15
LCYLLDGILF IYGVILTALF L                                               21

SEQ ID NO: 16           moltype = AA   length = 27
FEATURE                 Location/Qualifiers
source                  1..27
                        mol_type = protein
                        organism = Homo sapiens
SEQUENCE: 16
FWVLVVVGGV LACYSLLVTV AFIIFWV                                         27
```

```
-continued

SEQ ID NO: 17            moltype = AA  length = 28
FEATURE                  Location/Qualifiers
source                   1..28
                         mol_type = protein
                         organism = Homo sapiens
SEQUENCE: 17
MFWVLVVVGG VLACYSLLVT VAFIIFWV                                        28

SEQ ID NO: 18            moltype = AA  length = 22
FEATURE                  Location/Qualifiers
source                   1..22
                         mol_type = protein
                         organism = Homo sapiens
SEQUENCE: 18
MALIVLGGVA GLLLFIGLGI FF                                              22

SEQ ID NO: 19            moltype = AA  length = 21
FEATURE                  Location/Qualifiers
source                   1..21
                         mol_type = protein
                         organism = Homo sapiens
SEQUENCE: 19
IYIWAPLAGT CGVLLLSLVI T                                               21

SEQ ID NO: 20            moltype = AA  length = 23
FEATURE                  Location/Qualifiers
source                   1..23
                         mol_type = protein
                         organism = Homo sapiens
SEQUENCE: 20
IYIWAPLAGT CGVLLLSLVI TLY                                             23

SEQ ID NO: 21            moltype = AA  length = 24
FEATURE                  Location/Qualifiers
source                   1..24
                         mol_type = protein
                         organism = Homo sapiens
SEQUENCE: 21
IYIWAPLAGT CGVLLLSLVI TLYC                                            24

SEQ ID NO: 22            moltype = AA  length = 27
FEATURE                  Location/Qualifiers
source                   1..27
                         mol_type = protein
                         organism = Homo sapiens
SEQUENCE: 22
IISFFLALTS TALLFLLFFL TLRFSVV                                         27

SEQ ID NO: 23            moltype = AA  length = 21
FEATURE                  Location/Qualifiers
source                   1..21
                         mol_type = protein
                         organism = Homo sapiens
SEQUENCE: 23
PFFFCCFIAV AMGIRFIIMV A                                               21

SEQ ID NO: 24            moltype = AA  length = 10
FEATURE                  Location/Qualifiers
source                   1..10
                         mol_type = protein
                         organism = synthetic construct
SEQUENCE: 24
GGGSSGGGSG                                                            10

SEQ ID NO: 25            moltype = AA  length = 12
FEATURE                  Location/Qualifiers
source                   1..12
                         mol_type = protein
                         organism = synthetic construct
SEQUENCE: 25
ESKYGPPCPP CP                                                         12

SEQ ID NO: 26            moltype = AA  length = 12
FEATURE                  Location/Qualifiers
source                   1..12
                         mol_type = protein
                         organism = synthetic construct
SEQUENCE: 26
ESKYGPPCPS CP                                                         12
```

```
SEQ ID NO: 27              moltype = AA   length = 22
FEATURE                    Location/Qualifiers
source                     1..22
                           mol_type = protein
                           organism = synthetic construct
SEQUENCE: 27
ESKYGPPCPP CPGGGSSGGG SG                                              22

SEQ ID NO: 28              moltype = AA   length = 39
FEATURE                    Location/Qualifiers
source                     1..39
                           mol_type = protein
                           organism = synthetic construct
SEQUENCE: 28
IEVMYPPPYL DNEKSNGTII HVKGKHLCPS PLFPGPSKP                             39

SEQ ID NO: 29              moltype = AA   length = 48
FEATURE                    Location/Qualifiers
source                     1..48
                           mol_type = protein
                           organism = synthetic construct
SEQUENCE: 29
AKPTTTPAPR PPTPAPTIAS QPLSLRPEAC RPAAGGAVHT RGLDFACD                   48

SEQ ID NO: 30              moltype = AA   length = 45
FEATURE                    Location/Qualifiers
source                     1..45
                           mol_type = protein
                           organism = synthetic construct
SEQUENCE: 30
TTTPAPRPPT PAPTIASQPL SLRPEACRPA AGGAVHTRGL DFACD                      45

SEQ ID NO: 31              moltype = AA   length = 129
FEATURE                    Location/Qualifiers
source                     1..129
                           mol_type = protein
                           organism = synthetic construct
SEQUENCE: 31
ESKYGPPCPP CPGGGSSGGG SGGQPREPQV YTLPPSQEEM TKNQVSLTCL VKGFYPSDIA      60
VEWESNGQPE NNYKTTPPVL DSDGSFFLYS RLTVDKSRWQ EGNVFSCSVM HEALHNHYTQ     120
KSLSLSLGK                                                            129

SEQ ID NO: 32              moltype = AA   length = 229
FEATURE                    Location/Qualifiers
source                     1..229
                           mol_type = protein
                           organism = synthetic construct
SEQUENCE: 32
ESKYGPPCPS CPAPEFEGGP SVFLFPPKPK DTLMISRTPE VTCVVVDVSQ EDPEVQFNWY      60
VDGVEVHNAK TKPREEQFQS TYRVVSVLTV LHQDWLNGKE YKCKVSNKGL PSSIEKTISK     120
AKGQPREPQV YTLPPSQEEM TKNQVSLTCL VKGFYPSDIA VEWESNGQPE NNYKTTPPVL     180
DSDGSFFLYS RLTVDKSRWQ EGNVFSCSVM HEALHNHYTQ KSLSLSLGK                 229

SEQ ID NO: 33              moltype = AA   length = 229
FEATURE                    Location/Qualifiers
source                     1..229
                           mol_type = protein
                           organism = synthetic construct
SEQUENCE: 33
ESKYGPPCPP CPAPEFEGGP SVFLFPPKPK DTLMISRTPE VTCVVVDVSQ EDPEVQFNWY      60
VDGVEVHNAK TKPREEQFQS TYRVVSVLTV LHQDWLNGKE YKCKVSNKGL PSSIEKTISK     120
AKGQPREPQV YTLPPSQEEM TKNQVSLTCL VKGFYPSDIA VEWESNGQPE NNYKTTPPVL     180
DSDGSFFLYS RLTVDKSRWQ EGNVFSCSVM HEALHNHYTQ KSLSLSLGK                 229

SEQ ID NO: 34              moltype = AA   length = 107
FEATURE                    Location/Qualifiers
source                     1..107
                           mol_type = protein
                           organism = synthetic construct
SEQUENCE: 34
GQPREPQVYT LPPSQEEMTK NQVSLTCLVK GFYPSDIAVE WESNGQPENN YKTTPPVLDS      60
DGSFFLYSRL TVDKSRWQEG NVFSCSVMHE ALHNHYTQKS LSLSLGK                   107

SEQ ID NO: 35              moltype = AA   length = 112
FEATURE                    Location/Qualifiers
source                     1..112
                           mol_type = protein
                           organism = Homo sapiens
```

```
SEQUENCE: 35
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 36           moltype = AA  length = 41
FEATURE                 Location/Qualifiers
source                  1..41
                        mol_type = protein
                        organism = Homo sapiens
SEQUENCE: 36
RSKRSRLLHS DYMNMTPRRP GPTRKHYQPY APPRDFAAYR S                       41

SEQ ID NO: 37           moltype = AA  length = 41
FEATURE                 Location/Qualifiers
source                  1..41
                        mol_type = protein
                        organism = Homo sapiens
SEQUENCE: 37
RSKRSRGGHS DYMNMTPRRP GPTRKHYQPY APPRDFAAYR S                       41

SEQ ID NO: 38           moltype = AA  length = 42
FEATURE                 Location/Qualifiers
source                  1..42
                        mol_type = protein
                        organism = Homo sapiens
SEQUENCE: 38
KRGRKKLLYI FKQPFMRPVQ TTQEEDGCSC RFPEEEEGGC EL                      42

SEQ ID NO: 39           moltype = AA  length = 42
FEATURE                 Location/Qualifiers
source                  1..42
                        mol_type = protein
                        organism = Homo sapiens
SEQUENCE: 39
ALYLLRRDQR LPPDAHKPPG GGSFRTPIQE EQADAHSTLA KI                      42

SEQ ID NO: 40           moltype = AA  length = 120
FEATURE                 Location/Qualifiers
source                  1..120
                        mol_type = protein
                        organism = Homo sapiens
SEQUENCE: 40
WRRKRKEKQS ETSPKEFLTI YEDVKDLKTR RNHEQEQTFP GGGSTIYSMI QSQSSAPTSQ    60
EPAYTLYSLI QPSRKSGSRK RNHSPSFNST IYEVIGKSQP KAQNPARLSR KELENFDVYS   120

SEQ ID NO: 41           moltype =     length =
SEQUENCE: 41
000

SEQ ID NO: 42           moltype =     length =
SEQUENCE: 42
000

SEQ ID NO: 43           moltype =     length =
SEQUENCE: 43
000

SEQ ID NO: 44           moltype = AA  length = 570
FEATURE                 Location/Qualifiers
source                  1..570
                        mol_type = protein
                        organism = synthetic construct
SEQUENCE: 44
MLLLVTSLLL CELPHPAFLL IPIWELKKDV YVVELDWYPD APGEMVVLTC DTPEEDGITW    60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCSVP GVGVPGVGAR NLPVATPDPG MFPCLHHSQN   360
LLRAVSNMLQ KARQTLEFYP CTSEEIDHED ITKDKTSTVE ACLPLELTKN ESCLNSRETS   420
FITNGSCLAS RKTSFMMALC LSSIYEDSKM YQVEFKTMNA KLLMDPKRQI FLDQNMLAVI   480
DELMQALNFN SETVPQKSSL EEPDFYKTKI KLCILLHAFR IRAVTIDRVM SYLNASGGGF   540
WVLVVVGGVL ACYSLLVTVA FIIFWVRSKR                                   570

SEQ ID NO: 45           moltype = AA  length = 24
FEATURE                 Location/Qualifiers
source                  1..24
                        mol_type = protein
                        organism = synthetic construct
```

```
SEQUENCE: 45
LEGGGEGRGS LLTCGDVEEN PGPR                                              24

SEQ ID NO: 46           moltype = AA   length = 354
FEATURE                 Location/Qualifiers
source                  1..354
                        mol_type = protein
                        organism = synthetic construct
SEQUENCE: 46
LVTSLLLCEL PHPAFLLIPR KVCNGIGIGE FKDSLSINAT NIKHFKNCTS ISGDLHILPV        60
AFRGDSFTHT PPLDPQELDI LKTVKEITGF LLIQAWPENR TDLHAFENLE IIRGRTKQHG       120
QFSLAVVSLN ITSLGLRSLK EISDGDVIIS GNKNLCYANT INWKKLFGTS GQKTKIISNR       180
GENSCKATGQ VCHALCSPEG CWGPEPRDCV SCRNVSRGRE CVDKCNLLEG EPREFVENSE       240
CIQCHPECLP QAMNITCTGR GPDNCIQCAH YIDGPHCVKT CPAGVMGENN TLVWKYADAG       300
HVCHLCHPNC TYGCTGPGLE GCPTNGPKIP SIATGMVGAL LLLLVVALGI GLFM             354

SEQ ID NO: 47           moltype = AA   length = 323
FEATURE                 Location/Qualifiers
source                  1..323
                        mol_type = protein
                        organism = synthetic construct
SEQUENCE: 47
MPPPRLLFFL LFLTPMEVRP EEPLVVKVEE GDNAVLQCLK GTSDGPTQQL TWSRESPLKP        60
FLKLSLGLPG LGIHMRPLAI WLFIFNVSQQ MGGFYLCQPG PPSEKAWQPG WTVNVEGSGE       120
LFRWNVSDLG GLGCGLKNRS SEGPSSPSGK LMSPKLYVWA KDRPEIWEGE PPCVPPRDSL       180
NQSLSQPDLTM APGSTLWLSC GVPPDSVSRG PLSWTHVHPK GPKSLLSLEL KDDRPARDMW      240
VMETGLLLPR ATAQDAGKYY CHRGNLTMSF HLEITARPVL WHWLLRTGGW KVSAVTLAYL      300
IFCLCSLVGI LHLQRALVLR RKR                                              323

SEQ ID NO: 48           moltype = AA   length = 569
FEATURE                 Location/Qualifiers
source                  1..569
                        mol_type = protein
                        organism = synthetic construct
SEQUENCE: 48
MLLLVTSLLL CELPHPAFLL IPIWELKKDV YVVELDWYPD APGEMVVLTC DTPEEDGITW        60
TLDQSSEVLG SGKTLTIQVK EFGDAGQYTC HKGGEVLSHS LLLLHKKEDG IWSTDILKDQ      120
KEPKNKTFLR CEAKNYSGRF TCWWLTTIST DLTFSVKSSR GSSDPQGVTC GAATLSAERV      180
RGDNKEYEYS VECQEDSACP AAEESLPIEV MVDAVHKLKY ENYTSSFFIR DIIKPDPPKN      240
LQLKPLKNSR VEVSWEYPDT WSTPHSYFSL TFCVQVQGKS KREKKDRVFT DKTSATVICR      300
KNASISVRAQ DRYYSSSWSE WASVPCSVPG VGVPGVGARN LPVATPDPGM FPCLHHSQNL      360
LRAVSNMLQK ARQTLEFYPC TSEEIDHEDI TKDKTSTVEA CLPLELTKNE SCLNSRETSF      420
ITNGSCLASR KTSFMMALCL SSIYEDSKMY QVEFKTMNAK LLMDPKRQIF LDQNMLAVID      480
ELMQALNFNS ETVPQKSSLE EPDFYKTKIK LCILLHAFRI RAVTIDRVMS YLNASGGGFW      540
VLVVVGGVLA CYSLLVTVAF IIFWVRSKR                                        569

SEQ ID NO: 49           moltype = AA   length = 570
FEATURE                 Location/Qualifiers
source                  1..570
                        mol_type = protein
                        organism = synthetic construct
SEQUENCE: 49
MLLLVTSLLL CELPHPAFLL IPIWELKKDV YVVELDWYPD APGEMVVLTC DTPEEDGITW        60
TLDQSSEVLG SGKTLTIQVK EFGDAGQYTC HKGGEVLSHS LLLLHKKEDG IWSTDILKDQ      120
KEPKNKTFLR CEAKNYSGRF TCWWLTTIST DLTFSVKSSR GSSDPQGVTC GAATLSAERV      180
RGDNKEYEYS VECQEDSACP AAEESLPIEV MVDAVHKLKY ENYTSSFFIR DIIKPDPPKN      240
LQLKPLKNSR QVEVSWEYPD TWSTPHSYFS LTFCVQVQGK SKREKKDRVF TDKTSATVIC      300
RKNASISVRA QDRYYSSSWS EWASVPCSVP GVGVPGVGAR NLPVATPDPG MFPCLHHSQN      360
LLRAVSNMLQ KARQTLEFYP CTSEEIDHED ITKDKTSTVE ACLPLELTKN ESCLNSRETS      420
FITNGSCLAS RKTSFMMALC LSSIYEDLKM YQVEFKTMNA KLLMDPKRQI FLDQNMLAVI      480
DELMQALNFN SETVPQKSSL EEPDFYKTKI KLCILLHAFR IRAVTIDRVM SYLNASGGGF      540
WVLVVVGGVL ACYSLLVTVA FIIFWVRSKR                                       570

SEQ ID NO: 50           moltype = AA   length = 112
FEATURE                 Location/Qualifiers
source                  1..112
                        mol_type = protein
                        organism = synthetic construct
SEQUENCE: 50
RVKFSRSADA PAYQQGQNQL YNELNLGRRE EYDVLDKRRG RDPEMGGKPR RKNPQEGLFN        60
ELQKDKMAEA FSEIGMKGER RRGKGHDGLF QGLSTATKDT FDALHMQALP PR              112

SEQ ID NO: 51           moltype = AA   length = 112
FEATURE                 Location/Qualifiers
source                  1..112
                        mol_type = protein
                        organism = synthetic construct
SEQUENCE: 51
RVKFSRSADA PAYQQGQNQL YNELNLGRRE EYDVLDKRRG RDPEMGGKPR RKNPQEGLFN        60
```

```
ELQKDKMAEA FSEIGMKGER RRGKGHDGLY QGLSTATKDT YDALHMQALP PR            112

SEQ ID NO: 52           moltype = AA   length = 112
FEATURE                 Location/Qualifiers
source                  1..112
                        mol_type = protein
                        organism = synthetic construct
SEQUENCE: 52
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLF QGLSTATKDT FDALHMQALP PR            112

SEQ ID NO: 53           moltype = AA   length = 112
FEATURE                 Location/Qualifiers
source                  1..112
                        mol_type = protein
                        organism = synthetic construct
SEQUENCE: 53
RVKFSRSADA PAYQQGQNQL YNELNLGRRE EYDVLDKRRG RDPEMGGKPR RKNPQEGLYN    60
ELQKDKMAEA FSEIGMKGER RRGKGHDGLF QGLSTATKDT FDALHMQALP PR            112

SEQ ID NO: 54           moltype = AA   length = 112
FEATURE                 Location/Qualifiers
source                  1..112
                        mol_type = protein
                        organism = synthetic construct
SEQUENCE: 54
RVKFSRSADA PAYQQGQNQL YNELNLGRRE EYDVLDKRRG RDPEMGGKPR RKNPQEGLFN    60
ELQKDKMAEA YSEIGMKGER RRGKGHDGLF QGLSTATKDT FDALHMQALP PR            112

SEQ ID NO: 55           moltype = AA   length = 112
FEATURE                 Location/Qualifiers
source                  1..112
                        mol_type = protein
                        organism = synthetic construct
SEQUENCE: 55
RVKFSRSADA PAYQQGQNQL YNELNLGRRE EYDVLDKRRG RDPEMGGKPR RKNPQEGLFN    60
ELQKDKMAEA FSEIGMKGER RRGKGHDGLY QGLSTATKDT FDALHMQALP PR            112

SEQ ID NO: 56           moltype = AA   length = 112
FEATURE                 Location/Qualifiers
source                  1..112
                        mol_type = protein
                        organism = synthetic construct
SEQUENCE: 56
RVKFSRSADA PAYQQGQNQL YNELNLGRRE EYDVLDKRRG RDPEMGGKPR RKNPQEGLFN    60
ELQKDKMAEA FSEIGMKGER RRGKGHDGLF QGLSTATKDT YDALHMQALP PR            112

SEQ ID NO: 57           moltype = AA   length = 20
FEATURE                 Location/Qualifiers
source                  1..20
                        mol_type = protein
                        organism = synthetic construct
SEQUENCE: 57
GGGGSGGGGS GGGGSGGGGS                                                20

SEQ ID NO: 58           moltype = AA   length = 4
FEATURE                 Location/Qualifiers
source                  1..4
                        mol_type = protein
                        organism = synthetic construct
SEQUENCE: 58
GGGG                                                                 4

SEQ ID NO: 59           moltype = AA   length = 6
FEATURE                 Location/Qualifiers
source                  1..6
                        mol_type = protein
                        organism = synthetic construct
SEQUENCE: 59
GGGSGG                                                               6

SEQ ID NO: 60           moltype = AA   length = 8
FEATURE                 Location/Qualifiers
source                  1..8
                        mol_type = protein
                        organism = synthetic construct
SEQUENCE: 60
GGGSGGGS                                                             8
```

```
SEQ ID NO: 61             moltype = AA   length = 560
FEATURE                   Location/Qualifiers
source                    1..560
                          mol_type = protein
                          organism = synthetic construct
SEQUENCE: 61
QVQLVQSGAE VVKPGASVKI SCKASGYTFT DHAIHWVKQN PGQRLEWIGY FSPGNDDFKY    60
SQKFQGKATL TADTSASTAY VELSSLRSED TAVYFCTRSL NMAYWGQGTL VTVSSGSTSG   120
GGSGGGSGGG GSSDIVMSQS PDSLAVSLGE RVTLNCKSSQ SVLYSSNSKN YLAWYQQKPG   180
QSPKLLIYWA STRESGVPDR FSGSGSGTDF TLTISSVQAE DVAVYYCQQY YSYPLSFGAG   240
TKLELKESKY GPPCPPCPGG GSSGGGSGGQ PREPQVYTLP PSQEEMTKNQ VSLTCLVKGF   300
YPSDIAVEWE SNGQPENNYK TTPPVLDSDG SFFLYSRLTV DKSRWQEGNV FSCSVMHEAL   360
HNHYTQKSLS LSLGKMFWVL VVVGGVLACY SLLVTVAFII FWVKRGRKKL LYIFKQPFMR   420
PVQTTQEEDG CSCRFPEEEE GGCELGGGRV KFSRSADAPA YQQGQNQLYN ELNLGRREEY   480
DVLDKRRGRD PEMGGKPRRK NPQEGLYNEL QKDKMAEAYS EIGMKGERRR GKGHDGLYQG   540
LSTATKDTYD ALHMQALPPR                                              560

SEQ ID NO: 62             moltype = AA   length = 582
FEATURE                   Location/Qualifiers
source                    1..582
                          mol_type = protein
                          organism = synthetic construct
SEQUENCE: 62
MLLLVTSLLL CELPHPAFLL IPQVQLVQSG AEVVKPGASV KISCKASGYT FTDHAIHWVK    60
QNPGQRLEWI GYFSPGNDDF KYSQKFQGKA TLTADTSAST AYVELSSLRS EDTAVYFCTR   120
SLNMAYWGQG TLVTVSSGST SGGGSGGGSG GGGSSDIVMS QSPDSLAVSL GERVTLNCKS   180
SQSVLYSSNS KNYLAWYQQK PGQSPKLLIY WASTRESGVP DRFSGSGSGT DFTLTISSVQ   240
AEDVAVYYCQ QYYSYPLSFG AGTKLELKES KYGPPCPPCP GGGSSGGGSG GQPREPQVYT   300
LPPSQEEMTK NQVSLTCLVK GFYPSDIAVE WESNGQPENN YKTTPPVLDS DGSFFLYSRL   360
TVDKSRWQEG NVFSCSVMHE ALHNYTQKS LSLSLGKMFW VLVVVGGVLA CYSLLVTVAF   420
IIFWVKRGRK KLLYIFKQPF MRPVQTTQEE DGCSCRFPEE EEGGCELGGG RVKFSRSADA   480
PAYQQGQNQL YNELNLGRRE EYDVLDKRRG RDPEMGGKPR RKNPQEGLYN ELQKDKMAEA   540
YSEIGMKGER RRGKGHDGLY QGLSTATKDT YDALHMQALP PR                     582

SEQ ID NO: 63             moltype = AA   length = 115
FEATURE                   Location/Qualifiers
source                    1..115
                          mol_type = protein
                          organism = synthetic construct
SEQUENCE: 63
QVQLVQSGAE VVKPGASVKI SCKASGYTFT DHAIHWVKQN PGQRLEWIGY FSPGNDDFKY    60
SQKFQGKATL TADTSASTAY VELSSLRSED TAVYFCTRSL NMAYWGQGTL VTVSS        115

SEQ ID NO: 64             moltype = AA   length = 5
FEATURE                   Location/Qualifiers
source                    1..5
                          mol_type = protein
                          organism = synthetic construct
SEQUENCE: 64
DHAIH                                                                5

SEQ ID NO: 65             moltype = AA   length = 17
FEATURE                   Location/Qualifiers
source                    1..17
                          mol_type = protein
                          organism = synthetic construct
SEQUENCE: 65
YFSPGNDDFK YSQKFQG                                                  17

SEQ ID NO: 66             moltype = AA   length = 6
FEATURE                   Location/Qualifiers
source                    1..6
                          mol_type = protein
                          organism = synthetic construct
SEQUENCE: 66
SLNMAY                                                               6

SEQ ID NO: 67             moltype = AA   length = 113
FEATURE                   Location/Qualifiers
source                    1..113
                          mol_type = protein
                          organism = synthetic construct
SEQUENCE: 67
DIVMSQSPDS LAVSLGERVT LNCKSSQSVL YSSNSKNYLA WYQQKPGQSP KLLIYWASTR    60
ESGVPDRFSG SGSGTDFTLT ISSVQAEDVA VYYCQQYYSY PLSFGAGTKL ELK          113

SEQ ID NO: 68             moltype = AA   length = 17
FEATURE                   Location/Qualifiers
source                    1..17
```

```
                         mol_type = protein
                         organism = synthetic construct
SEQUENCE: 68
KSSQSVLYSS NSKNYLA                                                          17

SEQ ID NO: 69            moltype = AA   length = 7
FEATURE                  Location/Qualifiers
source                   1..7
                         mol_type = protein
                         organism = synthetic construct
SEQUENCE: 69
WASTRES                                                                      7

SEQ ID NO: 70            moltype = AA   length = 9
FEATURE                  Location/Qualifiers
source                   1..9
                         mol_type = protein
                         organism = synthetic construct
SEQUENCE: 70
QQYYSYPLS                                                                    9

SEQ ID NO: 71            moltype = AA   length = 348
FEATURE                  Location/Qualifiers
source                   1..348
                         mol_type = protein
                         organism = synthetic construct
SEQUENCE: 71
LEGGGEGRGS LLTCGDVEEN PGPTRMPPPR LLFFLLFLTP MEVRPEEPLV VKVEEGDNAV            60
LQCLKGTSDG PTQQLTWSRE SPLKPFLKLS LGLPGLGIHM RPLAIWLFIF NVSQQMGGFY           120
LCQPGPPSEK AWQPGWTVNV EGSGELFRWN VSDLGGLGCG LKNRSSEGPS SPSGKLMSPK           180
LYVVWAKDRPE IWEGEPPCVP PRDSLNQSLS QDLTMAPGST LWLSCGVPPD SVSRGPLSWT          240
HVHPKGPKSL LSLELKDDRP ARDMWVMETG LLLPRATAQD AGKYYCHRGN LTMSFHLEIT           300
ARPVLWHWLL RTGGWKVSAV TLAYLIFCLC SLVGILHLQR ALVLRRKR                        348

SEQ ID NO: 72            moltype = AA   length = 652
FEATURE                  Location/Qualifiers
source                   1..652
                         mol_type = protein
                         organism = synthetic construct
SEQUENCE: 72
DIQMTQSPSS LSASVGDRVT ITCRASQDVN TAVAWYQQKP GKAPKLLIYS ASFLYSGVPS            60
RFSGSRSGTD FTLTISSLQP EDFATYYCQQ HYTTPPTFGQ GTKVEIKGST SGGGSGGGSG           120
GGGSEVQLV ESGGGLVQPG GSLRLSCAAS GFNIKDTYIH WVRQAPGKGL EWVARIYPTN            180
GYTRYADSVK GRFTISADTS KNTAYLQMNS LRAEDTAVYY CSRWGGDGFY AMDYWGQGTL           240
VTVSSESKYG PPCPPCPAPE FEGGPSVFLF PPKPKDTLMI SRTPEVTCVV VDVSQEDPEV           300
QFNWYVDGVE VHNAKTKPRE EQFQSTYRVV SVLTVLHQDW LNGKEYKCKV SNKGLPSSIE           360
KTISKAKGQP REPQVYTLPP SQEEMTKNQV SLTCLVKGFY PSDIAVEWES NGQPENNYKT           420
TPPVLDSDGS FFLYSRLTVD KSRWQEGNVF SCSVMHEALH NHYTQKSLSL SLGKIYIWAP           480
LAGTCGVLLL SLVITKRGRK KLLYIFKQPF MRPVQTTQEE DGCSCRFPEE EEGGCELGGG           540
RVKFSRSADA PAYQQGQNQL YNELNLGRRE EYDVLDKRRG RDPEMGGKPR RKNPQEGLYN           600
ELQKDKMAEA YSEIGMKGER RRGKGHDGLY QGLSTATKDT YDALHMQALP PR                   652

SEQ ID NO: 73            moltype = AA   length = 544
FEATURE                  Location/Qualifiers
source                   1..544
                         mol_type = protein
                         organism = synthetic construct
SEQUENCE: 73
DIQLTQSPST LSASVGDRVT ITCSASSSVR FIHWYQQKPG KAPKRLIYDT SKLASGVPSR            60
FSGSGSGTDF TLTISSLQPE DFATYYCQQW GSSPFTFGQG TKVEIKGSTS GGGSGGGSGG           120
GGSSEVQLVE YGGGLVQPGG SLRLSCAASG FNIKDYYIHW VRQAPGKGLE WVAWIDPENG           180
DTEFVPKFQG RATMSADTSK NTAYLQMNSL RAEDTAVYYC KTGGFWGQGT LVTVSSESKY           240
GPPCPPCPGG GSSGGGSGGQ PREPQVYTLP PSQEEMTKNQ VSLTCLVKGF YPSDIAVEWE           300
SNGQPENNYK TTPPVLDSDG SFFLYSRLTV DKSRWQEGNV FSCSVMHEAL HNHYTQKSLS           360
LSLGKMALIV LGGVAGLLLF IGLGIFFKRG RKKLLYIFKQ PFMRPVQTTQ EEDGCSCRFP           420
EEEEGGCELG GRVKFSRSA DAPAYQQGQN QLYNELNLGR REEYDVLDKR RGRDPEMGGK            480
PRRKNPQEGL YNELQKDKMA EAYSEIGMKG ERRRGKGHDG LYQGLSTATK DTYDALHMQA           540
LPPR                                                                       544

SEQ ID NO: 74            moltype = AA   length = 425
FEATURE                  Location/Qualifiers
source                   1..425
                         mol_type = protein
                         organism = synthetic construct
SEQUENCE: 74
DIQLTQSPST LSASVGDRVT ITCSASSSVR FIHWYQQKPG KAPKRLIYDT SKLASGVPSR            60
FSGSGSGTDF TLTISSLQPE DFATYYCQQW GSSPFTFGQG TKVEIKGSTS GGGSGGGSGG           120
GGSSEVQLVE YGGGLVQPGG SLRLSCAASG FNIKDYYIHW VRQAPGKGLE WVAWIDPENG           180
DTEFVPKFQG RATMSADTSK NTAYLQMNSL RAEDTAVYYC KTGGFWGQGT LVTVSSGGGS           240
```

```
SGGGSGMALI VLGGVAGLLL FIGLGIFFKR GRKKLLYIFK QPFMRPVQTT QEEDGCSCRF  300
PEEEEGGCEL GGGRVKFSRS ADAPAYQQGQ NQLYNELNLG RREEYDVLDK RRGRDPEMGG  360
KPRRKNPQEG LYNELQKDKM AEAYSEIGMK GERRRGKGHD GLYQGLSTAT KDTYDALHMQ  420
ALPPR                                                             425

SEQ ID NO: 75            moltype = AA   length = 644
FEATURE                  Location/Qualifiers
source                   1..644
                         mol_type = protein
                         organism = synthetic construct
SEQUENCE: 75
DIQLTQSPST LSASVGDRVT ITCSASSSVR FIHWYQQKPG KAPKRLIYDT SKLASGVPSR  60
FSGSGSGTDF TLTISSLQPE DFATYYCQQW GSSPFTFGQG TKVEIKGSTS GGGSGGGSGG  120
GGSSEVQLVE YGGGLVQPGG SLRLSCAASG FNIKDYYIHW VRQAPGKGLE WVAWIDPENG  180
DTEFVPKFQG RATMSADTSK NTAYLQMNSL RAEDTAVYYC KTGGFWGQGT LVTVSSESKY  240
GPPCPPCPAP EFEGGPSVFL FPPKPKDTLM ISRTPEVTCV VVDVSQEDPE VQFNWYVDGV  300
EVHNAKTKPR EEQFQSTYRV VSVLTVLHQD WLNGKEYKCK VSNKGLPSSI EKTISKAKGQ  360
PREPQVYTLP PSQEEMTKNQ VSLTCLVKGF YPSDIAVEWE SNGQPENNYK TTPPVLDSDG  420
SFFLYSRLTV DKSRWQEGNV FSCSVMHEAL HNHYTQKSLS LSLGKMALIV LGGVAGLLLF  480
IGLGIFFKRG RKKLLYIFKQ PFMRPVQTTQ EEDGCSCRFP EEEEGGCELG GGRVKFSRSA  540
DAPAYQQGQN QLYNELNLGR REEYDVLDKR RGRDPEMGGK PRRKNPQEGL YNELQKDKMA  600
EAYSEIGMKG ERRRGKGHDG LYQGLSTATK DTYDALHMQA LPPR                  644

SEQ ID NO: 76            moltype = AA   length = 31
FEATURE                  Location/Qualifiers
source                   1..31
                         mol_type = protein
                         organism = Homo sapiens
SEQUENCE: 76
FWVLVVVGGV LACYSLLVTV AFIIFWVRSK R                                 31

SEQ ID NO: 77            moltype = DNA   length = 544
FEATURE                  Location/Qualifiers
source                   1..544
                         mol_type = other DNA
                         organism = synthetic construct
SEQUENCE: 77
ggatctgcga tcgctccggt gcccgtcagt gggcagagcg cacatcgccc acagtcccg   60
agaagttggg ggggagggtc ggcaattgaa ccggtgccta gagaaggtgg cgcggggtaa  120
actgggaaag tgatgtcgtg tactggctcc gccttttttcc cgagggtggg ggagaaccgt  180
atataagtgc agtagtcgcc gtgaacgttc ttttttcgcaa cgggtttgcc gccagaacac   240
agctgaagct tcgaggggct cgcatctctc cttcacgcgc ccgccgccct acctgaggcc   300
gccatccacg ccggttgagt cgcgttctgc cgcctccgtg tcctggtgcc tcctgaactg   360
cgtccgccgt ctaggtaagt ttaaagctca ggtcgagacc gggccttttgt ccggcgctcc   420
cttggagcct acctagactc agccggctct ccacgctttg cctgaccctg cttgctcaac   480
tctacgtctt tgtttcgttt tctgttctgc gccgttacag atccaagctg tgaccggcgc   540
ctac                                                               544

SEQ ID NO: 78            moltype = DNA   length = 79
FEATURE                  Location/Qualifiers
source                   1..79
                         mol_type = other DNA
                         organism = synthetic construct
SEQUENCE: 78
ggctagcgcc accatgctgc tgctcgtgac cagcctgctg ctgtgcgagc tgccccaccc   60
cgcctttctg ctgatcccc                                               79

SEQ ID NO: 79            moltype = DNA   length = 918
FEATURE                  Location/Qualifiers
source                   1..918
                         mol_type = other DNA
                         organism = synthetic construct
SEQUENCE: 79
atatgggaac tgaagaaaga tgtttatgtc gtagaattgg attggtatcc ggatgcccct   60
ggagaaatgg tggtcctcac ctgtgacacc cctgaagaag atggtatcac ctggaccttg  120
gaccagagca gtgaggtctt aggctctgga aaaaccctga ccatccaagt caaagagttt  180
ggagatgctg ccagtacac ctgtcacaaa ggaggcgagg ttctaagcca ttcgctcctg  240
ctgcttcaca aaaaggaaga tggaaattgg tccactgata ttttaaagga ccagaaagaa  300
cccaaaaata agacctttct aagatgcgag gccaagaatt attctggacg tttcacctgc  360
tggtggctga cgacaatcag tactgattg acattcagtg tcaaaagcag cagaggctct  420
tctgaccccc aaggggtgac gtgcggagct gctacactct ctgcagagag tcagaggg   480
gacaacaagg agtatgagta ctcagtggag tgccaggagg acagtgcctg cccagctgct  540
gaggagagtc tgcccattga ggtcatggtg gatgccgttc acaagctcaa gtatgaaaac  600
tacaccagga gcttcttcat cagggacatc atcaaacctg acccacccaa gaacttgcag  660
ctgaagccat taagaattc tcggcaggtg gaggtcagct gggagtaccc tgacacctgg  720
agtactccac attcctactt ctcccctgaca ttctgcgttc aggtccaggg caagagcaag  780
agagaaaaga agatagagt cttcacggac aagacctcag ccacggtcat ctgccgcaaa  840
aatgccagca ttagcgtgcg ggcccaggac cgctactata gctcatcttg gagcgaatgg  900
gcatctgtgc cctgcagt                                                918
```

| SEQ ID NO: 80 | moltype = DNA length = 30 |
| --- | --- |
| FEATURE | Location/Qualifiers |
| source | 1..30 |
| | mol_type = other DNA |
| | organism = synthetic construct |

SEQUENCE: 80

```
gttcctggag tagggtacc tggggtgggc                                           30
```

| SEQ ID NO: 81 | moltype = DNA length = 594 |
| --- | --- |
| FEATURE | Location/Qualifiers |
| source | 1..594 |
| | mol_type = other DNA |
| | organism = synthetic construct |

SEQUENCE: 81

```
gccagaaacc tccccgtggc cactccagac ccaggaatgt tcccatgcct tcaccactcc          60
caaaacctgc tgagggccgt cagcaacatg ctccagaagg ccagacaaac tctagaattt        120
taccccttgca cttctgaaga gattgatcat gaagatatca caaaagataa aaccagcaca       180
gtggaggcct gtttaccatt ggaattaacc aagaatgaga gttgcctaaa ttccagagag         240
acctctttca taactaatgg gagttgcctg gcctccagaa agacctcttt tatgatggcc        300
ctgtgcctta gtagtattta tgaagactcg aagatgtacc aggtggagtt caagaccatg        360
aatgcaaagc ttctgatgga tcctaagagg cagatctttc tagatcaaaa catgctggca       420
gttattgatg agctgatgca ggccctgaat tcaacagtg agactgtgcc acaaaaatcc        480
tcccttgaag aaccgatttt ttataaaact aaaatcaagc tctgcatact tcttcatgct        540
ttcagaattc gggcagtgac tattgataga gtgatgagct atctgaatgc ttcc             594
```

| SEQ ID NO: 82 | moltype = DNA length = 81 |
| --- | --- |
| FEATURE | Location/Qualifiers |
| source | 1..81 |
| | mol_type = other DNA |
| | organism = synthetic construct |

SEQUENCE: 82

```
ttctgggtgc tggtggtggt gggcggggtg ctggcctgct acagcctgct ggtgacagtg          60
gccttcatca tcttttgggt g                                                   81
```

| SEQ ID NO: 83 | moltype = DNA length = 12 |
| --- | --- |
| FEATURE | Location/Qualifiers |
| source | 1..12 |
| | mol_type = other DNA |
| | organism = synthetic construct |

SEQUENCE: 83

```
cggagcaagc gg                                                             12
```

| SEQ ID NO: 84 | moltype = DNA length = 1587 |
| --- | --- |
| FEATURE | Location/Qualifiers |
| source | 1..1587 |
| | mol_type = other DNA |
| | organism = synthetic construct |

SEQUENCE: 84

```
ctagagaaacc atcagatgtt tccagggtgc cccaaggacc tgaaatgacc ctgtgcctta         60
tttgaactaa ccaatcagtt cgcttctcgc ttctgttcgc gcgcttctgc tccccgagct        120
caataaaaga gcccacaacc cctcactcgg ggcgccagtc ctccgattga ctgagtcgcc        180
cgggtacccg tattcccaat aaagcctctt gctgtttgca tccgaatcgt ggactcgctg        240
atccttggga gggtctcctc agattgattg actgcccacc tcgggggtct ttcatttgga        300
ggttccaccg agatttggag accccagccc agggaccacc gacccccccg ccggaggta        360
agctggccag cggtcgtttc gtgtctgtct ctgtctttgt gcgtgtttgt gccggcatct        420
aatgtttgcg cctgcgtctg tactagttag ctaactagct ctgtatctgg cggacccgtg        480
gtggaactga cgagttcgga acacccggcc gcaaccctgg gagacgtccc agggacttcg        540
ggggccgttt ttgtggcccg acctgagtcc aaaaatcccg atcgttttgg actctttggt        600
gcacccccct aataggaggg atatgtggtt ctggtaggag acgagaacct aaaacagttc        660
ccgcctccgt ctgaattttt gctttcggtt tgggaccgaa gccgcgccgc gcgtcttgtc        720
tgctgcagca tcgttctgtg ttgtctctgt ctgactgtgt ttctgtattt gtctgaaaat        780
tagggccaga ctgttaccac tcccttaagt ttgacctttag gtcactggaa agatgtcgag        840
cggatcgctc acaaccagtc ggtagatgtc aagaagagac gttggttac cttctgctct        900
gcagaatggc caacctttaa cgtcggatgg ccgcgagacg gcacctttaa ccgagacctc        960
atcacccagg ttaagatcaa ggtctttttca cctggcccgc atggacaccc agaccaggtc       1020
ccctacatcg tgacctggga agccttggct tttgaccccc ctccctgggt caagcccttt       1080
gtacacccta agcctccgcc tcctcttcct ccatccgccc cgtctctccc ccttgaacct       1140
cctcgttcga cccccgcctcg atcctccctt tatccagccc tcactccttc tctaggcgcc       1200
cccatatgc catatgagat cttatatggg gcacccccgc ccttgtaaa cttccctgac         1260
cctgacatga caagagttac taacagcccc tctctccaag ctcacttaca ggctctctac       1320
ttagtccagc acgaagtctg gagacctctg gcggcagcct accaagaaca actggaccga       1380
ccggtggtac ctcacccttta ccgagtcggc gacacagtg gggtccgccg acaccagact       1440
aagaactag aacctgctg gaaaggacct tacacagtcc tgctgaccac ccccaccgcc       1500
ctcaaagtag acggcatcgc agcttggata cacgccgccc acgtgaaggc tgccgacccc       1560
gggggtggac catcctctag actgccg                                            1587
```

| SEQ ID NO: 85 | moltype = DNA length = 1005 |
| --- | --- |
| FEATURE | Location/Qualifiers |

```
source                  1..1005
                        mol_type = other DNA
                        organism = synthetic construct
SEQUENCE: 85
atgtgtcctc agaagctaac catctcctgg tttgccatcg ttttgctggt gtctccactc   60
atggccatgt gggagctgga gaaagacgtt tatgttgtag aggtggactg gactcccgat  120
gcccctggag aaacagtgaa cctcacctgt gacacgcctg aagaagatga catcacctgg  180
acctcagacc agagacatgg agtcataggc tctggaaaga ccctgaccat cactgtcaaa  240
gagtttctag atgctggcca gtacacctgc acaaaggag gcgagactct gagccactca  300
catctgctgc tccacaagaa ggaaaatgga atttggtcca ctgaaatttt aaaaaatttc  360
aaaaacaaga ctttcctgaa gtgtgaagca ccaaattact ccggacggtt cacgtgctca  420
tggctggtgc aaagaaacat ggacttgaag ttcaacatca agagcagtag cagttcccct  480
gactctcggg cagtgacatg tggaatggcg tctctgtctg cagagaaggt cacactggac  540
caaagggact atgagaagta ttcagtgtcc tgccaggaga atgtcacctg cccaactgga  600
gaggagaccc tgcccattga actggcgttg gaagcacggc agcagaataa atatgagaac  660
tacagcacca gcttcttcat cagggacatc atcaaaccag accgcccaa gaacttgcag  720
atgaagcctt tgaagaactc acaggtggag gtcagctggg agtacccctga ctcctggagc  780
actccccatt cctacttctc cctcaagttc tttgttcgaa tccagcgcaa gaaagaaaag  840
atgaaggaga cagaggaggg gtgtaaccag aaaggtgcgt tcctcgtaga aagacatct  900
accgaagtcc aatgcaaagg cgggaatgtc tgcgtgcaag ctcaggatcg ctattacaat  960
tcctcatgca gcaagtgggc atgtgttccc tgcagggtcc gatcc              1005

SEQ ID NO: 86           moltype = DNA   length = 45
FEATURE                 Location/Qualifiers
source                  1..45
                        mol_type = other DNA
                        organism = synthetic construct
SEQUENCE: 86
ggcggcggcg ggagtggcgg cggggttct ggcggaggcg gtagc                     45

SEQ ID NO: 87           moltype = DNA   length = 579
FEATURE                 Location/Qualifiers
source                  1..579
                        mol_type = other DNA
                        organism = synthetic construct
SEQUENCE: 87
agggtcattc cagtctctgg acctgccagg tgtcttagcc agtcccgaaa cctgctgaag   60
accacagatg acatggtgaa gacggccaga gaaaaactga acattattc ctgcactgct   120
gaagacatcg atcatgaaga catcacacgg gaccaaacca gcacattgaa gacctgttta  180
ccactggaac tacacaagaa cgagagttgc ctggctacta gagagacttc ttccacaaca  240
agagggagct gcctgccccc acagaagacg tctttgatga tgaccctgtg ccttggtagc  300
atctatgagg acttgaagat gtaccagaca gagttccagg ccatcaacgc agcacttcag  360
aatcacaacc atcagcagat cattctagac aagggcatgc tggtggccat cgatgagctg  420
atgcagtctc tgaatcataa tggcgagact ctgcgccaga aacctcctgt gggagaagca  480
gacccttaca gagtgaaaat gaagctctgc atcctgcttc acgccttcag cacccgcgtc  540
gtgaccatca cagggtgat gggctatctg agctccgcc                           579

SEQ ID NO: 88           moltype = DNA   length = 81
FEATURE                 Location/Qualifiers
source                  1..81
                        mol_type = other DNA
                        organism = synthetic construct
SEQUENCE: 88
ttttgggcac tggtcgtggt tgctggagtc ctgttttgtt atggcttgct agtgacagtg   60
gctctttgtg ttatctggac a                                              81

SEQ ID NO: 89           moltype = DNA   length = 12
FEATURE                 Location/Qualifiers
source                  1..12
                        mol_type = other DNA
                        organism = synthetic construct
SEQUENCE: 89
aatagtagaa gg                                                        12
```

MEMBRANE-BOUND IL-12 FOR CELLULAR IMMUNOTHERAPY

CLAIM OF PRIORITY

This application claims the benefit of International Application No. PCT/US2023/064180 filed Mar. 10, 2023, which claims benefit of U.S. Provisional Application Ser. No. 63/318,753, filed on Mar. 10, 2022 and U.S. Provisional Application Ser. No. 63/423,479, filed on Nov. 7, 2022. The entire contents of the foregoing are incorporated herein by reference.

SEQUENCE LISTING

This application contains a Sequence Listing that has been submitted electronically as an XML file named 40056-0071001_SL_ST26.xml. The XML file, created on Mar. 20, 2024, is 92,599 bytes in size. The material in the XML file is hereby incorporated by reference in its entirety.

TECHNICAL FIELD

This disclosure relates immune cells expressing both a membrane bound IL-12 and optionally a chimeric antigen receptor (CAR).

BACKGROUND

Chimeric antigen receptor (CAR) engineered T cells have energized the field of cancer immunotherapy with their proven ability to treat hematological malignancies, yet the success of CAR T cells against solid tumors has been limited. The relative lack of success of CAR T cell therapy against solid tumors is likely due to a variety of factors, including: the antigen heterogeneity of solid tumors, the difficulty trafficking CAR T cells to solid tumors, and paucity of tumor selective targets. Thus, there is a need for CAR T cell therapies that are effective against solid tumors.

SUMMARY

The present disclosure is based, at least in part, on the discovery that T cells expressing a chimeric antigen receptor (CAR T cells) and membrane-bound IL-12 exhibit improved function compared to otherwise identical CAR T cells that do not express membrane-bound IL-12 and that CAR T cells administered with cells that express membrane bound IL-12 exhibit improved function compared to CAR T cells that are not administered with cells that express membrane bound IL-12 For example, administration of cells expressing membrane-bound IL-12 can increase the ability of CAR T cells to eliminate target cells (e.g., cancer cells) that are relatively distant from the site at which the CAR T cells are administered. Accordingly, aspects of the present disclosure provide nucleic acid molecules encoding a membrane bound IL-12 having a human CD28 transmembrane domain ("mb IL-12" or "mb(28)IL-12"). In some embodiments, the mature membrane bound IL-12 includes, from amino to carboxy terminus: mature human IL-12 beta (p40) subunit, an optional first peptide linker, mature human IL-12 alpha (p35) subunit, an optional second peptide linker, human CD28 transmembrane domain. In some embodiments, all or a portion of the cytoplasmic domain of human CD28 follows the transmembrane domain. A signal sequence can precede the human IL-12 beta subunit.

In some embodiments, a useful mbIL-12 construct comprises from amino to carboxy terminus: a mature human IL-12 beta (p40) subunit, an optional first peptide linker, and a mature human IL-12 alpha (p35) subunit, an optional second peptide linker, human CD28 transmembrane domain. In some embodiments, a useful mbIL-12 construct further comprises an intracellular portion (e.g., at least 4 (e.g., 4, 5, 6, 7, 8, 9 or 10 or no more than 4, 5, 6, 7, 8, 9 or 10 contiguous amino acids of the cytoplasmic domain of human CD28 following the human CD28 transmembrane domain). In some embodiments, all or a portion of the cytoplasmic domain of human CD28 follows the transmembrane domain. A signal sequence can precede the human IL-12 beta subunit.

The p40 subunit portion can comprise or consist of the sequence:

(SEQ ID NO: 1)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS

A useful p40 subunit can comprise 1, 2, 3, 4, or 5 amino acid modifications, (e.g., substitutions). In some embodiments the amino acid modifications are conservative amino acid substitutions.

The p35 subunit portion can comprise or consist of the sequence:

(SEQ ID NO: 2)
ARNLPVATPDPGMFPCLHHSQNLLRAVSNMLQKARQTLEFYPCTSEEID

HEDITKDKTSTVEACLPLELTKNESCLNSRETSFITNGSCLASRKTSFM

MALCLSSIYEDSKMYQVEFKTMNAKLLMDPKRQIFLDQNMLAVIDELMQ

ALNFNSETVPQKSSLEEPDFYKTKIKLCILLHAFRIRAVTIDRVMSYLN

AS

The p35 subunit portion can comprise or consist of the sequence:

(SEQ ID NO: 3)
ARNLPVATPDPGMFPCLHHSQNLLRAVSNMLQKARQTLEFYPCTSEEID

HEDITKDKTSTVEACLPLELTKNESCLNSRETSFITNGSCLASRKTSFM

MALCLSSIYEDLKMYQVEFKTMNAKLLMDPKRQIFLDQNMLAVIDELMQ

ALNFNSETVPQKSSLEEPDFYKTKIKLCILLHAFRIRAVTIDRVMSYLN

AS

A useful p35 subunit can comprise 1, 2, 3, 4, or 5 amino acid modifications, (e.g., substitutions). For example, the amino acid S (underlined above) at position 110 of SEQ ID NOs: 2 can be modified and replaced by a polar, non-charged amino acid, and in some embodiments, the amino acid can be selected from: cysteine, threonine, tyrosine, asparagine, and glutamine. In some embodiments, the amino acid L (underlined above) at position 110 of SEQ ID NOs:

3 can be modified and replaced by a non-polar amino acid, and in some embodiments, the amino acid can be selected from: glycine, alanine, valine, isoleucine, proline, phenylalanine, methionine, and tryptophan.

The human CD28 transmembrane domain can comprise or consist of the sequence:

```
                                          (SEQ ID NO: 16)
FWVLVVVGGVLACYSLLVTVAFIIFWV
```

The human CD28 transmembrane domain can comprise or consist of the sequence:

```
                                          (SEQ ID NO: 17)
MFWVLVVVGGVLACYSLLVTVAFIIFWV
```

The human CD28 transmembrane domain can comprise or consist of the sequence:

```
                                          (SEQ ID NO: 76)
FWVLVVVGGVLACYSLLVTVAFIIFWVRSKR
```

The first peptide linker can comprise or consist of, for example, the sequence

```
                                          (SEQ ID NO: 4)
VPGVGVPGVG
```

The second peptide linker can comprise or consist of, for example, the sequence:

```
GGG
```

The first and second linker peptide linker can be have any suitable sequence. For example, the first peptide linker can consist of: 3-24 amino acids, 3-20 amino acids, 3-15 amino acids, 3-10 amino acids (e.g., 3, 4, 5, 6, 7, 8, 9, 10, 11, 12, 13, 14, 15, 16, 17, 18, 19, or 20 amino acids. Preferably, none of the amino acids are proline. For example, the second peptide linker can consist of: 3-24 amino acids, 3-20 amino acids, 3-15 amino acids, 3-10 amino acids (e.g., 3, 4, 5, 6, 7, 8, 9, 10, 11, 12, 13, 14, 15, 16, 17, 18, 19, or 20 amino acids. Preferably, none of the amino acids are proline. Suitable second peptide linkers include glycines and or a mixture of glycines and serines (e.g., GGGGSGGGGS GGGGSGGGGS (SEQ ID NO: 57), GGGG (SEQ ID NO: 58), GGGGS (SEQ ID NO: 14), GGGSGG (SEQ ID NO: 59) and GGGSGGGS (SEQ ID NO: 60). The first and second linker peptide linker can be have any suitable sequence. For example, the first peptide linker can consist of: 3-24 amino acids, 3-20 amino acids, 3-15 amino acids, 3-10 amino acids (e.g., 3, 4, 5, 6, 7, 8, 9, 10, 11, 12, 13, 14, 15, 16, 17, 18, 19, or 20 amino acids. Preferably, none of the amino acids are proline. For example, the second peptide linker can consist of: 3-24 amino acids, 3-20 amino acids, 3-15 amino acids, 3-10 amino acids (e.g., 3, 4, 5, 6, 7, 8, 9, 10, 11, 12, 13, 14, 15, 16, 17, 18, 19, or 20 amino acids. Preferably, none of the amino acids are proline. Suitable second peptide linkers include glycines and or a mixture of glycines and serines (e.g., GGGGSGGGGS GGGGSGGGGS (SEQ ID NO: 57), GGGG (SEQ ID NO: 58), GGGGS (SEQ ID NO: 14), GGGSGG (SEQ ID NO: 59) and GGGSGGGGS (SEQ ID NO: 60). In some embodiments, a useful flexible linker is 1, 2, 3, 4, 5, 6, 7, 8, 9, or 10 repeats of the sequence GGGS (SEQ ID NO: 13). In some embodiments, a useful flexible linker is 1, 2, 3, 4, 5, 6, 7, 8, 9, or 10 repeats of the sequence GGGGS (SEQ ID NO: 14) or SEQ ID NO:13. In some embodiments, the linker comprises the sequence SSGGGGSGGGGSGGGGS (SEQ ID NO:12)

The human CD28 cytoplasmic domain portion can comprise or consist of the sequence:

```
                                          (SEQ ID NO: 5)
RSKR
```

The portion of the human cytoplasmic domain when present preferably lacks signaling activity.

In some embodiments, a mature mb(28)IL-12 can comprise or consist of the sequence:

```
                                          (SEQ ID NO: 6)
IWELKKDVYVVELDWYPDAPGEMVVLTCDTPEEDGITWTLDQSSE

VLGSGKTLTIQVKEFGDAGQYTCHKGGEVLSHSLLLLHKKEDGIW

STDILKDQKEPKNKTFLRCEAKNYSGRFTCWWLTTISTDLTFSVK

SSRGSSDPQGVTCGAATLSAERVRGDNKEYEYSVECQEDSACPAA

EESLPIEVMVDAVHKLKYENYTSSFFIRDIIKPDPPKNLQLKPLK

NSRQVEVSWEYPDTWSTPHSYFSLTFCVQVQGKSKREKKDRVFTD

KTSATVICRKNASISVRAQDRYYSSSWSEWASVPCSVPGVGVPGV

GARNLPVATPDPGMFPCLHHSQNLLRAVSNMLQKARQTLEFYPCT

SEEIDHEDITKDKTSTVEACLPLELTKNESCLNSRETSFITNGSC

LASRKTSFMMALCLSSIYEDSKMYQVEFKTMNAKLLMDPKRQIFL

DQNMLAVIDELMQALNFNSETVPQKSSLEEPDFYKTKIKLCILLH

AFRIRAVTIDRVMSYLNASGGGFWVLVVVGGVLACYSLLVTVAFI

IFWVRSKR
```

In some embodiments, a mature mb(28)IL-12 can comprise or consist of the sequence:

```
                                          (SEQ ID NO: 7)
IWELKKDVYVVELDWYPDAPGEMVVLTCDTPEEDGITWTLDQSSE

VLGSGKTLTIQVKEFGDAGQYTCHKGGEVLSHSLLLLHKKEDGIW

STDILKDQKEPKNKTFLRCEAKNYSGRFTCWWLTTISTDLTFSVK

SSRGSSDPQGVTCGAATLSAERVRGDNKEYEYSVECQEDSACPAA

EESLPIEVMVDAVHKLKYENYTSSFFIRDIIKPDPPKNLQLKPLK

NSRQVEVSWEYPDTWSTPHSYFSLTFCVQVQGKSKREKKDRVFTD

KTSATVICRKNASISVRAQDRYYSSSWSEWASVPCSVPGVGVPGV

GARNLPVATPDPGMFPCLHHSQNLLRAVSNMLQKARQTLEFYPCT

SEEIDHEDITKDKTSTVEACLPLELTKNESCLNSRETSFITNGSC

LASRKTSFMMALCLSSIYEDLKMYQVEFKTMNAKLLMDPKRQIFL

DQNMLAVIDELMQALNFNSETVPQKSSLEEPDFYKTKIKLCILLH

AFRIRAVTIDRVMSYLNASGGGFWVLVVVGGVLACYSLLVTVAFI

IFWVRSKR
```

In the above mature mb(28)IL-12 sequences, the first and second peptide linker sequences are underlined; the human CD28 transmembrane domain sequence is in bold and the portion of human CD28 cytoplasmic domain sequence is in italics. A useful mb(28)IL-12 can comprise SEQ ID NO:6 with 1, 2, 3, 4, 5 amino acid modification or comprise a sequence with 80, 85, 88, 89, 90, 91, 92, 93, 94, 95, 96, 97, 98, 99, or 100% identity to SEQ ID NO:6. A useful mb(28) IL-12 can comprise SEQ ID NO:7 with 1, 2, 3, 4, 5 amino acid modification or comprise a sequence with 80, 85, 88, 89, 90, 91, 92, 93, 94, 95, 96, 97, 98, 99, or 100% identity to SEQ ID NO:7.

The mature sequence can be preceded by a signal sequence suitable for directing secretion to the surface of a human cell. For example, the signal sequence can comprise or consist of the sequence: MCHQQLVISWFSLV-FLASPLVA (SEQ ID NO: 10).

In one aspect, a mbIL-12 with a signal sequence can comprise or consist of the sequence:

(SEQ ID NO: 8)
MCHQQLVISWFSLVFLASPLVAIWELKKDVYVVELDWYPDAPGEM

VVLTCDTPEEDGITWTLDQSSEVLGSGKTLTIQVKEFGDAGQYTC

HKGGEVLSHSLLLLHKKEDGIWSTDILKDQKEPKNKTFLRCEAKN

YSGRFTCWWLTTISTDLTFSVKSSRGSSDPQGVTCGAATLSAERV

RGDNKEYEYSVECQEDSACPAAEESLPIEVMVDAVHKLKYENYTS

SFFIRDIIKPDPPKNLQLKPLKNSRQVEVSWEYPDTWSTPHSYFS

LTFCVQVQGKSKREKKDRVFTDKTSATVICRKNASISVRAQDRYY

SSSWSEWASVPCSVPGVGVPGVGARNLPVATPDPGMFPCLHHSQN

LLRAVSNMLQKARQTLEFYPCTSEEIDHEDITKDKTSTVEACLPL

ELTKNESCLNSRETSFITNGSCLASRKTSFMMALCLSSIYEDSKM

YQVEFKTMNAKLLMDPKRQIFLDQNMLAVIDELMQALNFNSETVP

QKSSLEEPDFYKTKIKLCILLHAFRIRAVTIDRVMSYLNASGGGF

WVLVVVGGVLACYSLLVTVAFIIFWVRSKR

In this sequence the signal sequence is underlined.

In one aspect, mb(DC28)IL-12 with a signal sequence can comprise or consist of the sequence:

(SEQ ID NO: 9)
MCHQQLVISWFSLVFLASPLVAIWELKKDVYVVELDWYPDAPGEM

VVLTCDTPEEDGITWTLDQSSEVLGSGKTLTIQVKEFGDAGQYTC

HKGGEVLSHSLLLLHKKEDGIWSTDILKDQKEPKNKTFLRCEAKN

YSGRFTCWWLTTISTDLTFSVKSSRGSSDPQGVTCGAATLSAERV

RGDNKEYEYSVECQEDSACPAAEESLPIEVMVDAVHKLKYENYTS

SFFIRDIIKPDPPKNLQLKPLKNSRQVEVSWEYPDTWSTPHSYFS

LTFCVQVQGKSKREKKDRVFTDKTSATVICRKNASISVRAQDRYY

SSSWSEWASVPCSVPGVGVPGVGARNLPVATPDPGMFPCLHHSQN

LLRAVSNMLQKARQTLEFYPCTSEEIDHEDITKDKTSTVEACLPL

ELTKNESCLNSRETSFITNGSCLASRKTSFMMALCLSSIYEDLKM

YQVEFKTMNAKLLMDPKRQIFLDQNMLAVIDELMQALNFNSETVP

QKSSLEEPDFYKTKIKLCILLHAFRIRAVTIDRVMSYLNASGGGF

WVLVVVGGVLACYSLLVTVAFIIFWVRSKR

In this sequence, the signal sequence is underlined.

In other aspects, the signal sequence can comprise or consist of:

(SEQ ID NO: 11)
MLLLVTSLLLCELPHPAFLLIP

In some embodiments, a mbIL-12 with a signal sequence can comprise or consist of the sequence:

(SEQ ID NO: 48)
MLLLVTSLLLCELPHPAFLLIPIWELKKDVYVVELDWYPDAPGEM

VVLTCDTPEEDGITWTLDQSSEVLGSGKTLTIQVKEFGDAGQYTC

HKGGEVLSHSLLLLHKKEDGIWSTDILKDQKEPKNKTFLRCEAKN

YSGRFTCWWLTTISTDLTFSVKSSRGSSDPQGVTCGAATLSAERV

RGDNKEYEYSVECQEDSACPAAEESLPIEVMVDAVHKLKYENYTS

SFFIRDIIKPDPPKNLQLKPLKNSRVEVSWEYPDTWSTPHSYFSL

TFCVQVQGKSKREKKDRVFTDKTSATVICRKNASISVRAQDRYYS

SSWSEWASVPCSVPGVGVPGVGARNLPVATPDPGMFPCLHHSQNL

LRAVSNMLQKARQTLEFYPCTSEEIDHEDITKDKTSTVEACLPLE

LTKNESCLNSRETSFITNGSCLASRKTSFMMALCLSSIYEDSKMY

QVEFKTMNAKLLMDPKRQIFLDQNMLAVIDELMQALNFNSETVPQ

KSSLEEPDFYKTKIKLCILLHAFRIRAVTIDRVMSYLNASGGGFW

VLVVVGGVLACYSLLVTVAFIIFW

VRSKR

In this sequence, the signal sequence is underlined.

In some embodiments, a mbIL-12 with a signal sequence can comprise or consist of the sequence:

(SEQ ID NO: 49)
MLLLVTSLLLCELPHPAFLLIPIWELKKDVYVVELDWYPDAPGEM

VVLTCDTPEEDGITWTLDQSSEVLGSGKTLTIQVKEFGDAGQYTC

HKGGEVLSHSLLLLHKKEDGIWSTDILKDQKEPKNKTFLRCEAKN

YSGRFTCWWLTTISTDLTFSVKSSRGSSDPQGVTCGAATLSAERV

RGDNKEYEYSVECQEDSACPAAEESLPIEVMVDAVHKLKYENYTS

SFFIRDIIKPDPPKNLQLKPLKNSRQVEVSWEYPDTWSTPHSYFS

LTFCVQVQGKSKREKKDRVFTDKTSATVICRKNASISVRAQDRYY

SSSWSEWASVPCSVPGVGVPGVGARNLPVATPDPGMFPCLHHSQN

LLRAVSNMLQKARQTLEFYPCTSEEIDHEDITKDKTSTVEACLPL

ELTKNESCLNSRETSFITNGSCLASRKTSFMMALCLSSIYEDLKM

YQVEFKTMNAKLLMDPKRQIFLDQNMLAVIDELMQALNFNSETVP

QKSSLEEPDFYKTKIKLCILLHAFRIRAVTIDRVMSYLNASGGGF

WVLVVVGGVLACYSLLVTVAFIIFWVRSKR

In this sequence, the signal sequence is underlined.

In some embodiments, a mb(28)IL12 described herein can comprise a sequence selected from SEQ ID NO:6, 7, 8, 9, 48, 49, or a variant of each having 1, 2, 3, 4, 5 amino acid modifications. In some embodiments, a mb(28)IL12 described herein can comprise a sequence 80, 85, 88, 89, 90, 91, 92, 93, 94, 95, 96, 97, 98, 99, or 100% identity to any one of SEQ ID NO: 6, 7, 8, 9, 48, and 49. In some embodiments, the sequence FWVLVVVGGVLACYSLL-VTVAFIIFWV (SEQ ID NO: 16) can be replaced with MFWVLVVVGGVLACYSLLVTVAFIIFWV (SEQ ID NO: 17) or FWVLVVVGGVLACYSLLVTVAFIIFWVR-SKR (SEQ ID NO: 76). In some embodiments, the portion of the human cytoplasmic domain when present preferably lacks signaling activity.

Nucleic acids described herein can comprise a sequence encoding a sequence selected from SEQ ID NO:6, 7, 8, 9, 48, 49, or a variant of each having 1, 2, 3, 4, 5 amino acid modifications. In some embodiments, a nucleic acid can comprise a sequence encoding a sequence having 80, 85, 88, 89, 90, 91, 92, 93, 94, 95, 96, 97, 98, 99, or 100% identity to any one of SEQ ID NO:6, 7, 8, 9, 48, and 49. In some embodiments, the sequence FWVLVVVGGVLACYSLL-VTVAFIIFWV (SEQ ID NO: 16) can be replaced with MFWVLVVVGGVLACYSLLVTVAFIIFWV (SEQ ID NO: 17) or FWVLVVVGGVLACYSLLVTVAFIIFWVR-SKR (SEQ ID NO: 76).

Disclosed herein, inter alia, are nucleic acid molecules encoding membrane bound IL-12 (mbIL-12), comprising, from amino to carboxy terminus: mature human IL-12 p40 subunit, an optional first peptide linker, mature human IL-12 p35 subunit, an optional second peptide linker, human CD28 transmembrane domain. In some embodiments, the mbIL-12 further comprises at least 4 contiguous amino acids of the cytoplasmic domain of human CD28 following the human CD28 transmembrane domain. In some embodiments, the amino acid sequence of the mature human IL-12 p40 subunit comprises SEQ ID NO: 1. In some embodiments, the amino acid sequence of the mature human IL-12 p35 comprises SEQ ID NO: 2 or 3. In some embodiments, the first peptide linker comprises the amino acid sequence of SEQ ID NO: 4. In some embodiments, the second peptide linker comprises the amino acid sequence GGG. In some embodiments, the human CD28 transmembrane domain comprises the amino acid sequence of SEQ ID NO: 16 or 17 or 76. In some embodiments, the at least 4 contiguous amino acids of the cytoplasmic domain of human CD28 following the human CD28 transmembrane domain comprises the amino acid sequence of SEQ ID NO: 5. In some embodiments, the mbIL-12 comprises the amino acid sequence of SEQ ID NO: 6 or 7.

Also disclosed herein are populations of human immune cells (e.g., T cells, NK cells, dendritic cells, macrophages or monocytes) comprising a nucleic acid encoding a mb(28) IL12 described herein. In some embodiments, a population of human immune cells comprising a nucleic acid molecule encoding a mb IL-12, comprising, from amino to carboxy terminus: a mature human IL-12 p40 subunit, a first peptide linker, a mature human IL-12 p35 subunit, a second peptide linker, and a human CD28 transmembrane domain. In some embodiments, the mbIL-12 further comprises at least a portion of the cytoplasmic domain of human CD28 following the human CD28 transmembrane domain. In some embodiments, the amino acid sequence of the mature human IL-12 p40 subunit comprises SEQ ID NO: 1. In some embodiments, the amino acid sequence of the mature human IL-12 p35 comprises SEQ ID NO: 2 or 3. In some embodiments, the first peptide linker comprises the amino acid sequence of SEQ ID NO: 4. In some embodiments, the second peptide linker comprises the amino acid sequence GGG. In some embodiments, the human CD28 transmembrane domain comprises the amino acid sequence of SEQ ID NO: 16 or 17 or 76. In some embodiments, the cytoplasmic domain of a human CD28 transmembrane domain comprises at least 4 contiguous amino acids of a cytoplasmic domain of human CD28 following the human CD28 transmembrane domain or comprises the amino acid sequence of SEQ ID NO: 5. In some embodiments, the mbIL-12 comprises the amino acid sequence of SEQ ID NO: 6 or 7. In some embodiments, the population of immune cells is a population of T cells, a population of NK cells, a population of dendritic cells, a population of macrophages, or a population of monocytes.

In some embodiments, a population of immune cells comprise a nucleic acid comprising a sequence encoding a mb(28)IL12 and comprise a nucleic acid comprising a sequence encoding a chimeric antigen receptor (CAR). In some embodiments, the chimeric antigen receptor is targeted to a human antigen selected from the group consisting of: CD19, CD22, BCMA, PSCA, HER2, and TAG-72. In some embodiments, the chimeric antigen receptor is targeted to human TAG-72. In some embodiments, the chimeric antigen receptor comprises: an scFv targeting Tag-72, a spacer, a transmembrane domain, a CD28 co-stimulatory domain or a 41-BB co-stimulatory domain, and a human CD3 ζ signaling domain. In some embodiments, the transmembrane domain is selected from: a CD4 transmembrane domain, a CD8 transmembrane domain, a CD28 transmembrane domain. In some embodiments, the TAG72 scFV is selected from IDEC, V15, V59 and V59_V15. In some embodiments, the transmembrane domain is a human CD28 transmembrane domain. In some embodiments, the spacer region comprises an amino acid sequence selected from the group consisting of SEQ ID NOs: 2-12. In some embodiments, the spacer comprises an IgG hinge region. In some embodiments, the spacer consists of 10-50 amino acids. In some embodiments, the 4-1 BB costimulatory domain comprises the amino acid sequence of SEQ ID NO: 38. In some embodiments, the CD3ζ signaling domain comprises the amino acid sequence of SEQ ID NO:35. In some embodiments, a linker of 3 to 15 amino acids is located between the 4-1 BB costimulatory domain and the CD3 ζ signaling domain or variant thereof.

In some cases, the mbIL-12 constructs described herein is expressed with a CAR, e.g., a CAR targeted to a solid tumor antigen, e.g., HER2 or PSCA.

Described herein, inter alia, are populations of human immune cells (e.g., T cells, NK cells, dendritic cells, macrophages or monocytes) expressing a membrane bound IL-12 (mbIL-12) comprising, from amino to carboxy terminus: a mature human IL-12 p40 subunit, a first peptide linker, a mature human IL-12 p35 subunit, a second peptide linker, and a human CD28 transmembrane domain. In some embodiments, the mbIL-12 further comprises at least a portion of the cytoplasmic domain of human CD28 following the human CD28 transmembrane domain. In some embodiments, the amino acid sequence of the mature human IL-12 p40 subunit comprises SEQ ID NO: 1. In some embodiments, the amino acid sequence of the mature human IL-12 p35 comprises SEQ ID NO: 2 or 3. In some embodiments, the first peptide linker comprises the amino acid sequence of SEQ ID NO: 4. In some embodiments, the second peptide linker comprises the amino acid sequence GGG. In some embodiments, the human CD28 transmembrane domain comprises the amino acid sequence of SEQ ID NO: 16 or 17 or 76. In some embodiments, the cytoplasmic domain of a human CD28 transmembrane domain comprises at least 4 contiguous amino acids of a cytoplasmic domain of human CD28 following the human CD28 transmembrane domain or comprises the amino acid sequence of SEQ ID NO: 5. In some embodiments, the mbIL-12 comprises the amino acid sequence of SEQ ID NO: 6 or 7. In some embodiments, the population of immune cells is a population of T cells, a population of NK cells, a population of dendritic cells, a population of macrophages, or a population of monocytes.

Also described herein are methods for treating cancer comprising administering the human immune cells comprising a nucleic acid encoding a mb(28)IL12 described herein and human immune cells expressing a chimeric antigen receptor. In some embodiments, the immune cells comprising a nucleic acid encoding a mb(28)IL12 described herein are administered before the immune cells expressing a chimeric antigen receptor are administered. In some embodiments, the immune cells comprising a nucleic acid encoding a mb(28)IL12 described herein are administered together with the immune cells expressing a chimeric antigen receptor are administered. In some embodiments, the cancer is a solid tumor. In some embodiments the cancer expresses CD19, CD22, BCMA, PSCA, HER2, TAG-72, or PSCA.

Also described herein are methods for treating cancer comprising administering the human immune cells expressing a mb(28)IL12 described herein and human immune cells expressing a chimeric antigen receptor. In some embodiments, the immune cells expressing a mb(28)IL12 described herein are administered before the immune cells expressing a chimeric antigen receptor are administered. In some embodiments, the immune cells expressing a mb(28)IL12 described herein are administered together with the immune cells expressing a chimeric antigen receptor are administered. In some embodiments, the cancer is a solid tumor. In some embodiments the cancer expresses CD19, CD22, BCMA, PSCA, HER2, TAG-72, or PSCA.

Also described herein, inter alia, are populations of human immune cells (e.g., T cells, NK cells, dendritic cells, macrophages or monocytes) expressing a membrane bound IL-12 (mbIL-12) and a CAR targeted to a cancer antigen, wherein the mbIL-12 comprises, from amino to carboxy terminus: mature human IL-12 p40 subunit, a first peptide linker, mature human IL-12 p35 subunit, a second peptide linker, human CD28 transmembrane domain, and wherein the CAR comprises an scFv targeting a cancer antigen, a spacer, a transmembrane domain, a CD28 co-stimulatory domain or a 4-1 BB co-stimulatory domain, and a human CD3 ζ signaling domain. In some embodiments, the mbIL-12 further comprises a cytoplasmic domain of human CD28 following the human CD28 transmembrane domain. In some embodiments, the amino acid sequence of the mature human IL-12 p40 subunit comprises SEQ ID NO: 1. In some embodiments, the amino acid sequence of the mature human IL-12 p35 comprises SEQ ID NO: 2 or 3. In some embodiments, the first peptide linker comprises the amino acid sequence of SEQ ID NO: 4. In some embodiments, the second peptide linker comprises the amino acid sequence GGG. In some embodiments, the human CD28 transmembrane domain comprises the amino acid sequence of SEQ ID NO: 16 or 17 or 76. In some embodiments, the cytoplasmic domain of a human CD28 transmembrane domain comprises at least 4 contiguous amino acids of a cytoplasmic domain of human CD28 following the human CD28 transmembrane domain or comprises the amino acid sequence of SEQ ID NO: 5. In some embodiments, the mbIL-12 comprises the amino acid sequence of SEQ ID NO: 6 or 7. In some embodiments, the population of human immune cells is a population of human T cells or human NK cells. In some embodiments, the cancer antigen from a solid tumor or a metastasis of a solid tumor. In some embodiments, the cancer antigen is selected from the group consisting of: CD19, CD22, BCMA, PSCA, HER2, and TAG-72. In some embodiments, wherein the transmembrane domain is selected from: a CD4 transmembrane domain, a CD8 transmembrane domain, a CD28 transmembrane domain. In some embodiments, the TAG72 scFV is selected from IDEC, V15, V59 and V59_V15. In some embodiments, the transmembrane domain is a human CD28 transmembrane domain. In some embodiments, the spacer region comprises an amino acid sequence selected from the group consisting of SEQ ID NOs: 2-12. In some embodiments, the spacer comprises an IgG hinge region. In some embodiments, the spacer consists of 10-50 amino acids. In some embodiments, the 4-1 BB costimulatory domain comprises the amino acid sequence of SEQ ID NO: 38. In some embodiments, the CD3ζ signaling domain comprises the amino acid sequence of SEQ ID NO:35. In some embodiments, a linker of 3 to 15 amino acids is located between the 4-1 BB costimulatory domain and the CD3 ζ signaling domain or variant thereof.

In some embodiments, a CAR can comprise any one of SEQ ID NOs: 61, 62, 72, 73, 74, 75, or a variant of each having 1, 2, 3, 4, 5, 6, 7, 8, 9, or 10 amino acid modifications. In some embodiments, a CAR can comprise a sequence having 80, 85, 88, 89, 90, 91, 92, 93, 94, 95, 96, 97, 98, 99, or 100% identity to any one of SEQ ID NOs: 61, 62, 72, 73, 74, and 75.

Also described herein are methods of making a population of T cells (including, e.g., gamma/delta T cells), monocytes, macrophages, dendritic cells or NK cells expressing a mb(28)IL-12 construct and optionally a CAR.

Also described herein are vectors comprising any of the nucleic acid constructs described herein. In some embodiments, the vector is a viral vector. In some embodiments, the vector is a lentiviral vector. In some embodiments, the vector comprises a sequence that encodes any of the mb(28) IL-12 constructs disclosed herein. In some embodiments, a vector comprises a sequence that encodes a sequence selected from SEQ ID NO:6, 7, 8, 9, 48, 49, or a variant of each having 1, 2, 3, 4, 5 amino acid modifications. In some embodiments, a vector comprises a sequence that encodes a sequence having 80, 85, 88, 89, 90, 91, 92, 93, 94, 95, 96, 97, 98, 99, or 100% identity to any one of SEQ ID NO: 6, 7, 8, 9, 48, and 49.

Also disclosed herein are method for treating cancer comprising administering to a patient in need thereof any population of human immune cells (e.g., macrophages, monocytes, T cells or NK cells) described herein. In some embodiments, the patient is suffering from a solid tumor. In some embodiments, the solid tumor is metastatic. In some embodiments, the population of human immune cells (e.g., macrophages, monocytes, T cells or NK cells) is administered intravenously. In some embodiments, the population of human immune cells (e.g., macrophages, monocytes, T cells or NK cells) (e.g., macrophages, monocytes, T cells or NK cells) is administered intraperitoneally. In some embodiments, the population of human immune cells (e.g., macrophages, monocytes, T cells or NK cells) is administered intraperitoneally in the region of the solid tumor. In some embodiments, the solid tumor is ovarian cancer and the chimeric antigen receptor is targeted to TAG72. In some embodiments, the population of human immune cells (e.g., macrophages, monocytes, T cells or NK cells) is allogenic. In some embodiments, the population of human immune cells (e.g., macrophages, monocytes, T cells or NK cells) is autologous. In some embodiments, a therapeutically effective amount of a population of immune cells (e.g., macrophages, monocytes, T cells or NK cells) is administered to the patient. In some embodiments, the cancer is a solid tumor. In some embodiments, the cancer expresses CD19, CD22, BCMA, PSCA, HER2, TAG-72, or PSCA Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

(i) Schema of repetitive tumor cell challenge assay (top). TAG72-CAR/mbIL12(CD28tm) T cells were cocultured with OV90 cells (E:T=1:3) and rechallenged with OV90 cells every two days. Remaining viable tumor cells and fold change in TAG72-CAR T cells were quantified as described in Materials and Methods prior to each tumor cell rechallenge.

Figure 8:
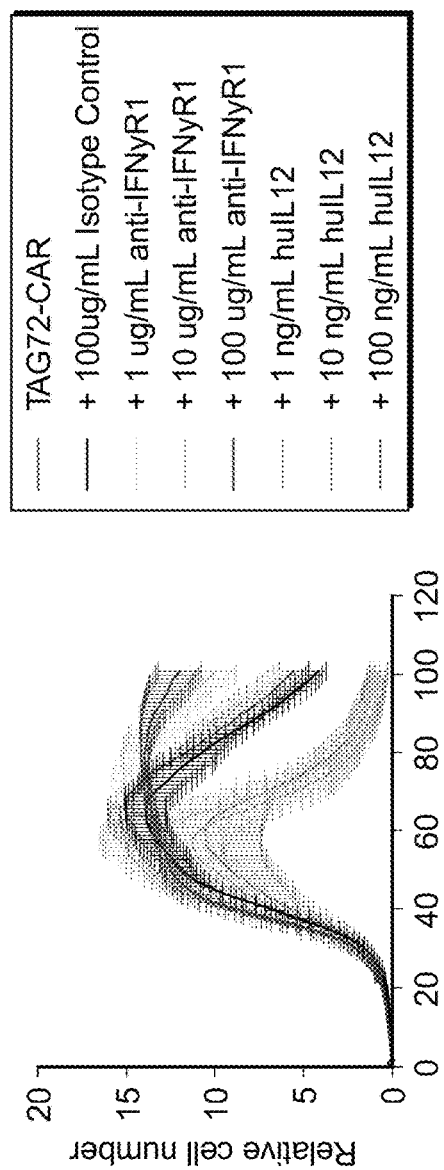

FIG. 8 TAG72-CAR T cell anti-tumor activity is regulated by IFNγ signaling. Tumor cell killing of OVCAR3 cells by TAG72-CAR T cells (E:T=1:50) with varying concentrations of anti-IFNγR1 blocking antibody, isotype control, and recombinant human IL-12 cytokine measured by xCELLigence.

Figure 6:
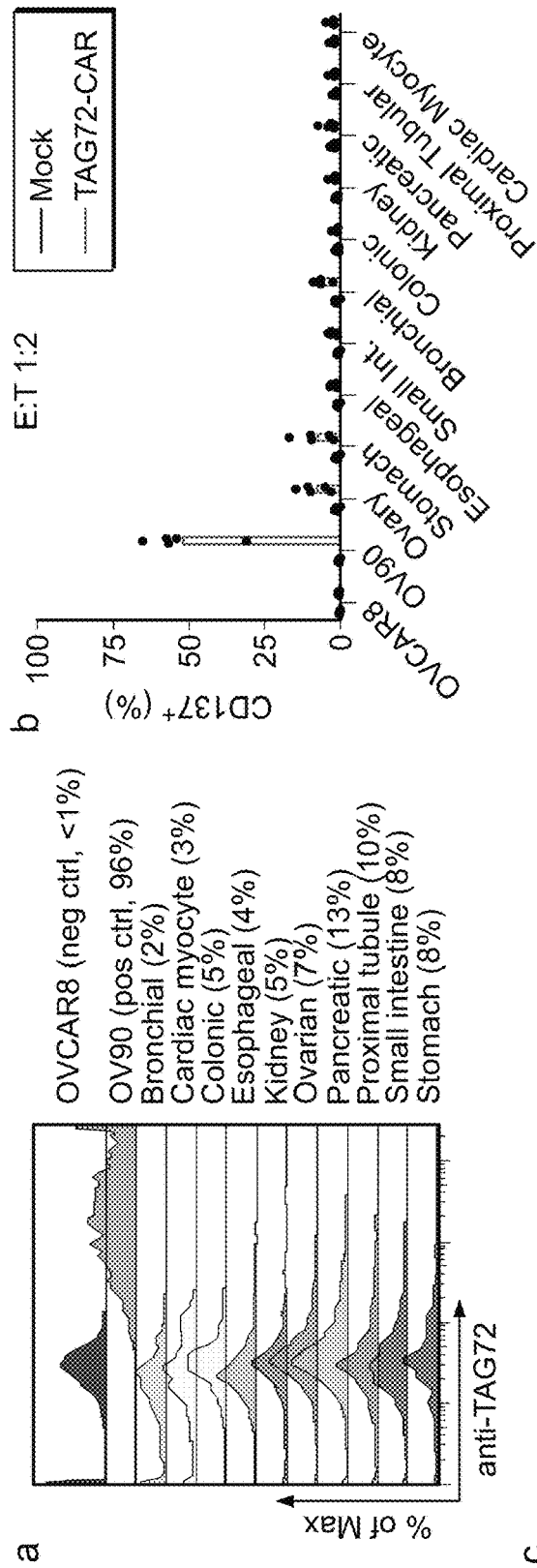
FIG. 6 In vitro safety of TAG72-CAR T cells against normal human cell lines. (a) Flow cytometric analysis of TAG72 expression on the cell surface of TAG72-negative (OVCAR8) tumor cells, TAG72-positive (OV90) tumor cells, and indicated primary human normal cells. (b-c) Quantification of CD137 activation (b), and tumor and normal cell killing by TAG72-dCH2(28tm)BBz CAR T cells relative to UTD T cells at varying E:T ratios (c), assessed by flow cytometry following a 48 hour coculture with indicated cells as described in Materials and Methods. Data are of five independent donors.
Figure 6:
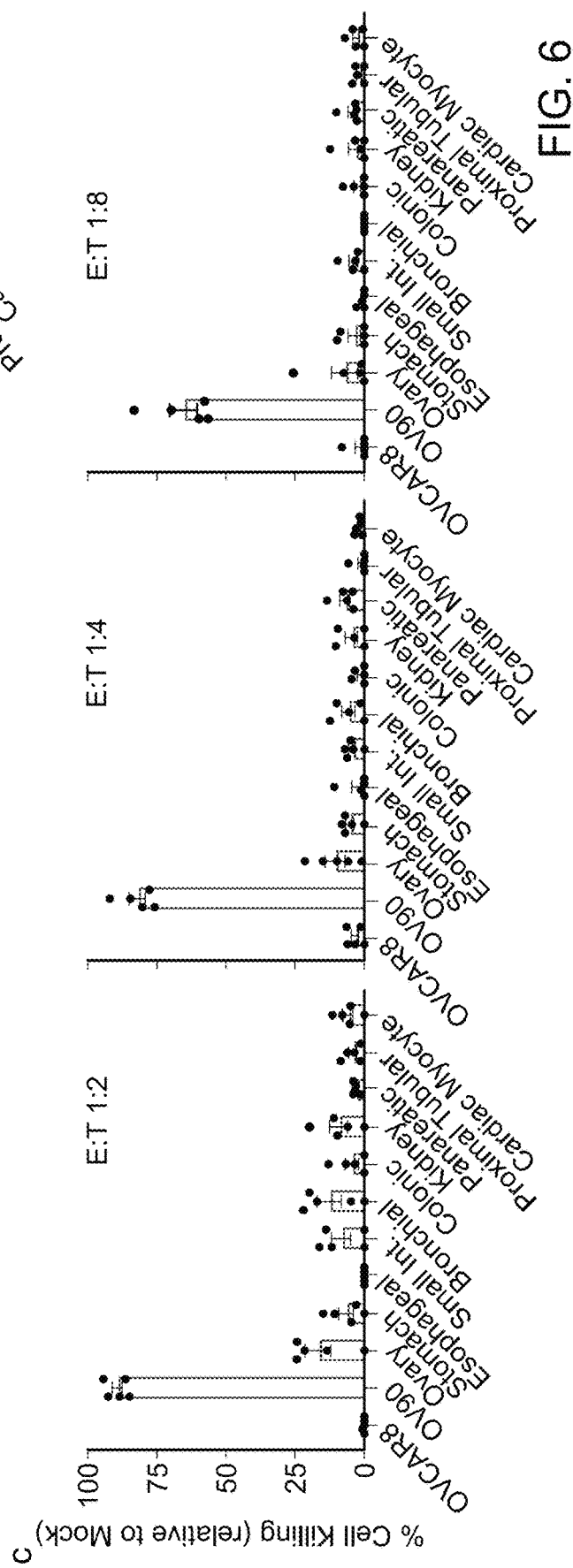
Figure 9:
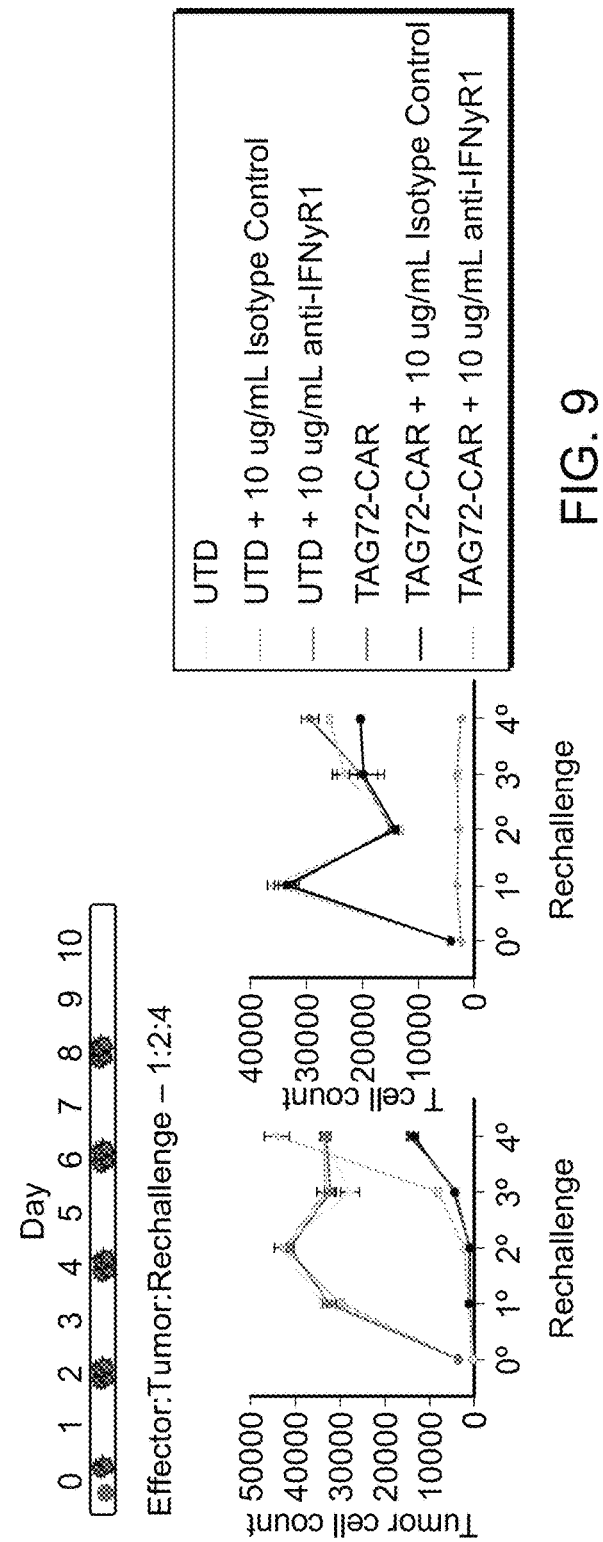

FIG. 9 Supplemental FIG. 6. Inhibition of IFNγ signaling dampens repetitive tumor cell killing by TAG72-CAR T cells. Schema of repetitive tumor cell challenge assay (top). TAG72-CAR T cells were cocultured with OV90 cells (E:T=1:2) and rechallenged with OV90 cells every three days. Remaining viable tumor cells and TAG72-CAR T cells were quantified as described in Materials and Methods prior to each tumor cell rechallenge.

Figure 10:
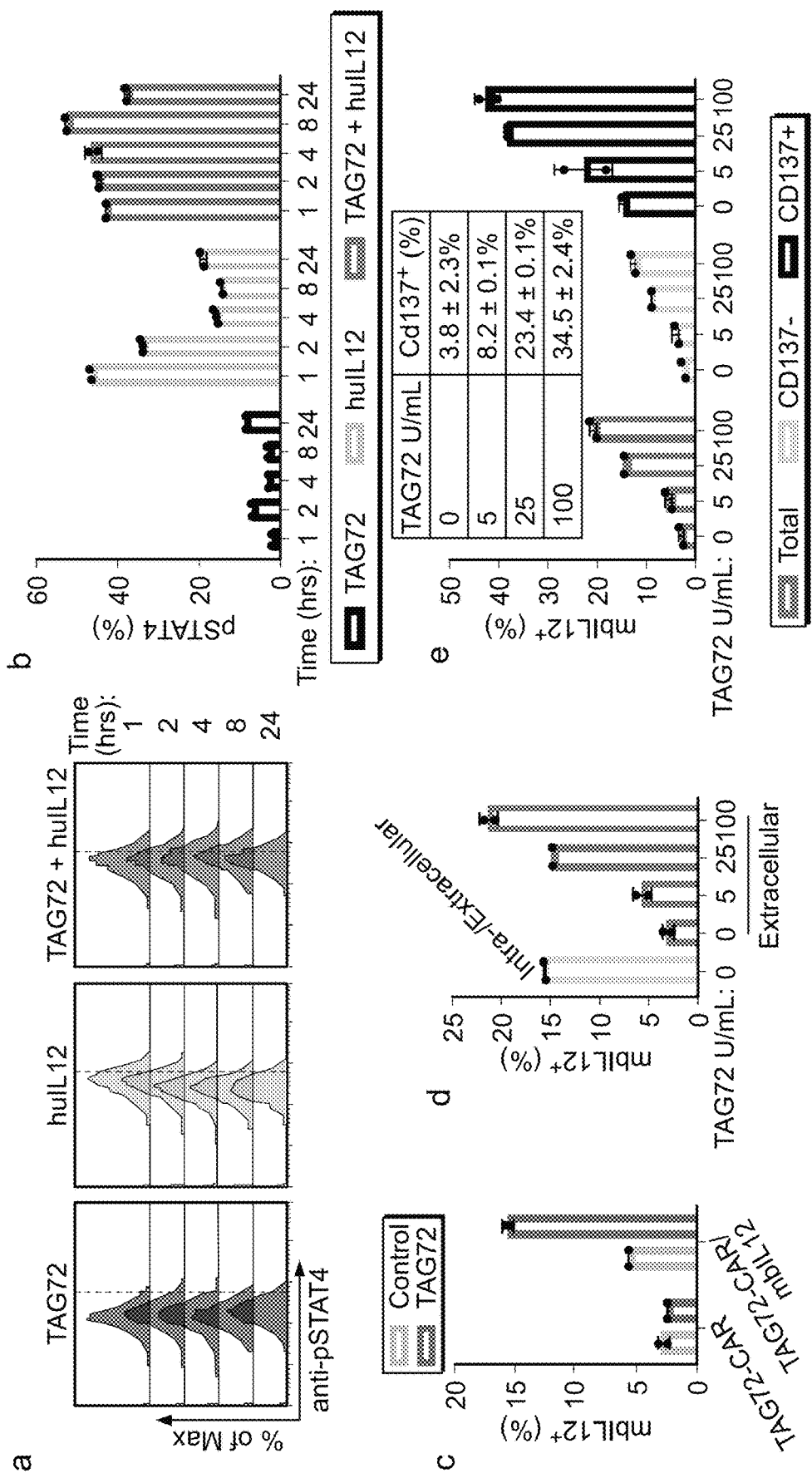
Figure 10:
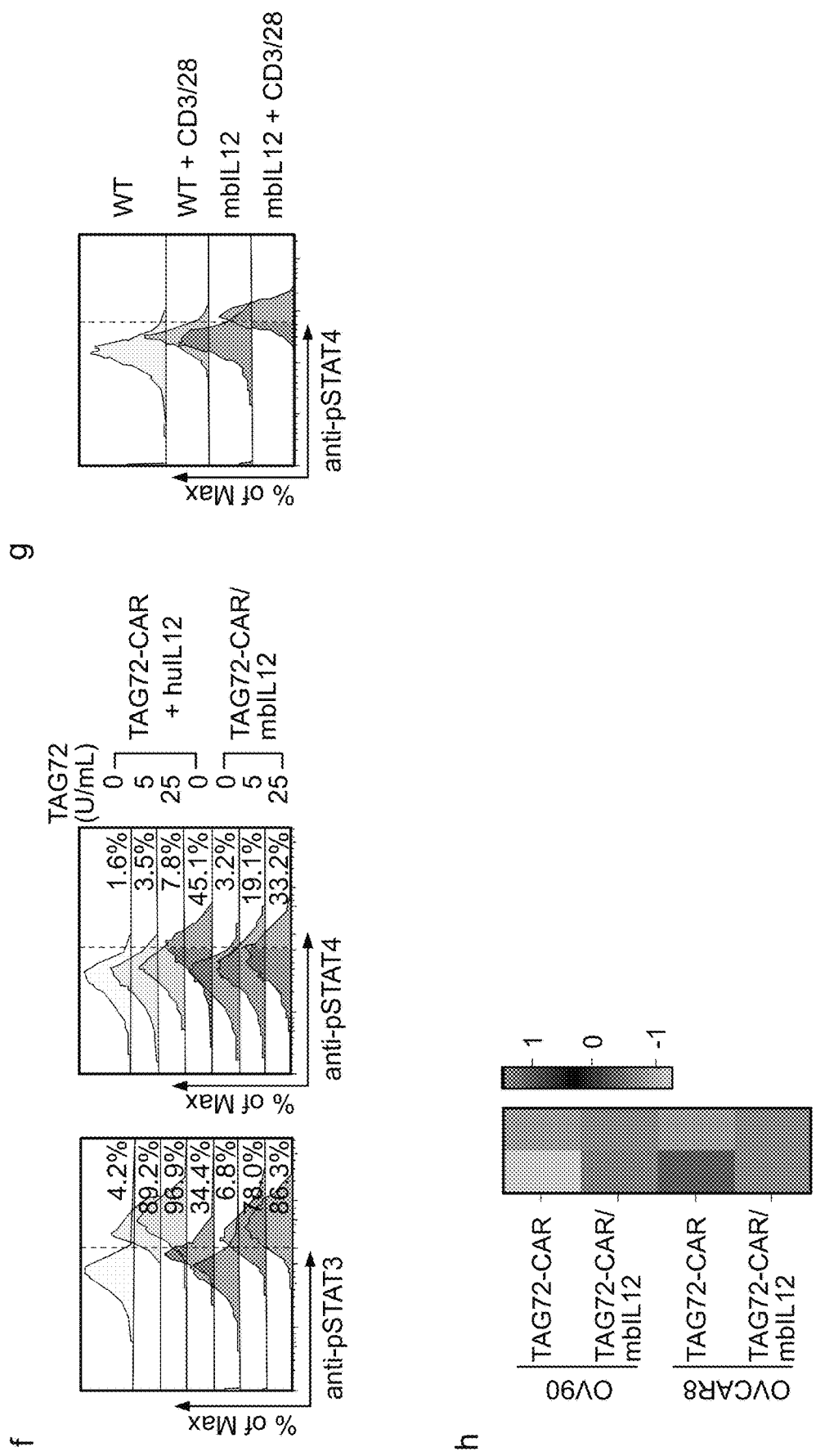

FIG. 10 Antigen-dependent IL-12 signaling in TAG72-CAR T cells. (a) Intracellular flow cytometric analysis of phosphorylated STAT4 (pSTAT4, pY693) in response to TAG72 and/or recombinant huIL12 (10 ng/mL) at indicated timepoints. (b) Quantification of pSTAT4 in (a). (c) Flow cytometric analysis of surface expression of mbIL12 on TAG72-CAR T cells stimulated with plate-bound TAG72 (100 U/mL) or control antigen (PSCA, 2.5 ug/mL). (d) Flow cytometric analysis of surface or intracellular expression of mbIL12 in TAG72-CAR T cells stimulates with varying concentrations of plate-bound TAG72. (e) Flow cytometric analysis of surface expression of mbIL12 on total, or gated on CD137+ or CD137− populations, of TAG72-CAR T cells stimulated with plate-bound TAG72 (100 U/mL). Table inset: CD137+ expression on TAG72-CAR T cells following stimulation with varying concentrations of plate-bound TAG72. (f) Intracellular flow cytometric analysis of phosphorylated STAT3 (pSTAT3, pY705) (left) and pSTAT4 (right) in TAG72-CAR and TAG72-CAR/mbIL12 T cells stimulated with varying concentrations of plate-bound TAG72 or recombinant huIL12 (10 ng/mL). (g) Intracellular flow cytometric analysis of pSTAT4 in TAG72-CAR T cells cocultured with HT1080 (TAG72−) cells transduced with mbIL12. Cells were stimulated with Immunocult CD3/CD28 per manufacturer recommendation. Cells were gated on CAR T cells and evaluated for pSTAT4. (h) mRNA levels of IL-12 in TAG72-CAR and TAG72-CAR/mbIL12 T cells stimulated with TAG72− OVCAR8 or TAG72+OV90 tumors overnight prior to RNA isolation and bulk RNAseq.

Figure 11:
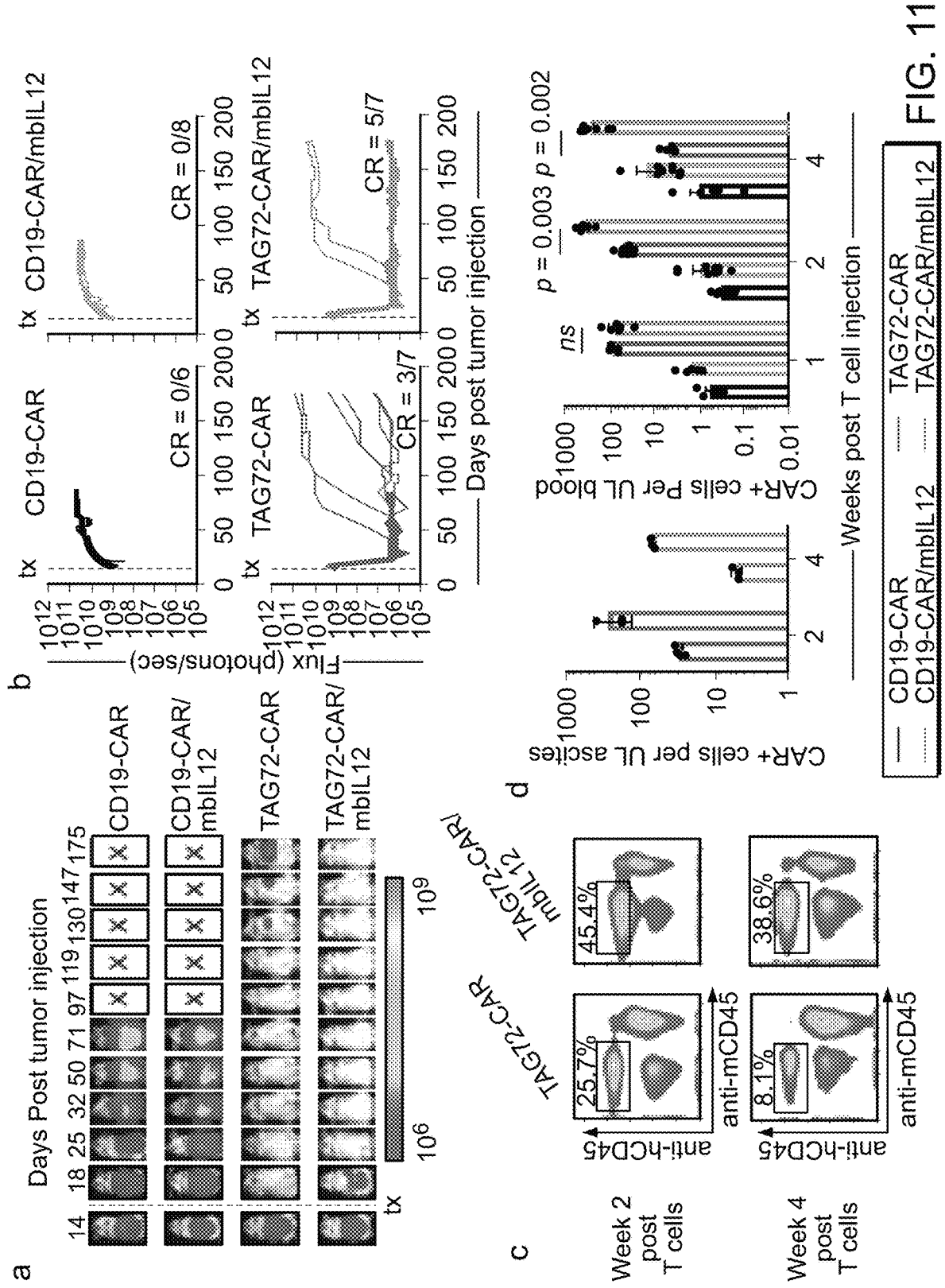
Figure 11:
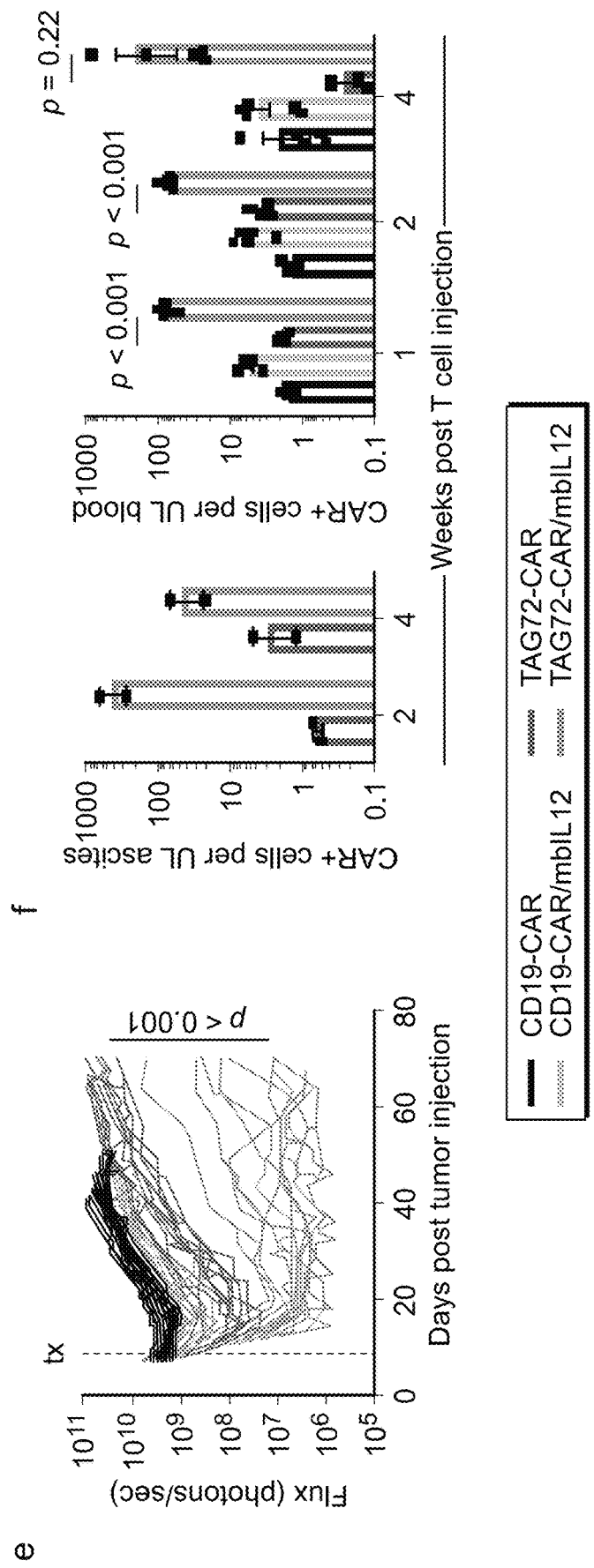

FIG. 11 Locoregional intraperitoneal delivery of TAG72-CAR/mbIL12 T cells reduces tumor burden and increases regional and systemic CAR T cell persistence in vivo. (a) Bioluminescent flux imaging of i.p. OVCAR3(eGFP/ffluc) tumor-bearing mice treated i.p. with CD19-CAR, CD19-CAR/mbIL12, TAG72-CAR or TAG72-CAR/mbIL12 T cells. (b) Quantification of flux (individual mice per group) from mice treated i.p. with CD19-CAR T cells (n=6/group), CD19-CAR/mbIL12 T cells (n=6/group), TAG72-CAR T cells (n=7/group) and TAG72-CAR/mbIL12 T cells (n=7/group). (c) Flow cytometric analysis of human CD45+ (hCD45) and mouse CD45+ (mCD45) cells in the peritoneal cavity of tumor-bearing mice at week 2 (top) or week 4 (bottom) post-treatment. (d) Quantification of TAG72-CAR T cells per uL of peritoneal ascites (left) at weeks 2 and 4 post-treatment. n=2 per group. Quantification of TAG72-CAR T cells per uL of peripheral blood (right) at weeks 1, 2, and 4 post-treatment. n=5/group. (e) Quantification of flux (individual mice per group) from OV90(eGFP/ffluc) tumor-bearing mice treated i.p. with CD19-CAR T cells (n=5/group), CD19-CAR/mbIL12 T cells (n=5/group), TAG72-CAR T cells (n=9-10/group) and TAG72-CAR/mbIL12 T cells (n=9-10/group). Combined data are from two independent studies. (f) Quantification of TAG72-CAR T cells per uL of peritoneal ascites (left) at weeks 2 and 4 post-treatment. n=2 per group. Quantification of TAG72-CAR T cells per uL of peripheral blood (right) at weeks 1, 2, and 4 post-treatment. n=5/group.

Figure 12:
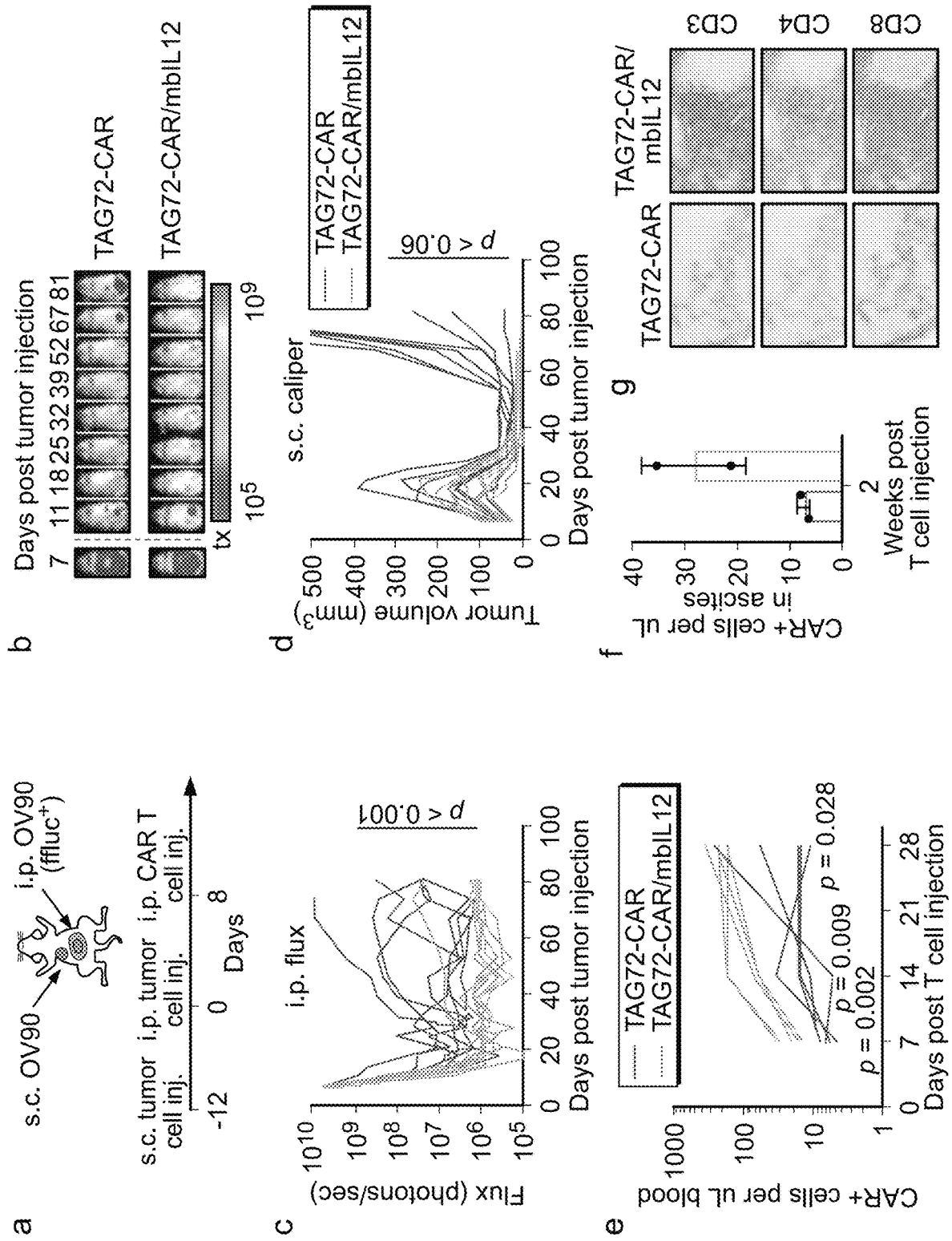

FIG. 12 Locoregional intraperitoneal delivery of TAG72-CAR/mbIL12 T cells eradicate subcutaneous tumors in dual tumor-bearing mice. (a) Schematic for subcutaneous (s.c.) and i.p. OV90 dual tumor model and treatment. (b) Bioluminescent flux imaging of dual tumor-bearing mice treated i.p. with TAG72-CAR or TAG72-CAR/mbIL12 T cells. (c) Quantification of flux (individual mice per group) from mice treated i.p. with TAG72-CAR T cells (n=8/group) and TAG72-CAR/mbIL12 T cells (n=8/group). (d) Quantification of subcutaneous tumor volume (individual mice per group) from mice treated i.p. with TAG72-CAR T cells. (e) Quantification of TAG72-CAR T cells per uL of peripheral blood at days 7, 14, 21, and 28 post-treatment. n=5/group. (f) Quantification of TAG72-CAR T cells per uL of peritoneal ascites at week 2 post-treatment. n=2/group. (g) Immunohistochemistry analysis of CD3+ T cells in s.c. tumors at day #post-treatment.

Figure 13:
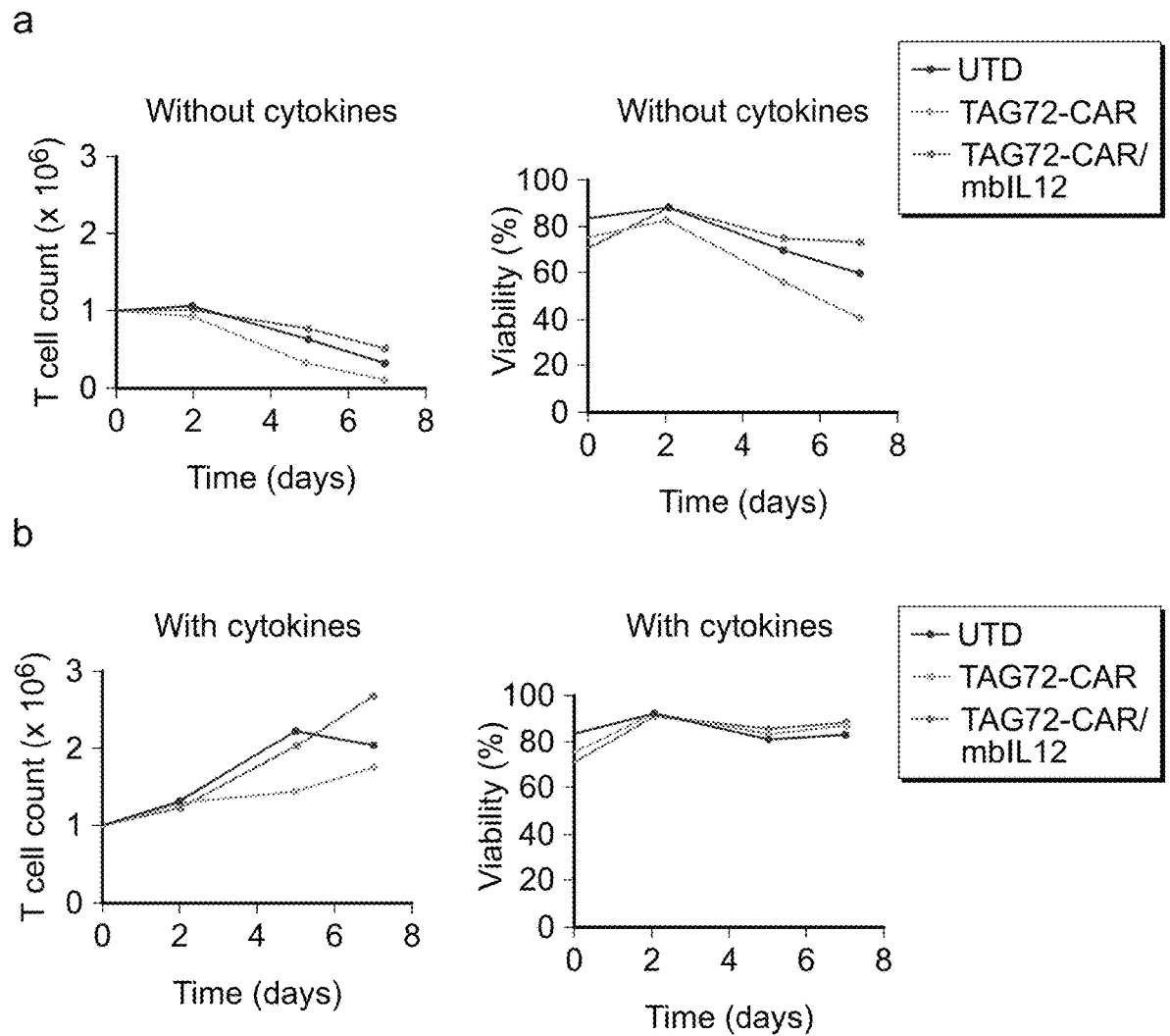

FIG. 13 mbIL-12 expressing TAG72-CAR T cells do not expand and survive in the absence of exogenous cytokines. (a-b) Quantification of T cell count (left) and percentage of viable cells (right) during ex vivo culture in the absence (a) or presence (b) of exogenous cytokines as described in Materials and Methods.

Figure 14:
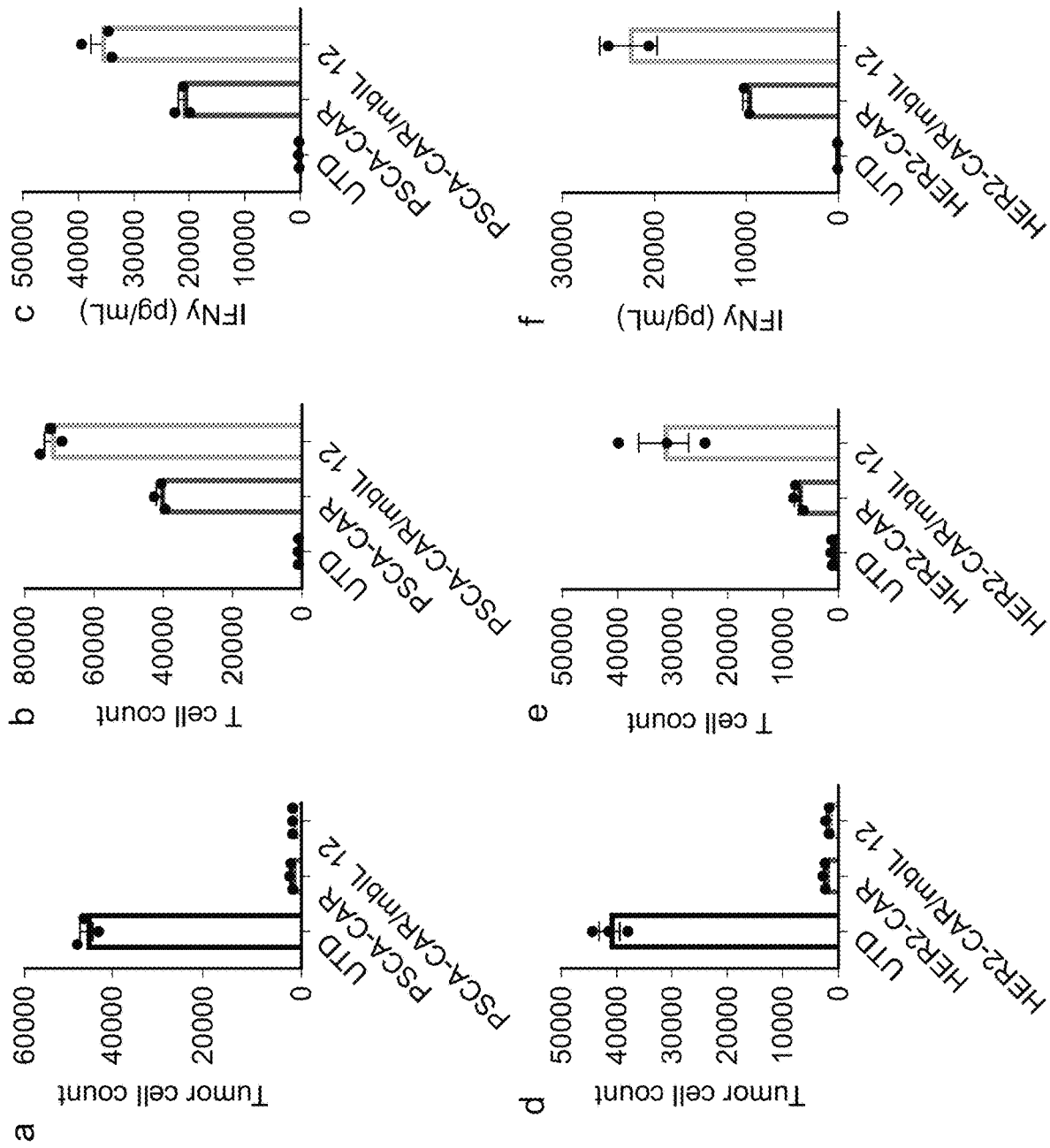
Figure 14:
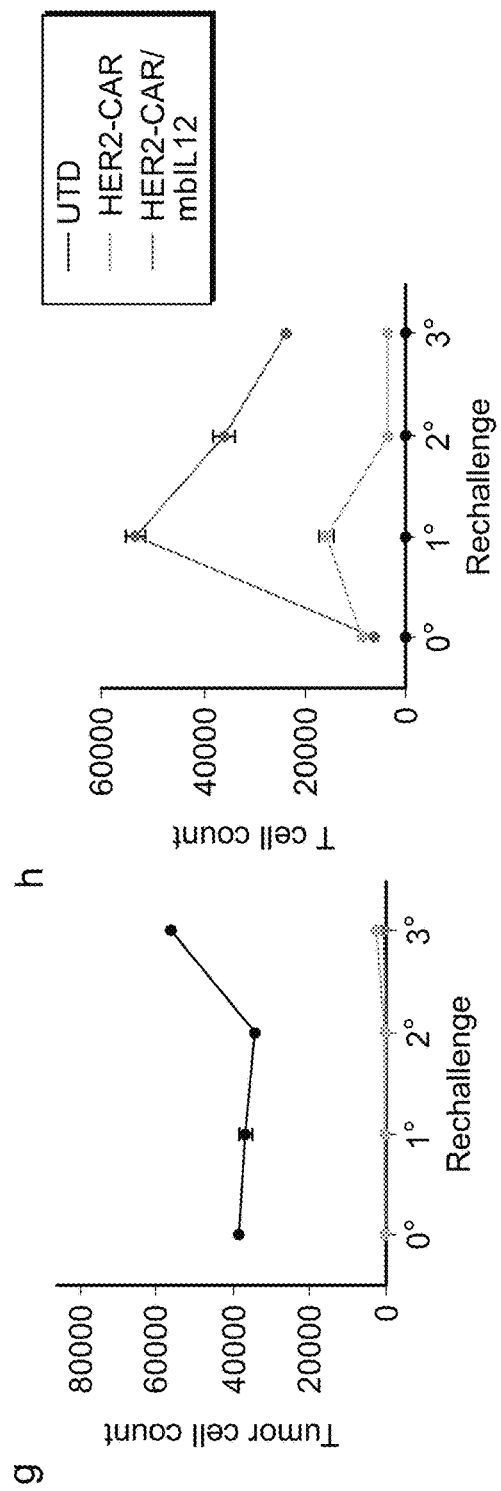
Figure 14:
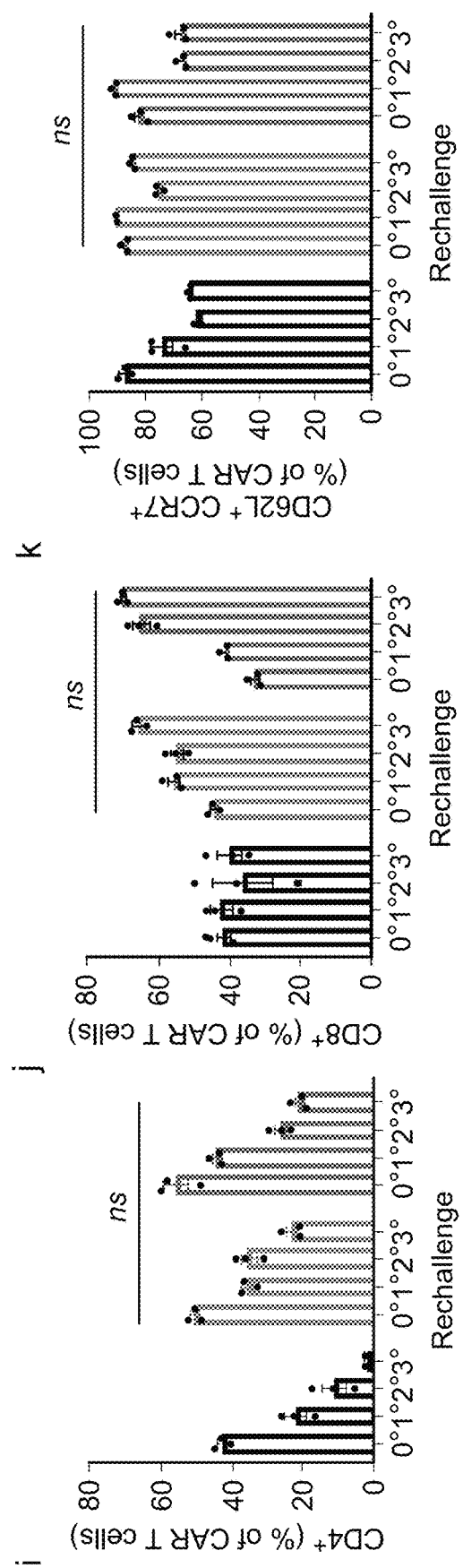

FIG. 14 mbIL-12 signaling improves in vitro functionality of PSCA- and HER2-CAR T cells. (a-f) Quantification of tumor cells (left), T cells (middle), and IFNγ levels in supernatant (right) for PSCA-CAR T cells (a-c) and HER2-CAR T cells (d-f), following co-culture with antigen-positive targets (PC3-PSCA or 468-HER2) at an E:T ratio of 1:10 for 6 days. (g) HER2-CAR T cells with or without mbIL12 were co-cultured with 468-HER2 cells (E:T=1:10) and rechallenged with 468-HER2 cells every three days. Remaining viable tumor cells (g) and T cells (h) were quantified by flow cytometry prior to every rechallenge and two or three days after the last rechallenge with 468-HER2 cells. Percentage of (i-k) CD4+ (i), CD8+(j), and CD62L$^+$CCR7$^+$ T cells were measured by flow cytometry from the rechallenge assay.

Figure 15:
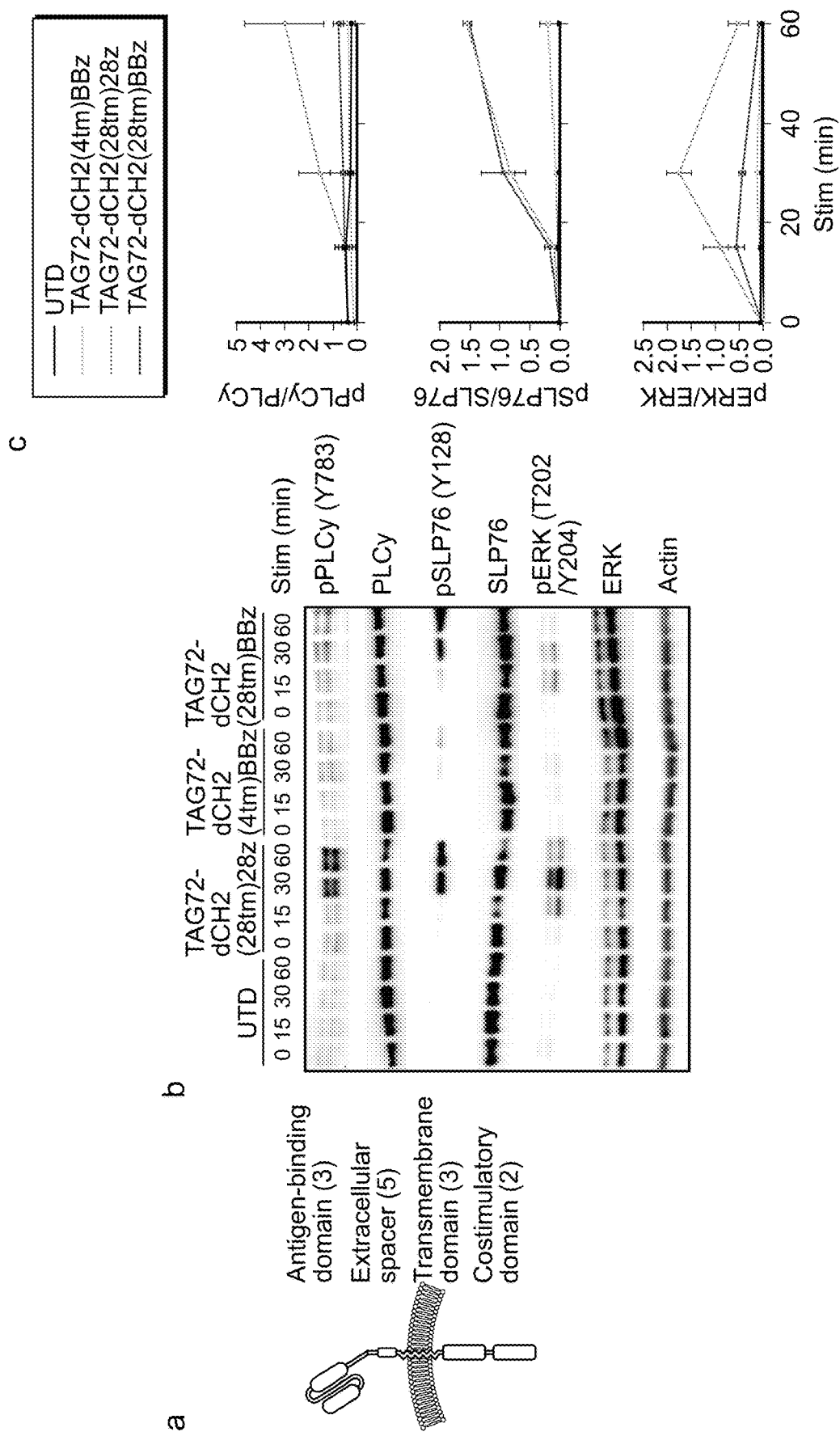

FIG. 15 TAG72-dCH2(CD28tm)BBz CAR shows comparable pSLP76 expression, but damped pPLCγ and pERK signaling compared to an otherwise identical TAG72 CAR with a CD28 costimulatory domain. (a-c)

Figure 16:
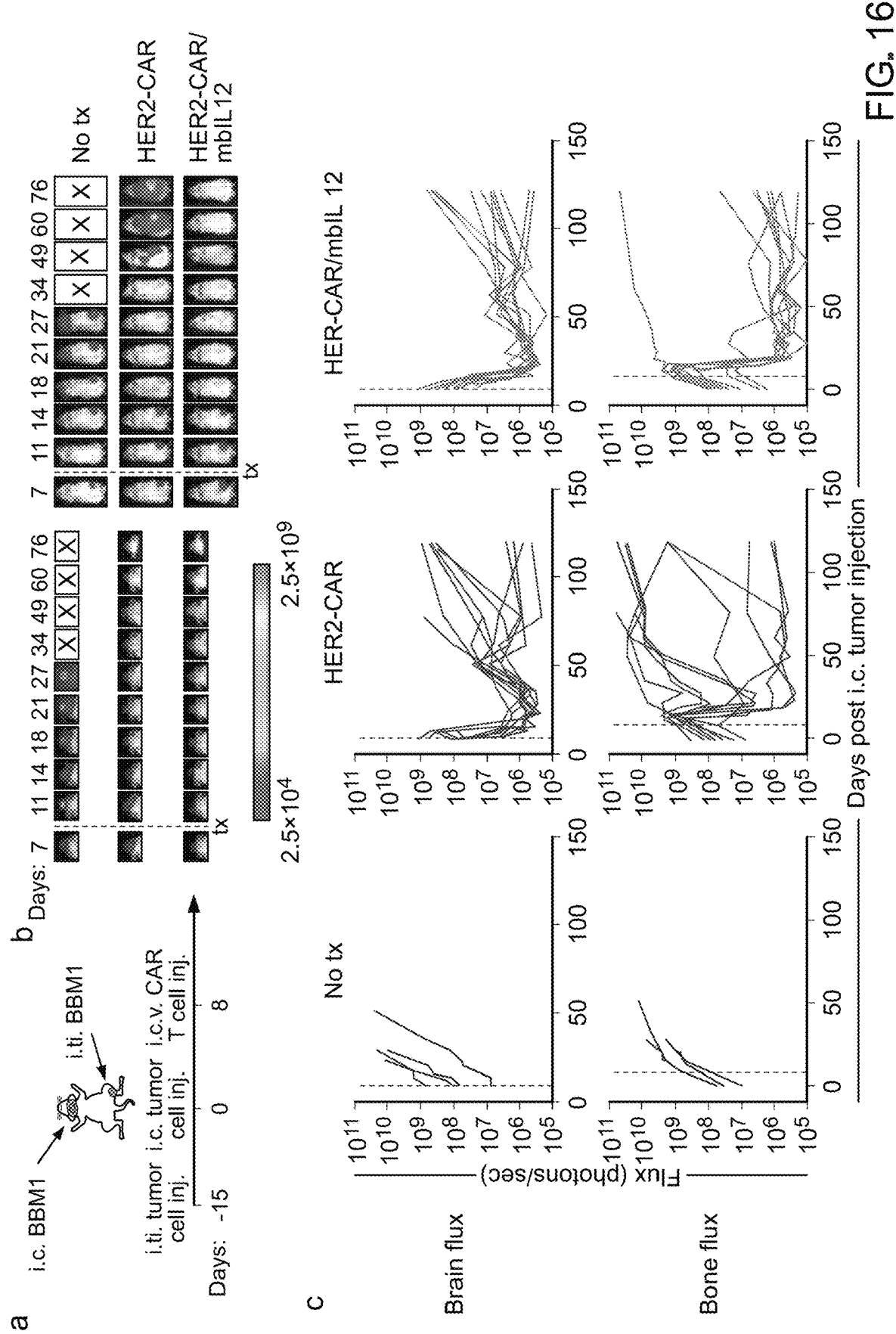
Figure 16:
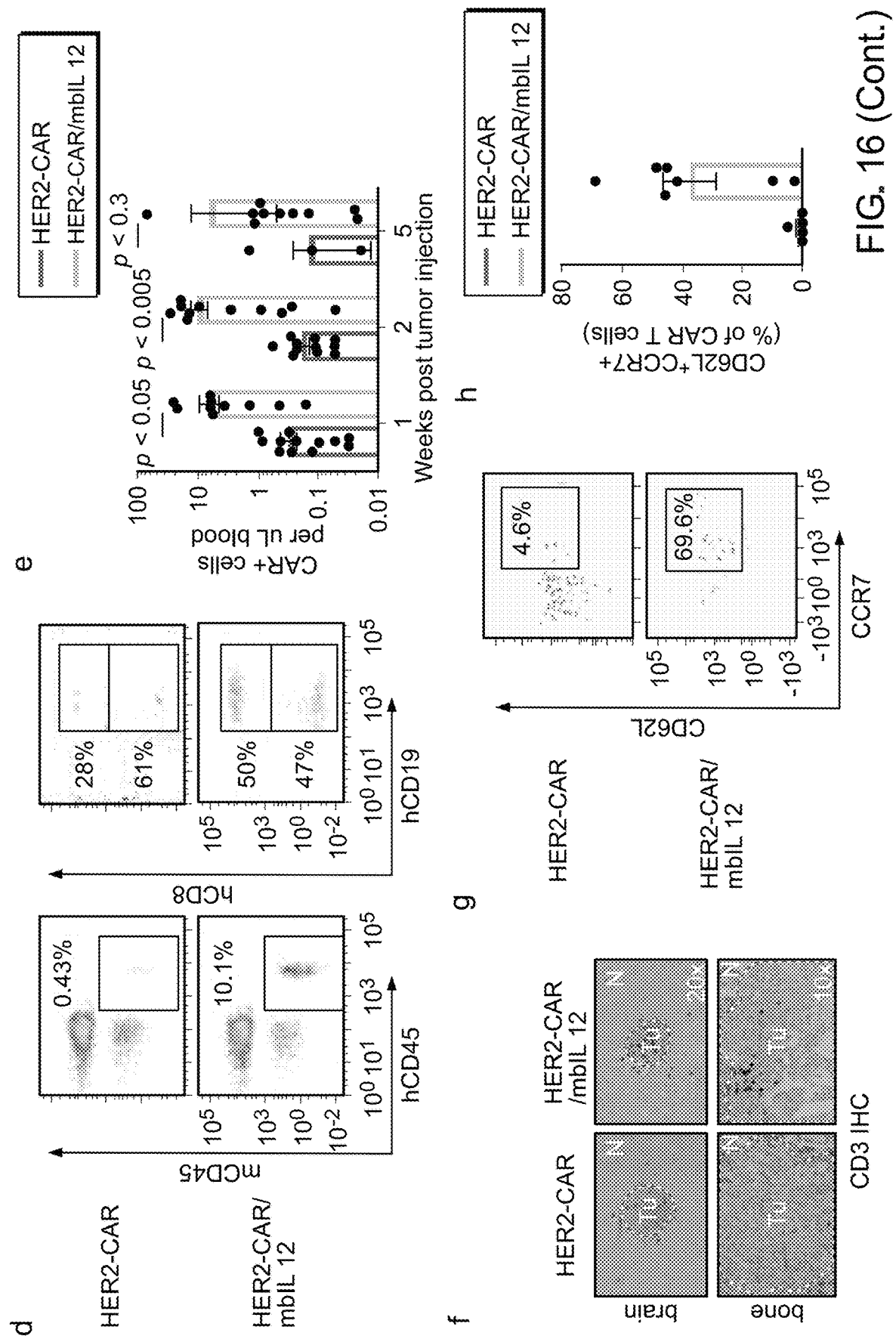
Figure 16:
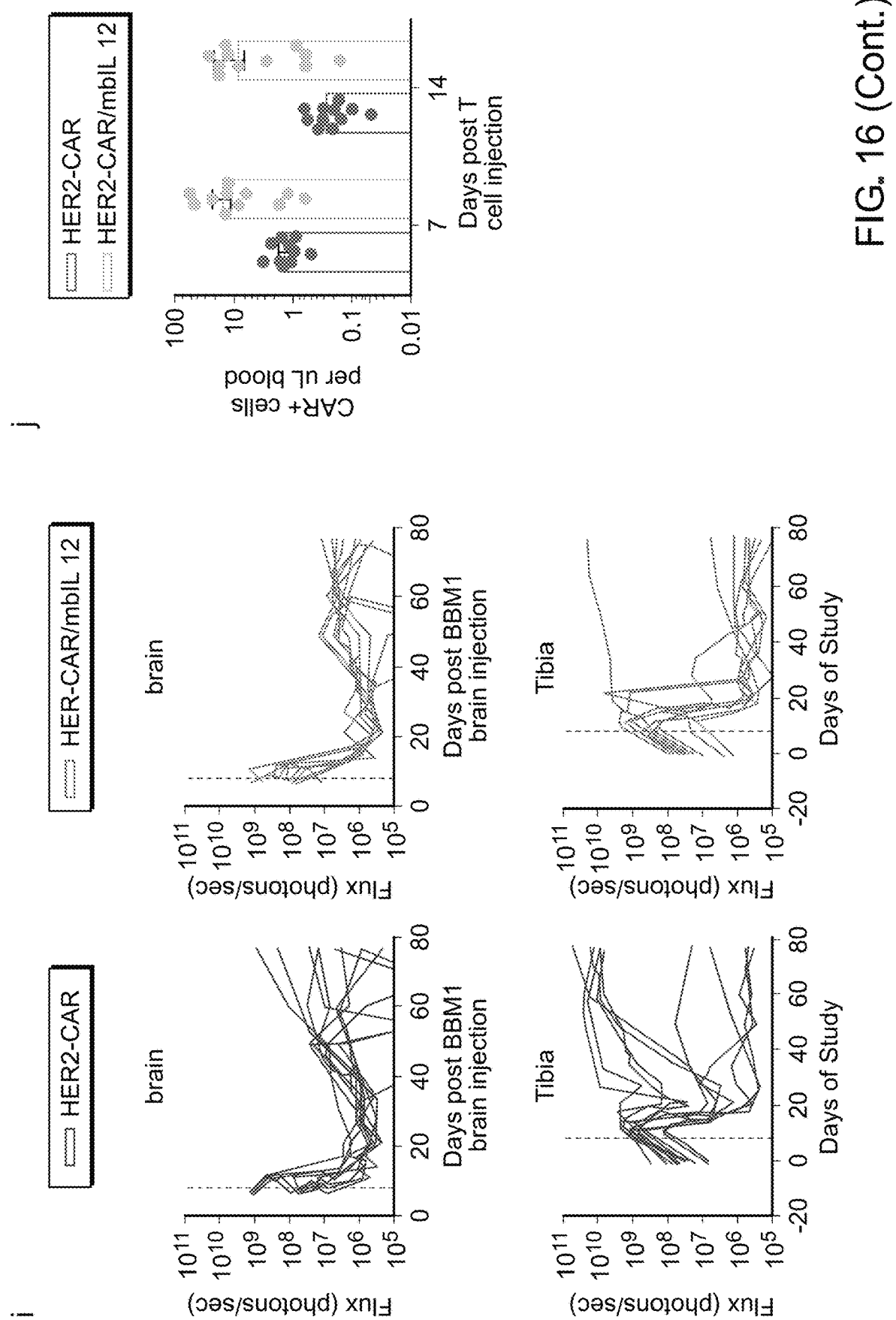

FIG. 16 mbIL-12 improves in vivo regional brain and systemic bone metastatic disease targeting by HER2 CAR. Locoregional intracerebroventricular delivery of HER2-CAR/mbIL12 T cells reduces tumor burden and increases regional and systemic CAR T cell persistence in vivo. (a) Schematic for intratibial (i.ti.) and intracranial (i.c.) BBM1 dual tumor model and treatment. (b) Bioluminescent flux imaging of dual tumor-bearing mice left untreated (no tx), or treated by intracerebroventricular (i.c.v.) injection of HER2-CAR or HER2-CAR/mbIL12 T cells. (c) Quantification of brain (top) or bone (bottom) flux from individual mice treated i.c.v. with HER2− CAR T cells (n>10/group), HER2−CAR/mbIL12 T cells (n>10/group), or no tx (n=4/group). (d-e) Representative flow cytometric analysis (d)

and quantification (e) of HER2-CAR T cells per uL of blood at weeks 1, 2, and 5 post-treatment. n>3/group. (f) Immunohistochemistry of CD3+ T cells in i.ti. and i.e. tumors at day 7 post-treatment. (g-h) Increases in central memory CAR T cells in peripheral blood of HER2-CAR/mbIL12 T cell treated mice. (g) Flow cytometric analysis of the frequency of HER2-CAR and HER2-CAR/mbIL12 T cells in the peripheral blood (h) Quantification of CAR T cells per uL of peripheral blood at 35 days post-treatment. n=5-7/group. (i) Quantification of brain (top) or bone (bottom) flux from individual mice treated i.c.v. with HER2- CAR T cells (n>10/group), HER2-CAR/mbIL12 T cells (n>10/group). (j) Quantification of HER2-CAR T cells per uL of blood at weeks 1 and 2 weeks following treatment. n>3/group.

Figure 17:
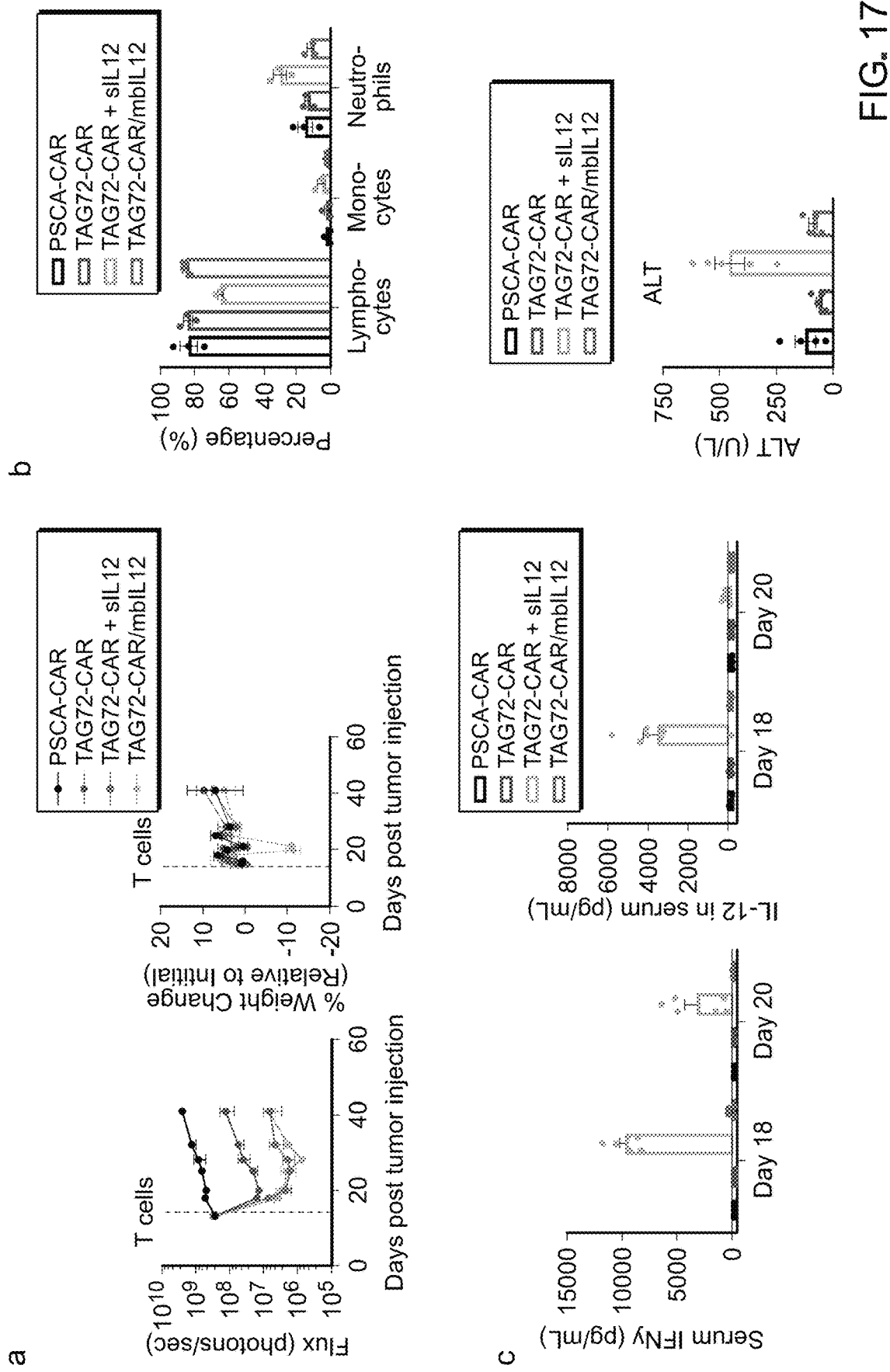

FIG. 17 mbIL-12 cytokine signaling in CAR T cells appears safer than recombinant IL-12 injection and demonstrates potent antitumor activity. (a-c) Locoregional intraperitoneal delivery of TAG72-CAR/mbIL12 T cells safely and effectively target ovarian cancer peritoneal metastasis in an immune-competent syngeneic mouse model. (a) Average tumor flux (left) and percent weight change (right) in indicated T cell treatments relative to pre-treatment weight (n>7/group). (b) Lymphocytes, monocytes, and neutrophils percentages from complete blood count analysis collected at 7 days post treatment (top), and quantification of serum levels of ALT (bottom) from mice at 6 days following treatment (n≥4/group). (c) ELISA quantification of IFNγ (left) and IL-12 (right) cytokines in mouse serum at day 18 and 20 (day 4 and 6 post-treatment respectively; n≥5/group).

Figure 18:
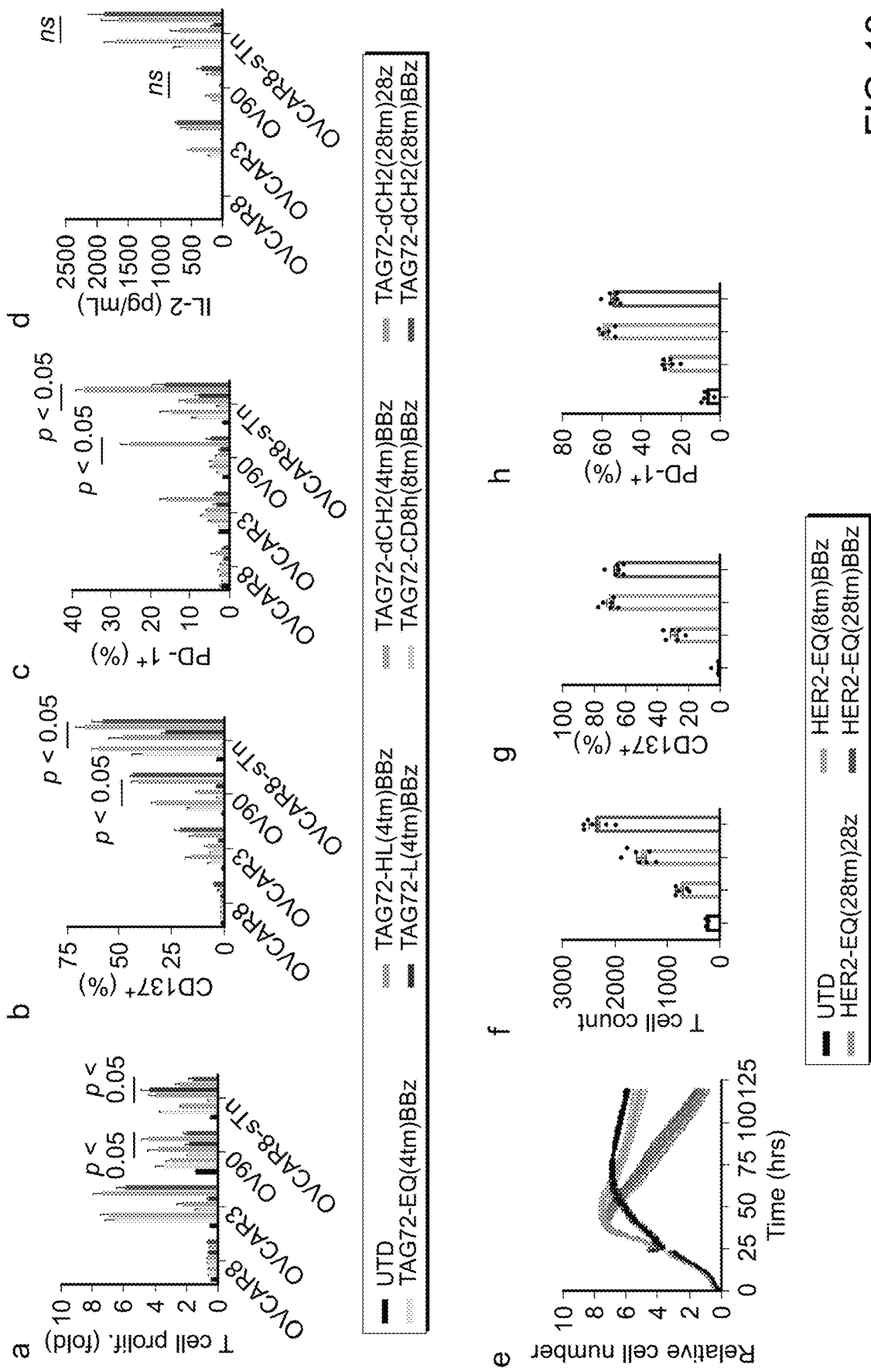

FIG. 18 In vitro analysis of CAR T cells with varying extracellular spacer, transmembrane and costimulatory domains. In vitro T cell proliferation in fold change compared to UTD (a) expression of CD137 (b) and PD-1 (c) by flow cytometry, and IL-2 production (d) by ELISA (c), of CAR T cells against tumor targets (TAG72- OVCAR8; TAG72+ OVCAR3, OV90, and OVCAR8-sTn) after 24 hr (for ELISA) or 72 hr of co-culture at an effector:target (E:T) ratio of 1:4, to support CAR T cell functional data in FIG. 1c-d. Statistical analysis reflects comparisons between TAG72-dCH2(28tm)28z and TAG72-dCH2(28tm)BBz. (e) HER2-CAR T cell killing of HER2$^+$ SKOV3 cells measured by xCELLigence over 5 days (E:T=1:20). Remaining T cells (f), along with expression of CD137 (g) and PD-1 (h) by flow cytometry.

Figure 19:
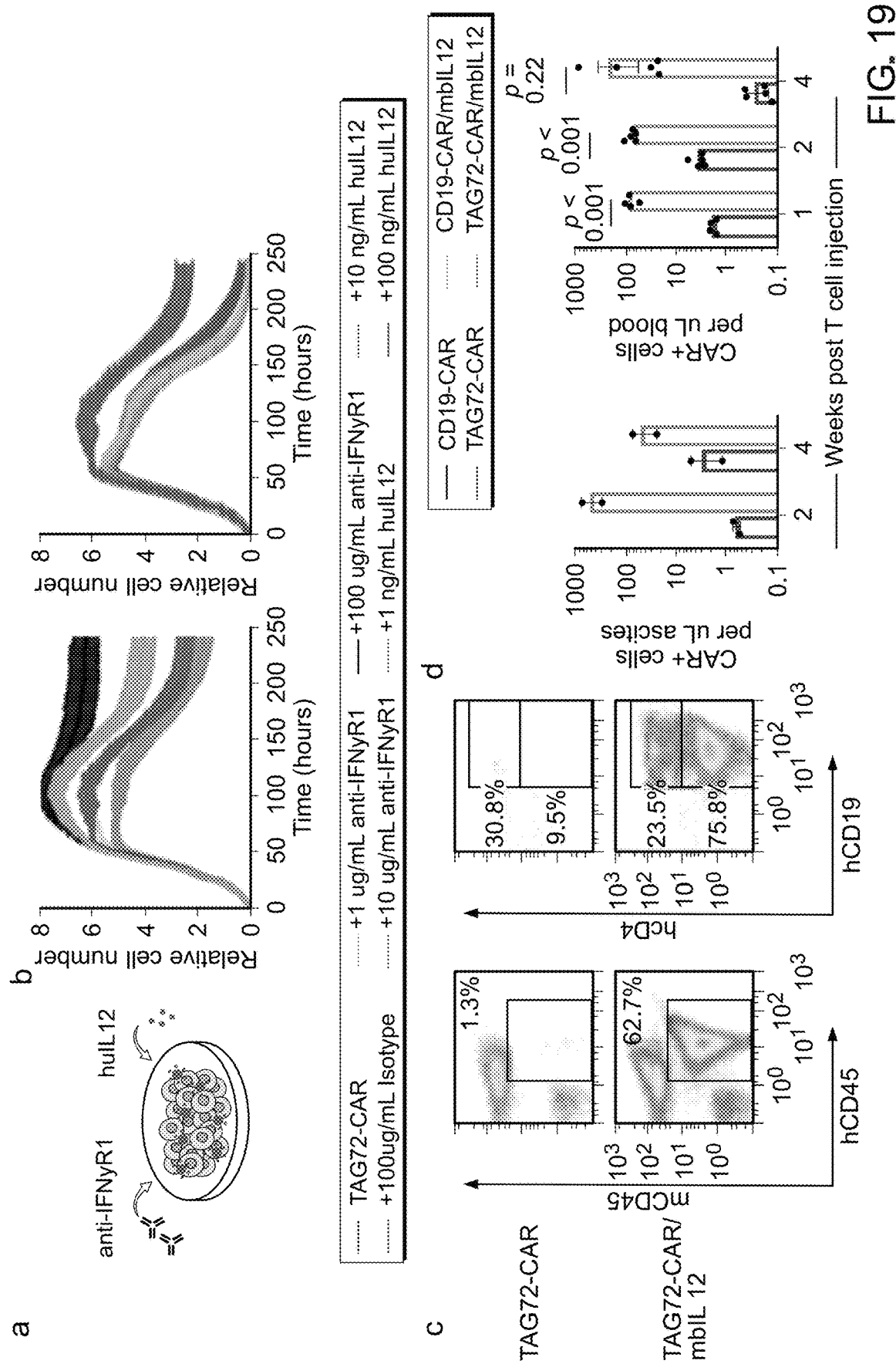

FIG. 19 Membrane-bound IL-12 engineered TAG72-CAR T cells induce higher IFNγ, T cell expansion, and anti-tumor activity in vitro. (a-b) Tumor cell killing of OV90 cells by TAG72- CAR T cells (E:T=1:20) with addition of varying concentrations of anti-IFNγR1 blocking antibody, isotype control, and recombinant human IL-12 cytokine measured by xCELLigence over 10 days (a-b). Locoregional intraperitoneal delivery of TAG72- CAR/mbIL12 T cells reduces tumor burden and increases regional and systemic CAR T cell persistence in vivo. The i.p. OV90(eGFP/ffluc) tumor-bearing mice treated 1018 i.p. with CD19-CAR, CD19-CAR/mbIL12, TAG72-CAR or TAG72-CAR/mbIL12 T cells. (c) Flow cytometric analysis of TAG72-CAR T cells per uL of peritoneal ascites. (d) Quantification of TAG72-CAR T cells per uL of peritoneal ascites (left) at weeks 2 and 4 post-treatment. n=2 per group. Quantification of TAG72-CAR T cells per uL of peripheral blood (right) at weeks 1, 2, and 4 post-treatment. n=5/group.

Figure 20:
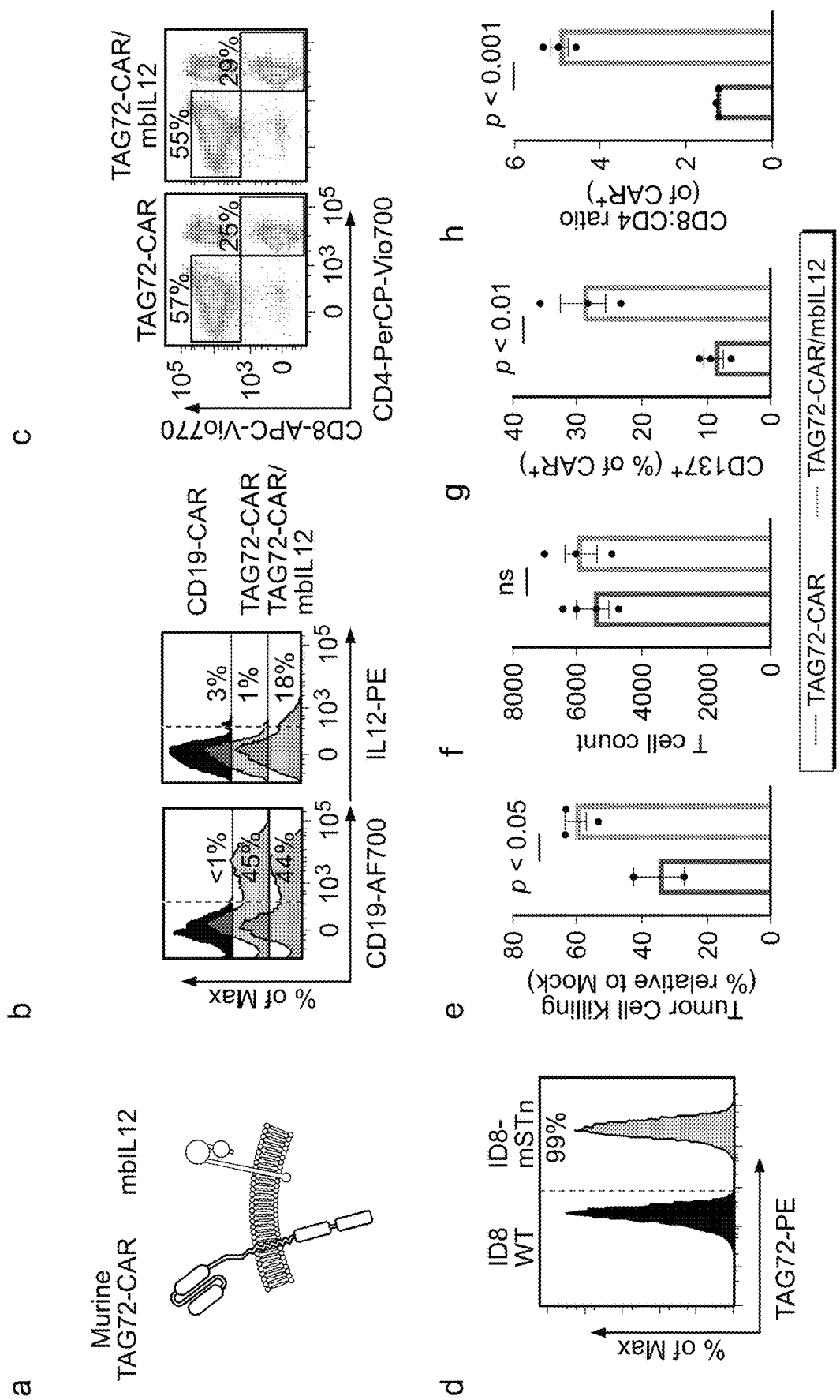

FIG. 20 Generation and functional characterization in vitro of murine TAG72-CAR expressing murine mbIL12. (a) Illustration of dual expression of murine TAG72-CAR and murine mbIL12 on mouse T cell surface. (b) Flow cytometric analysis of surface TAG72- CAR expression as detected by expression of truncated murine CD19t (left) and surface murine mbIL12 as detected by anti-mIL12 PE conjugated antibody. (c) Flow cytometric analysis of murine CD4 and CD8 ratios in TAG72-CAR and TAG72-CAR/mbIL12. (d-g) Functional characterization of 72-hour long term co-culture killing assay tumor killing (d) against ID80-mSTn tumor cells at 1:1 E:T (e), T cell counts (f), CAR T cell CD137 (g), and post co-culture CD8 and CD4 ratios (h) in TAG72-CAR vs. TAG72-CAR/mbIL12 T cells.

Figure 21:
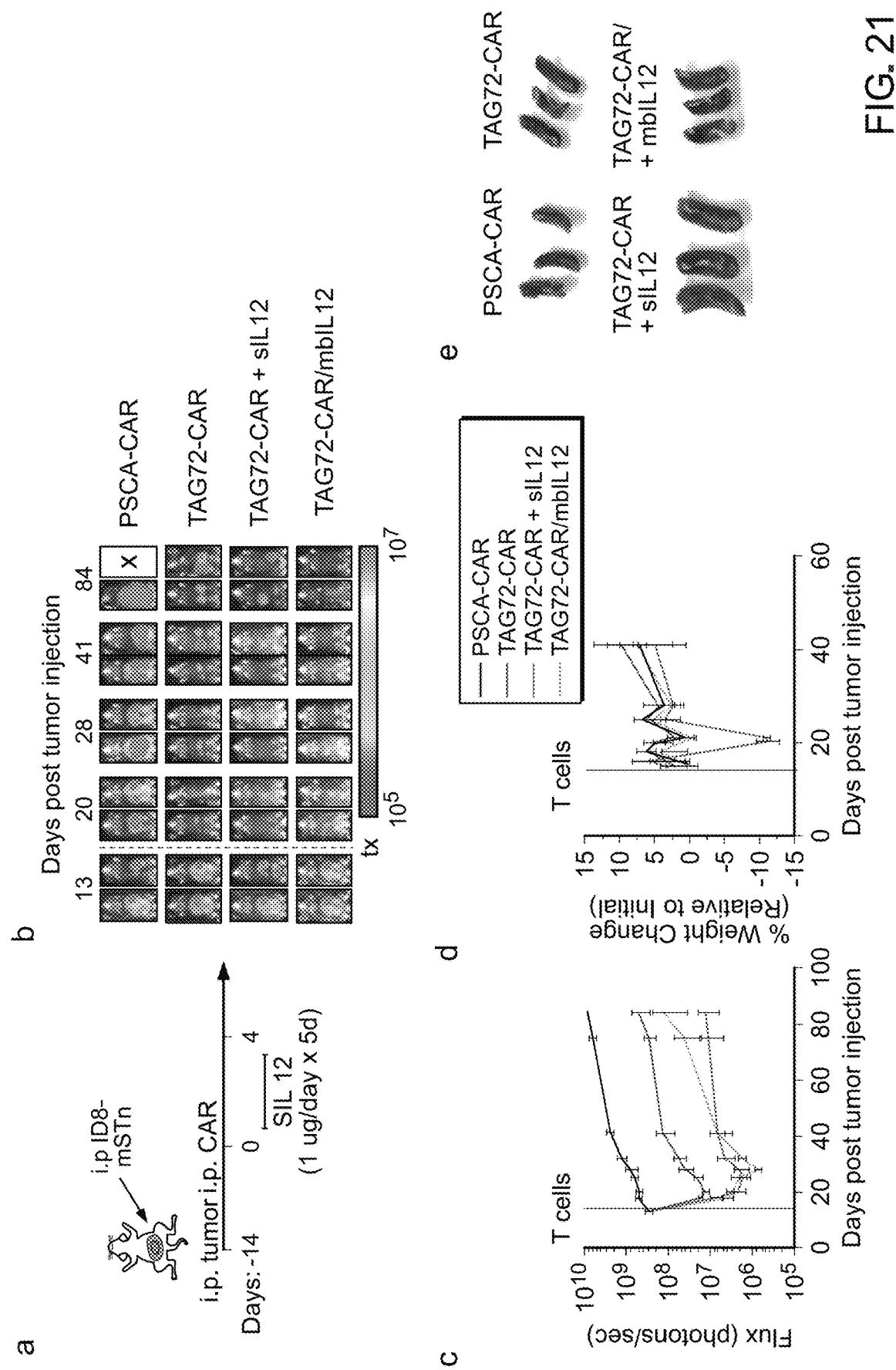
Figure 21:
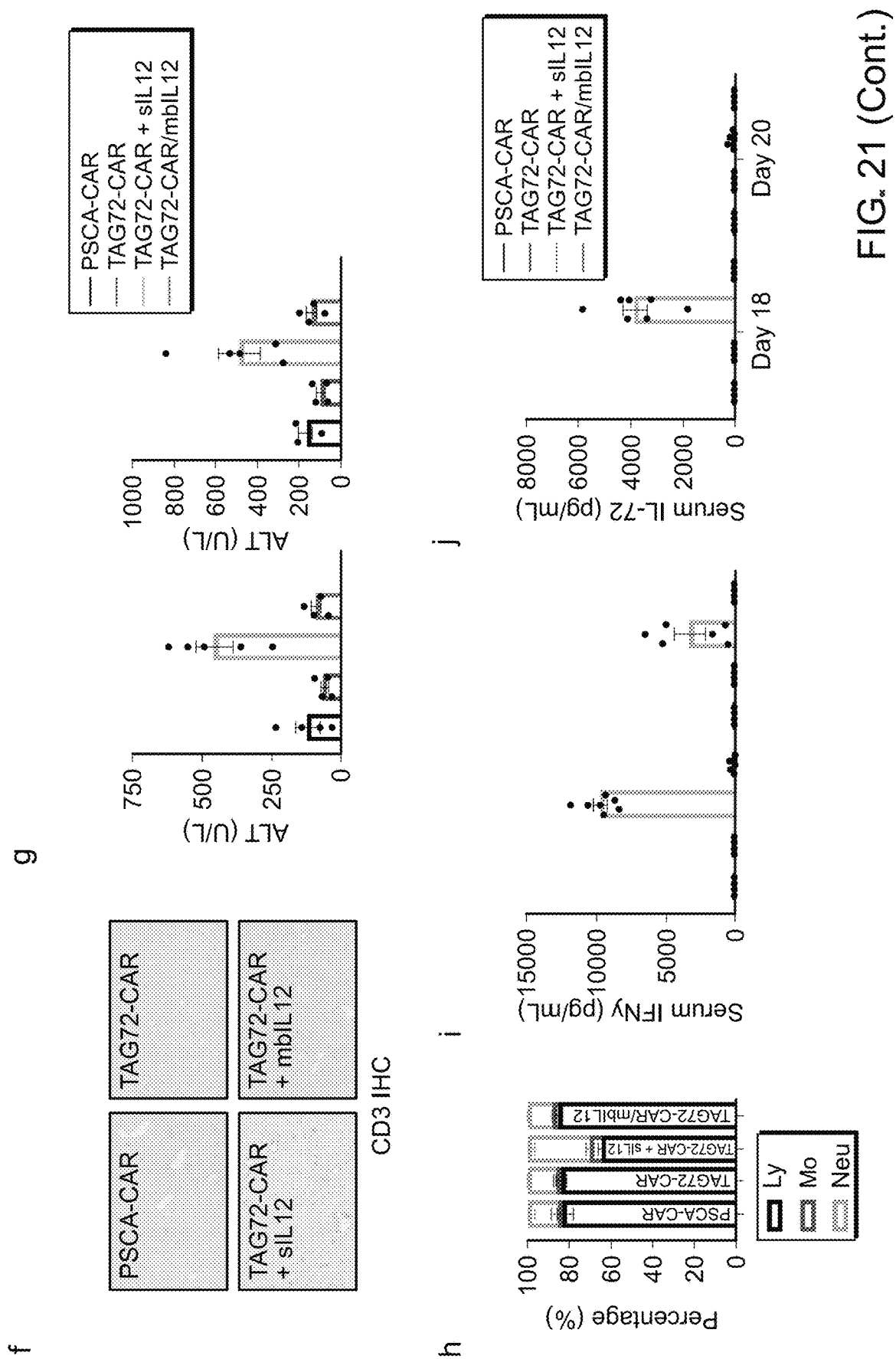
Figure 21:
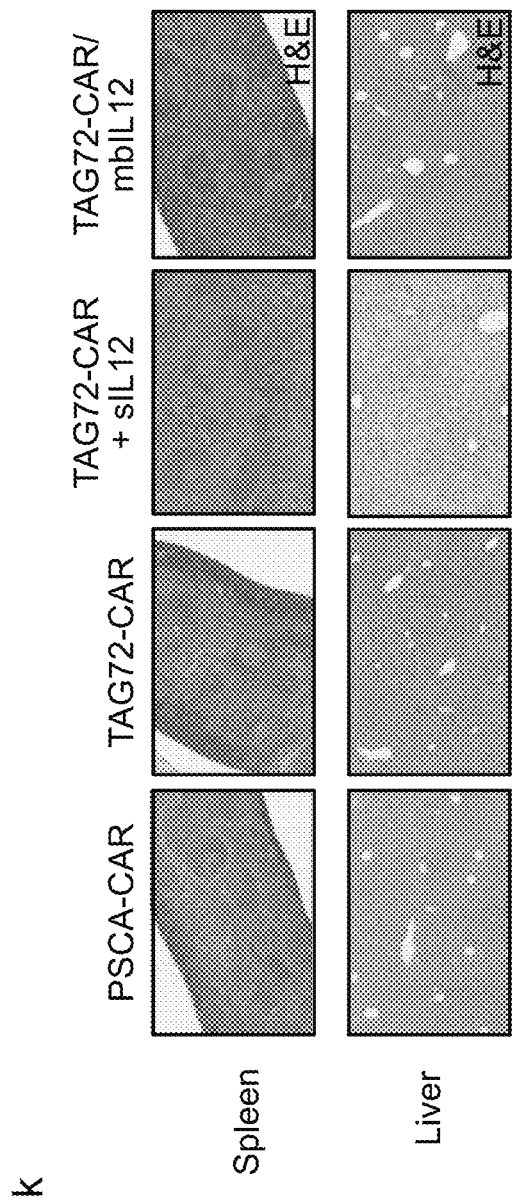

FIG. 21 Locoregional intraperitoneal delivery of TAG72-CAR/mbIL12 T cells safely and effectively target ovarian cancer peritoneal metastasis in an immune-competent syngeneic mouse model. (a) Schematic for intraperitoneal (i.p.) ID8-mSTn tumor model and treatment. (b) Bioluminescence flux imaging of tumor-bearing mice, treated by intraperitoneal (i.p.) injection of indicated T cells. (c) Average tumor flux and (d) percent weight change in indicated T cell treatments relative to pre-treatment weight (n>7/group). (e) Spleen photographs (n=3/group) and (f) CD3 IHC in livers harvested at 7 days post treatment. (g) Quantification of serum levels of ALT (left) and AST (right) from mice at 6 days post treatment (n≥4/group). (h) Percent lymphocytes, monocytes, and neutrophils from complete blood count analysis collected at 7 days post treatment. ELISA quantification of IFNγ (i) and IL-12 (j) cytokines in mouse serum at day 18 and 20 (day 4 and 6 post treatment respectively) post tumor injection (n≥5/group). (k) Systemic effects of sIL-12 and TAG72-CAR/mbIL12 T cells. H&E spleen and liver collected from i.p. ID8-mSTn tumor-bearing mice treated with indicated T cells.

Figure 22:
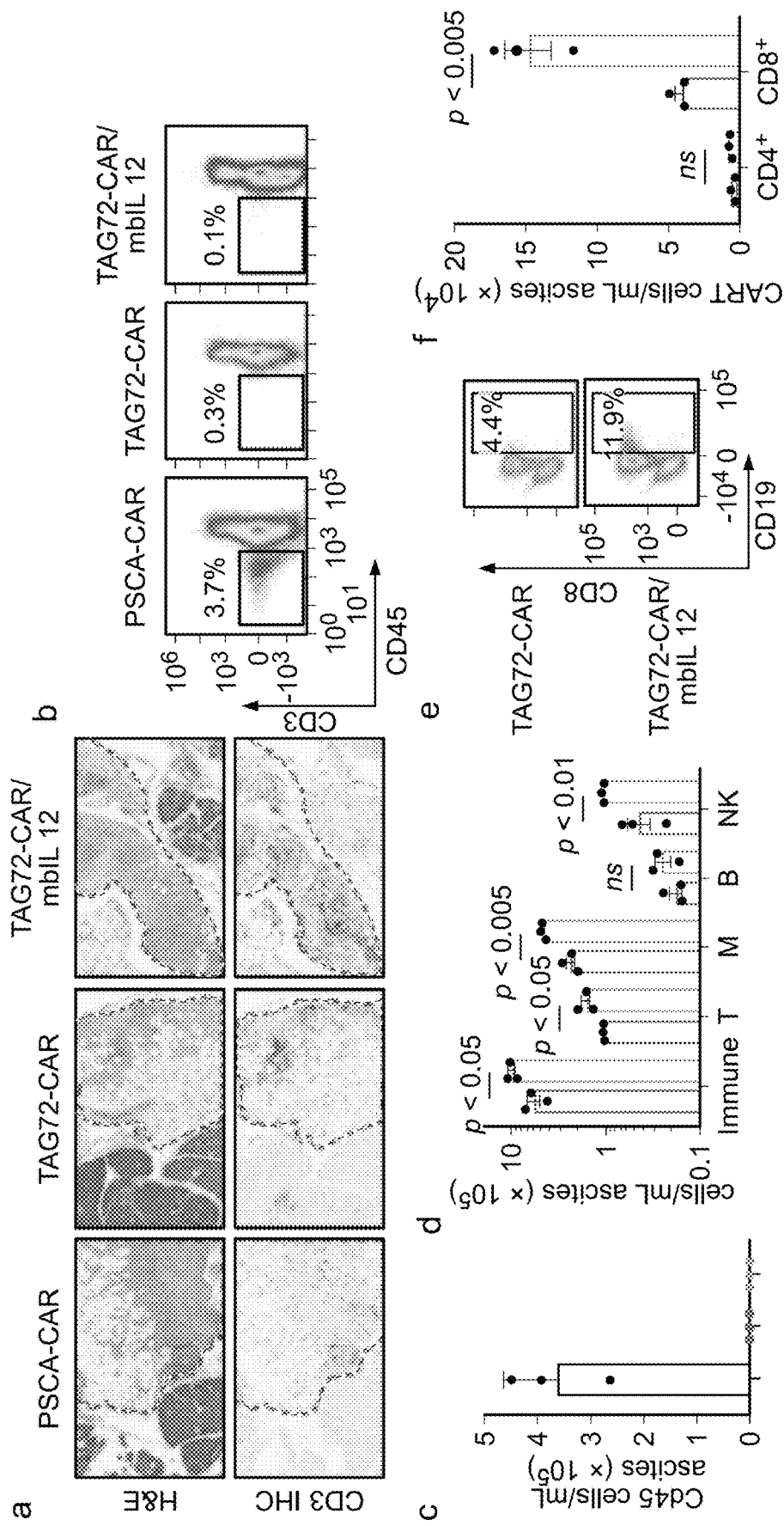
Figure 22:
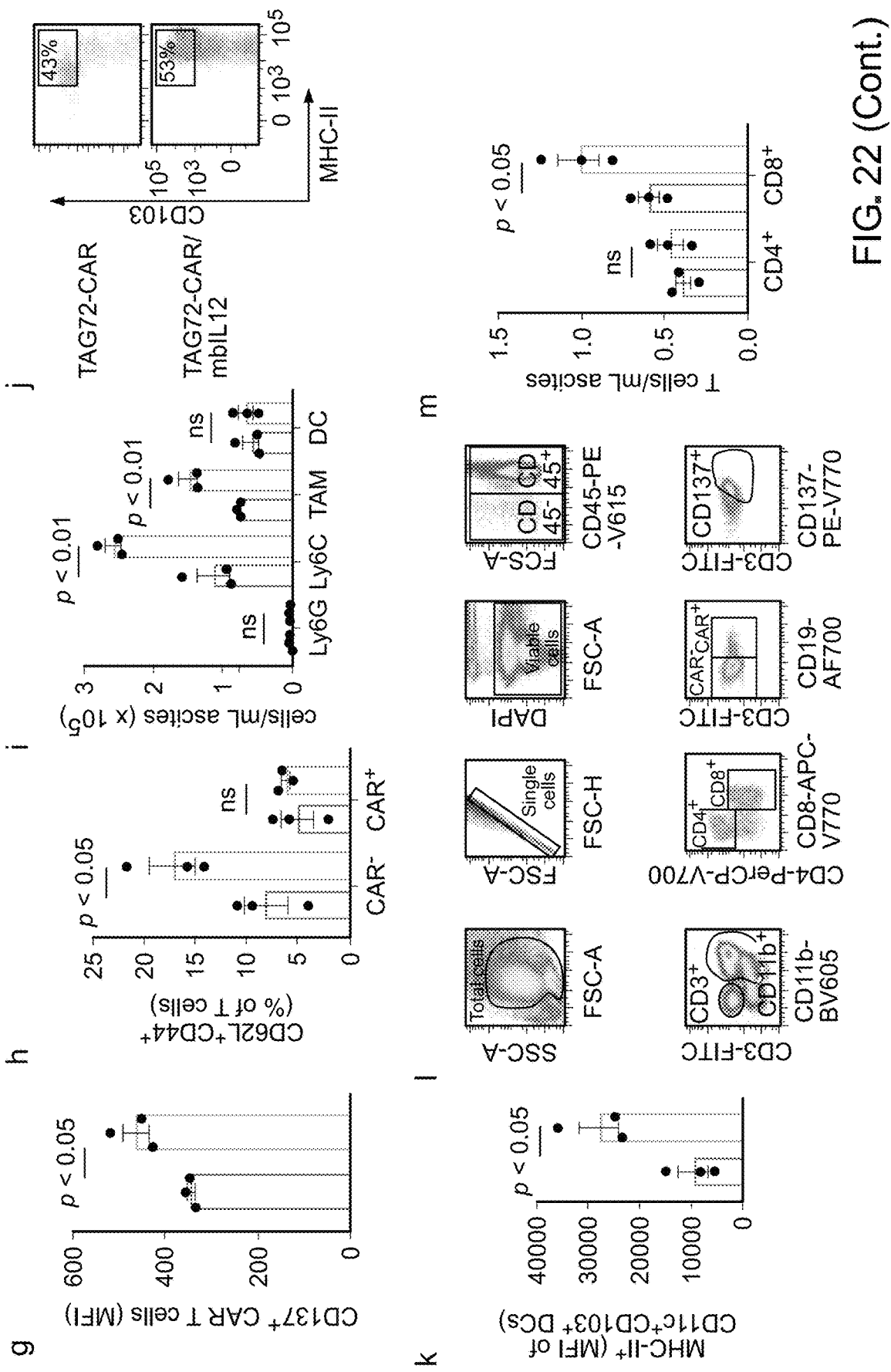

FIG. 22 TAG72-CAR/mbIL12 T cell therapy induces TME modifications in ovarian cancer peritoneal metastases in an immune-competent syngeneic mouse model. (a) H&E and CD3 IHC in solid tumor masses collected from the upper omental region of i.p. ID8-mSTn tumor-bearing mice treated with indicated T cells. (b) Flow cytometric analysis of tumor cells (CD3-CD45- double negative) in peritoneal ascites. (c) Quantification of tumor cells (CD3-CD45- double negative) and (d) immune subsets (CD45+, CD3+, CD11b+ and NK+) as cells/mL in peritoneal ascites. (e) Flow cytometric analysis of percent CAR T cells (CD3+ CD19t+) and (f) quantification counts of CD4+ and CD8+ CAR T cells/mL in peritoneal ascites. (g) Quantification of mean fluorescent intensity (MFI) of CD137+ in CAR T cells in peritoneal ascites. (h) Quantification of percent CD62L+ CD44+ (Tcm) in both CAR+ and CAR- T cells in peritoneal ascites. (i) Quantification of myeloid cell counts (Ly6G+, Ly6C+, Ly6G-/C- double negative tumor-associated macrophages (TAM) and CD11c+CD103+ dendritic cells (DC) as cells/mL in peritoneal ascites gated from total CD11b+ 1073 cells. Flow cytometry analysis of percent (j) and quantification of MFI (k) on CD103+MHC Class II+ double positive DC in peritoneal ascites. All analyses represent data collected from ascites of ID8-mSTn tumor-bearing mice at 7 days post treatment, n=3/group. (l) Flow cytometry gating strategy. (m) Total CD4+ and CD8+ T cells mL of peritoneal ascites.

Figure 23:
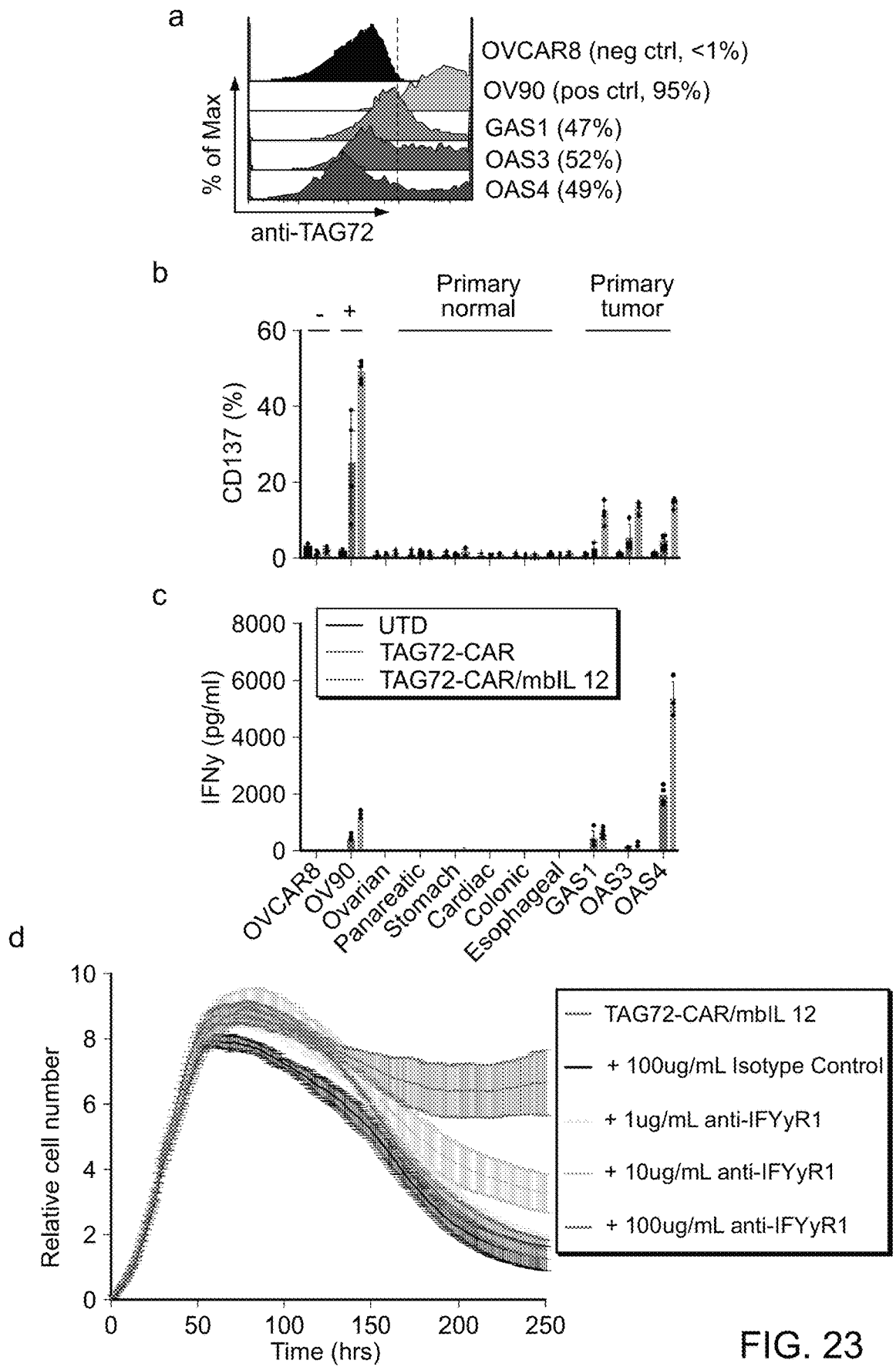

FIG. 23 In vitro safety of TAG72-CAR/mbIL12 T cells against normal human cell lines. (a) Flow cytometric analysis of TAG72 expression on the cell surface of TAG72-negative (OVCAR8) tumor cells, TAG72-positive (OV90) tumor cells, and indicated patient-derived gastric (GAS1) and ovarian (OAS3 and 4) peritoneal ascites. (b-c) TAG72-CAR T cells with or without mbIL12 were co-cultured with tumor and normal cell at 1:4 E:T ratio for 48 hours. (b) Quantification of CD137 expression in CAR T cells was measured by flow cytometry. (c) IFNγ levels in supernatant were quantified by ELISA. (d) IFNγ signaling drives anti-tumor activity in TAG72-CAR/mbIL12 T cells in vitro. Tumor cell killing of OV90 cells by TAG72- CAR/mbIL12 T cells (E:T=1:20) with addition of varying concentrations of anti-IFNγR1 blocking antibody or isotype by xCELLigence over 10 days.

DETAILED DESCRIPTION

Membrane Bound IL-12

The membrane bound IL-12 include a human CD28 transmembrane domain that is important for providing membrane bound IL-12 with ability to improve the function of CAR T cells. Thus, mb(28)IL-12 includes, from amino to carboxy terminus: mature human IL-12 beta (p40) subunit, an optional first peptide linker, mature human IL-12 alpha (p35) subunit, an optional second peptide linker, human CD28 transmembrane domain. In some embodiments, all or a portion of the cytoplasmic domain of human CD28 follows the transmembrane domain. A signal sequence can precede the human Il-12 beta subunit.

The p40 subunit portion comprises or consists of the sequence:

(SEQ ID NO: 1)
IWELKKDVYVVELDWYPDAPGEMVVLTCDTPEEDGITWTLDQSSE

VLGSGKTLTIQVKEFGDAGQYTCHKGGEVLSHSLLLLHKKEDGIW

STDILKDQKEPKNKTFLRCEAKNYSGRFTCWWLTTISTDLTFSVK

SSRGSSDPQGVTCGAATLSAERVRGDNKEYEYSVECQEDSACPAA

EESLPIEVMVDAVHKLKYENYTSSFFIRDIIKPDPPKNLQLKPLK

NSRQVEVSWEYPDTWSTPHSYFSLTFCVQVQGKSKREKKDRVFTD

KTSATVICRKNASISVRAQDRYYSSSWSEWASVPCS

The first peptide linker comprises or consists of, for example, the sequence (SEQ ID NO: 4)
VPGVGVPGVG The p35 subunit portion comprises or consists of the sequence:

(SEQ ID NO: 2)
ARNLPVATPDPGMFPCLHHSQNLLRAVSNMLQKARQTLEFYPCTS

EEIDHEDITKDKTSTVEACLPLELTKNESCLNSRETSFITNGSCL

ASRKTSFMMALCLSSIYEDSKMYQVEFKTMNAKLLMDPKRQIFLD

QNMLAVIDELMQALNFNSETVPQKSSLEEPDFYKTKIKLCILLHA

FRIRAVTIDRVMSYLNAS

The p35 subunit portion comprises or consists of the sequence:

(SEQ ID NO: 3)
ARNLPVATPDPGMFPCLHHSQNLLRAVSNMLQKARQTLEFYPCTSEEID

HEDITKDKTSTVEACLPLELTKNESCLNSRETSFITNGSCLASRKTSFM

MALCLSSIYEDLKMYQVEFKTMNAKLLMDPKRQIFLDQNMLAVIDELMQ

ALNFNSETVPQKSSLEEPDFYKTKIKLCILLHAFRIRAVTIDRVMSYLN

AS

The second peptide linker comprises or consists of, for example, the sequence:

GGG

The human CD28 transmembrane domain comprises or consists of the sequence:

(SEQ ID NO: 16)
FWVLVVVGGVLACYSLLVTVAFIIFWV.

The human CD28 cytoplasmic domain portion comprises or consists of the sequence:

(SEQ ID NO: 5)
RSKR

A human CD28 transmembrane domain that includes a portion of the human CD28 cytoplasmic domain can comprise or consist of the sequence:

(SEQ ID NO: 76)
FWVLVVVGGVLACYSLLVTVAFIIFWVRSKR.

Mature mb(28)IL-12 can comprise or consist of the sequence:

(SEQ ID NO: 6)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS<u>VPGVGVPGVG</u>ARNLPVATPDPGMFPCLHHSQNLLRAV

SNMLQKARQTLEFYPCTSEEIDHEDITKDKTSTVEACLPLELTKNESCL

NSRETSFITNGSCLASRKTSFMMALCLSSIYEDSKMYQVEFKTMNAKLL

MDPKRQIFLDQNMLAVIDELMQALNFNSETVPQKSSLEEPDFYKTKIKL

CILLHAFRIRAVTIDRVMSYLNAS<u>GGG</u>FWVLVVVGGVLACYSLLVTVAF

IIFWV<u>RSKR</u>

Mature mb(28)IL-12 can comprise or consist of the sequence:

(SEQ ID NO: 7)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

-continued
KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS<u>VPGVGVPGV</u>GARNLPVATPDPGMFPCLHHSQNLLRAV

SNMLQKARQTLEFYPCTSEEIDHEDITKDKTSTVEACLPLELTKNESCL

NSRETSFITNGSCLASRKTSFMMALCLSSIYEDLKMYQVEFKTMNAKLL

MDPKRQIFLDQNMLAVIDELMQALNFNSETVPQKSSLEEPDFYKTKIKL

CILLHAFRIRAVTIDRVMSYLNAS<u>GGG</u>FWVLVVVGGVLACYSLLVTVAF

IIFWV<i>RSKR</i>

In this sequence the first and second peptide linker sequences are underlined, the second peptide; the human CD28 transmembrane domain sequence is in bold and the portion of human CD28 cytoplasmic domain sequence is in italics.

The mature sequence can be preceded by a signal sequence suitable for directing secretion to the surface of a human cell.

For example, the signal sequence can comprise or consist of the sequence:

(SEQ ID NO: 10)
MCHQQLVISWFSLVFLASPLVA

In one example, mb(CD28)IL-12 with a signal sequence can comprise or consist of the sequence:

(SEQ ID NO: 8)
<u>MCHQQLVISWFSLVFLASPLVA</u>IWELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVFTDKT

SATVICRKNASISVRAQDRYYSSSWSEWASVPCSVPGVGVPGVGARNLP

VATPDPGMFPCLHHSQNLLRAVSNMLQKARQTLEFYPCTSEEIDHEDIT

KDKTSTVEACLPLELTKNESCLNSRETSFITNGSCLASRKTSFMMALCL

SSIYEDSKMYQVEFKTMNAKLLMDPKRQIFLDQNMLAVIDELMQALNFN

SETVPQKSSLEEPDFYKTKIKLCILLHAFRIRAVTIDRVMSYLNASGGG

FWVLVVVGGVLACYSLLVTVAFIIFWVRSKR

In this sequence the signal sequence is underlined.

In one example, mb(CD28)IL-12 with a signal sequence can comprise or consist of the sequence:

(SEQ ID NO: 9)
<u>MCHQQLVISWFSLVFLASPLVA</u>IWELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

-continued
LKNSRQVEVSWEYPDTWSTPHSYFSLTFCVQVQGKSKREKKDRVFTDKT

SATVICRKNASISVRAQDRYYSSSWSEWASVPCSVPGVGVPGVGARNLP

VATPDPGMFPCLHHSQNLLRAVSNMLQKARQTLEFYPCTSEEIDHEDIT

KDKTSTVEACLPLELTKNESCLNSRETSFITNGSCLASRKTSFMMALCL

SSIYEDLKMYQVEFKTMNAKLLMDPKRQIFLDQNMLAVIDELMQALNFN

SETVPQKSSLEEPDFYKTKIKLCILLHAFRIRAVTIDRVMSYLNASGGG

FWVLVVVGGVLACYSLLVTVAFIIFWVRSKR

In this sequence the signal sequence is underlined.

In other cases, the signal sequence can comprise or consist of: MLLLVTSLLLCELPHPAFLL IP (SEQ ID NO:11).

In one example, mbIL-12 with a signal sequence can comprise or consist of the sequence:

(SEQ ID NO: 44)
<u>MLLLVTSLLLCELPHPAFLLIP</u>IWELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVFTDKT

SATVICRKNASISVRAQDRYYSSSWSEWASVPCSVPGVGVPGVGARNLP

VATPDPGMFPCLHHSQNLLRAVSNMLQKARQTLEFYPCTSEEIDHEDIT

KDKTSTVEACLPLELTKNESCLNSRETSFITNGSCLASRKTSFMMALCL

SSIYEDSKMYQVEFKTMNAKLLMDPKRQIFLDQNMLAVIDELMQALNFN

SETVPQKSSLEEPDFYKTKIKLCILLHAFRIRAVTIDRVMSYLNASGGG

FWVLVVVGGVLACYSLLVTVAFIIFWVRSKR

In one example, mbIL-12 with a signal sequence can comprise or consist of the sequence:

(SEQ ID NO: 49)
<u>MLLLVTSLLLCELPHPAFLLIP</u>IWELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVFTDKT

SATVICRKNASISVRAQDRYYSSSWSEWASVPCSVPGVGVPGVGARNLP

VATPDPGMFPCLHHSQNLLRAVSNMLQKARQTLEFYPCTSEEIDHEDIT

KDKTSTVEACLPLELTKNESCLNSRETSFITNGSCLASRKTSFMMALCL

SSIYEDLKMYQVEFKTMNAKLLMDPKRQIFLDQNMLAVIDELMQALNFN

SETVPQKSSLEEPDFYKTKIKLCILLHAFRIRAVTIDRVMSYLNASGGG

FWVLVVVGGVLACYSLLVTVAFIIFWVRSKR

In some case, the sequence FWVLVVVGGVLACYSLL-VTVAFIIFWV (SEQ ID NO: 16) can be replaced with MFWVLVVVGGVLACYSLLVTVAFIIFWV (SEQ ID NO: 17) or FWVLVVVGGVLACYSLLVTVAFIIFWVR-SKR (SEQ ID NO: 76).

The first and second linker peptide linker can be have any suitable sequence. For example, the first peptide linker can consist of: 3-24 amino acids, 3-20 amino acids, 3-15 amino acids, 3-10 amino acids (e.g., 3, 4, 5, 6, 7, 8, 9, 10, 11, 12, 13, 14, 15, 16, 17, 18, 19, or 20 amino acids. Preferably, none of the amino acids are proline. For example, the second peptide linker can consist of: 3-24 amino acids, 3-20 amino acids, 3-15 amino acids, 3-10 amino acids (e.g., 3, 4, 5, 6, 7, 8, 9, 10, 11, 12, 13, 14, 15, 16, 17, 18, 19, or 20 amino acids. Preferably, none of the amino acids are proline. Suitable second peptide linkers include glycines and or a mixture of glycines and serines (e.g., GGGGSGGGGS GGGGSGGGGS (SEQ ID NO: 57), GGGG (SEQ ID NO: 58), GGGGS (SEQ ID NO: 14), GGGSGG (SEQ ID NO: 59) and GGGSGGGS (SEQ ID NO: 60).

The portion of the human cytoplasmic domain when present preferably lacks signaling activity.

An amino acid modification refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

Chimeric Antigen Receptors

A chimeric antigen receptor (CAR) refers to an artificial immune cell receptor that is engineered to recognize and bind to a surface antigen. A T cell that expresses a CAR polypeptide is referred to as a CAR T cell. CARs have the ability to redirect T-cell specificity and reactivity toward a selected target in a non-MHC-restricted manner. The non-MHC-restricted antigen recognition gives CAR T cells the ability to recognize an antigen independent of antigen processing, thereby bypassing a major mechanism of tumor escape. A CAR can also be expressed by other immune effector cells, including but not limited to natural killer CAR ("NK CAR") and directed NK cell killing to cells expressing the target of the CAR.

There are various generations of CARs, each of which contains different components. First generation CARs join an antibody-derived scFv to the CD3ζ intracellular signaling domain of the T cell receptor through a spacer region (also called a hinge domain) and a transmembrane domain. Second generation CARs incorporate an additional co-stimulatory domain (e.g., CD28, 4-BB, or ICOS) to supply a co-stimulatory signal. Third generation CARs contain two co-stimulatory domains (e.g., a combination of CD27, CD28, 4-1 BB, ICOS, or OX40) fused with the TCR CD3ζ chain.

(a) Extracellular Binding Domain

The CAR described herein are fusion proteins comprising an extracellular binding domain that recognizes a tumor antigen, e.g., a solid tumor antigen. This extracellular domain is often a single chain fragment (scFv) of an antibody or other antibody fragment, but it can also be a ligand that binds to a cell receptor. The binding domain is followed by: a spacer, a transmembrane domain, at least one co-stimulatory domain and an intracellular domain comprising a signaling domain of the T cell receptor (TCR) complex (e.g., CD3ζ). A CAR is often fused to a signal peptide at the N-terminus for surface expression.

Where the binding domain is an scFv, there is a heavy chain variable region and a light chain variable region, which can be in an order and are joined together via a flexible linker of, e.g., 5-25 amino acids. In some embodiments, a useful flexible linker is 1, 2, 3, 4, 5, 6, 7, 8, 9, or 10 repeats of the sequence GGGS (SEQ ID NO: 13). In some embodiments, a useful flexible linker is 1, 2, 3, 4, 5, 6, 7, 8, 9, or 10 repeats of the sequence GGGGS (SEQ ID NO: 14) or SEQ ID NO:13. In some embodiments, the light chain variable domain is amino terminal to the heavy chain variable domain in other cases it is carboxy terminal to the heavy chain variable domain. In some cases the linker comprises the sequence SSGGGGSGGGGSGGGGS (SEQ ID NO:12).

(b) Transmembrane Domain

The CAR polypeptides disclosed herein can contain a transmembrane domain, which can be a hydrophobic alpha helix that spans the membrane. As used herein, a transmembrane domain refers to any protein structure that is thermodynamically stable in a cell membrane, preferably a eukaryotic cell membrane.

The transmembrane domain of a CAR as provided herein can be a CD28 transmembrane domain having the sequence: FWVLVVVGGVLACYSLLVTVAFIIFWV (SEQ ID NO: 16). Other transmembrane domains can be used including those shown below.

TABLE 1

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 15) |
| CD28 | NM_006139 | 27 aa | FWVLVVVGGVLACYSLLVTVAFIIFWV (SEQ ID NO: 16) |
| CD28(M) | NM_006139 | 28 aa | MFWVLVVVGGVLACYSLLVTVAFIIFWV (SEQ ID NO: 17) |

TABLE 1-continued

Examples of Transmembrane Domains

| Name | Accession | Length | Sequence |
|---|---|---|---|
| CD4 | M35160 | 22 aa | MALIVLGGVAGLLLFIGLGIFF (SEQ ID NO: 18) |
| CD8tm | NM_001768 | 21 aa | IYIWAPLAGTCGVLLLSLVIT (SEQ ID NO: 19) |
| CD8tm2 | NM_001768 | 23 aa | IYIWAPLAGTCGVLLLSLVITLY (SEQ ID NO: 20) |
| CD8tm3 | NM_001768 | 24 aa | IYIWAPLAGTCGVLLLSLVITLYC (SEQ ID NO: 21) |
| 4-1BB | NM_001561 | 27 aa | IISFFLALTSTALLFLLFFLTLRFSVV (SEQ ID NO: 22) |
| NKG2D | NM_007360 | 21 aa | PFFFCCFIAVAMGIRFIIMVA (SEQ ID NO: 23) |

(c) Spacer Region

The CAR or polypeptide described herein can include a spacer region located between the targeting domain (i.e., a HER2 or TAG-72 targeted scFv or variant thereof) and the transmembrane domain. The spacer region can function to provide flexibility to the CAR, or domains thereof, or to prevent steric hindrance of the CAR, or domains thereof. A variety of different spacers can be used. Some of them include at least portion of a human Fc region, for example a hinge portion of a human Fc region or a CH3 domain or variants thereof. Table 2 below provides various spacers that can be used in the CARs described herein.

TABLE 2

Examples of Spacers

| Name | Length | Sequence |
|---|---|---|
| a3 | 3 aa | AAA |
| linker | 10 aa | GGGSSGGGSG (SEQ ID NO: 24) |
| IgG4 hinge (S→P) (S228P) | 12 aa | ESKYGPPCPPCP (SEQ ID NO: 25) |
| IgG4 hinge | 12 aa | ESKYGPPCPSCP (SEQ ID NO: 26) |
| IgG4 hinge (S228P) + linker | 22 aa | ESKYGPPCPPCPGGGSSGGGSG (SEQ ID NO: 27) |
| CD28 hinge | 39 aa | IEVMYPPPYLDNEKSNGTIIHVKGKHLCPSPLFPGPSKP (SEQ ID NO: 28) |
| CD8 hinge-48aa | 48 aa | AKPTTTPAPRPPTPAPTIASQPLSLRPEACRPAAGGAVHTRGLDFACD (SEQ ID NO: 29) |
| CD8 hinge-45aa | 45 aa | TTTPAPRPPTPAPTIASQPLSLRPEACRPAAGGAVHTRGLDFACD (SEQ ID NO: 30) |
| IgG4(HL-CH3) Also called IgG4 (HL-ΔCH2) (includes S228P in hinge) | 129 aa | ESKYGPPCPPCPGGGSSGGGSGGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 31) |
| IgG4(L235E, N297Q) | 229 aa | ESKYGPPCPSCPAPEFEGGPSVFLFPPKPKDTLMISRTPEVTCVVVDVSQEDPEVQFNWYVDGVEVHNAKTKPREEQFQSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 32) |
| IgG4(S228P, L235E, N297Q) | 229 aa | ESKYGPPCPPCPAPEFEGGPSVFLFPPKPKDTLMISRTPEVTCVVVDVSQEDPEVQFNWYVDGVEVHNAKTKPREEQFQSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 33) |

TABLE 2-continued

Examples of Spacers

| Name | Length | Sequence |
| --- | --- | --- |
| IgG4(CH3)<br>Also called IgG4<br>(ΔCH2) | 107 aa | GQPREPQVYTLPPSQEEMTKNQVSLTCLVKGFYPSDIA<br>VEWESNGQPENNYKTTPPVLDSDGSFFLYSRLTVDKSR<br>WQEGNVFSCSVMHEALHNHYTQKSLSLSLGK (SEQ<br>ID NO: 34) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain (called CH3 or ΔCH2) or both a CH3 domain and a CH2 domain. The immunoglobulin derived sequences can include one or more amino acid modifications, for example, 1, 2, 3, 4 or 5 substitutions, e.g., substitutions that reduce off-target binding.

The hinge/linker region can also comprise an IgG4 hinge region having the sequence ESKYGPPCPSCP (SEQ ID NO: 26) or ESKYGPPCPPCP (SEQ ID NO: 25). The hinge/linker region can also comprise the sequence ESKYGPPCPPCP (SEQ ID NO: 25) followed by the linker sequence GGGSSGGGSG (SEQ ID NO: 24) followed by IgG4 CH3 sequence: GQPREPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK (SEQ ID NO: 34).

Thus, the entire linker/spacer region can comprise the sequence: ESKYGPPCPPCPGGGSSGGGSGGQPREPQVYTLPPSQEEMTKNQVSLTCLVKGFYPSDI AVEWESNGQPENNYKTTPPVLDSDGSFFLYSRLTVDKSRWQEGNVFSCSVMHEALHNHY TQKSLSLSLGK (SEQ ID NO: 31). In some cases, the spacer has 1, 2, 3, 4, or 5 single amino acid changes (e.g., conservative changes) compared to SEQ ID NO: 31. In some cases, the IgG4 Fc hinge/linker region that is mutated at two positions (e.g., L235E and N297Q) in a manner that reduces binding by Fc receptors (FcRs).

(d) Intracellular Signaling Domains

Any of the CAR constructs described herein contain one or more intracellular signaling domains (e.g., CD3ζ, and optionally one or more co-stimulatory domains), which are the functional end of the receptor. Following antigen recognition, receptors cluster and a signal is transmitted to the cell.

CD3ζ is the cytoplasmic signaling domain of the T cell receptor complex. CD3ζ contains three immunoreceptor tyrosine-based activation motifs (ITAMs), which transmit an activation signal to the T cell after the T cell is engaged with a cognate antigen. In some cases, CD3ζ provides a primary T cell activation signal but not a fully competent activation signal, which requires a co-stimulatory signal.

Accordingly, in some examples, the CAR polypeptides disclosed herein may further comprise one or more co-stimulatory signaling domains in addition to CD3 ζ. For example, the co-stimulatory domain CD28 and/or 4-1 BB can be used to transmit a proliferative/survival signal together with the primary signaling mediated by CD3ζ.

The co-stimulatory domain(s) are located between the transmembrane domain and the CD3ζ signaling domain. Table 3 includes examples of suitable co-stimulatory domains together with the sequence of the CD3ζ signaling domain.

TABLE 3

CD3ζ Domain and Examples of Co-stimulatory Domains

| Name | Accession | Length | Sequence |
| --- | --- | --- | --- |
| CD3ζ | J04132.1 | 113 aa | RVKFSRSADAPAYQQGQNQLYNELNLGRREEYDVLDKRR<br>GRDPEMGGKPRRKNPQEGLYNELQKDKMAEAYSEIGMKG<br>ERRRGKGHDGLYQGLSTATKDTYDALHMQALPPR (SEQ<br>ID NO: 35)<br>ITAMS 1-3 underlined |
| CD3ζ<br>variant | | 113 aa | RVKFSRSADAPAYQQGQNQLYNELNLGRREEYDVLDKRR<br>GRDPEMGGKPRRKNPQEGLFNELQKDKMAEAFSEIGMKG<br>ERRRGKGHDGLFQGLSTATKDTFDALHMQALPPR (SEQ<br>ID NO: 50) |
| CD3ζ<br>variant | | 113 aa | RVKFSRSADAPAYQQGQNQLYNELNLGRREEYDVLDKRR<br>GRDPEMGGKPRRKNPQEGLFNELQKDKMAEAFSEIGMKG<br>ERRRGKGHDGLYQGLSTATKDTYDALHMQALPPR (SEQ<br>ID NO: 51) |
| CD3ζ<br>variant | | 113 aa | RVKFSRSADAPAYQQGQNQLYNELNLGRREEYDVLDKRR<br>GRDPEMGGKPRRKNPQEGLYNELQKDKMAEAYSEIGMKG<br>ERRRGKGHDGLFQGLSTATKDTFDALHMQALPPR (SEQ<br>ID NO: 52) |
| CD3ζ<br>variant | | 113 aa | RVKFSRSADAPAYQQGQNQLYNELNLGRREEYDVLDKRR<br>GRDPEMGGKPRRKNPQEGLYNELQKDKMAEAFSEIGMKG<br>ERRRGKGHDGLFQGLSTATKDTFDALHMQALPPR (SEQ<br>ID NO: 53) |

TABLE 3-continued

CD3ζ Domain and Examples of Co-stimulatory Domains

| Name | Accession | Length | Sequence |
|---|---|---|---|
| CD3ζ variant | | 113 aa | RVKFSRSADAPAYQQGQNQLYNELNLGRREEYDVLDKRR GRDPEMGGKPRRKNPQEGLFNELQKDKMAEAYSEIGMKG ERRRGKGHDGLFQGLSTATKDTFDALHMQALPPR (SEQ ID NO: 54) |
| CD3ζ variant | | 113 aa | RVKFSRSADAPAYQQGQNQLYNELNLGRREEYDVLDKRR GRDPEMGGKPRRKNPQEGLFNELQKDKMAEAFSEIGMKG ERRRGKGHDGLYQGLSTATKDTFDALHMQALPPR (SEQ ID NO: 55) |
| CD3ζ variant | | 113 aa | RVKFSRSADAPAYQQGQNQLYNELNLGRREEYDVLDKRR GRDPEMGGKPRRKNPQEGLFNELQKDKMAEAFSEIGMKG ERRRGKGHDGLFQGLSTATKDTYDALHMQALPPR (SEQ ID NO: 56) |
| CD28 | NM_006139 | 42 aa | RSKRSRLLHSDYMNMTPRRPGPTRKHYQPYAPPRDFAAY RS (SEQ ID NO: 36) |
| CD28gg* | NM_006139 | 42 aa | RSKRSRGGHSDYMNMTPRRPGPTRKHYQPYAPPRDFAAY RS (SEQ ID NO: 37) |
| 41BB | NM_001561 | 42 aa | KRGRKKLLYIFKQPFMRPVQTTQEEDGCSCRFPEEEEGG CEL (SEQ ID NO: 38) |
| OX40 | NM_003327 | 42 aa | ALYLLRRDQRLPPDAHKPPGGGSFRTPIQEEQADAHSTL AKI (SEQ ID NO: 39) |
| 2B4 | NM_016382 | 120 aa | AWRRKRKEKQSETSPKEFLTIYEDVKDLKTRRNHEQEQT FPGGGSTIYSMIQSQSSAPTSQEPAYTLYSLIQPSRKSG SRKRNHSPSFNSTIYEVIGKSQPKAQNPARLSRKELENF DVYS (SEQ ID NO: 40) |

In some examples, the CD3ζ signaling domain comprises an amino acid sequence that is at least 90%, at least 95%, at least 98% identical to SEQ ID NO: 35. In such instances, the CD3ζ signaling domain has 1, 2, 3, 4, or 5 amino acid changes (preferably conservative substitutions) compared to SEQ ID NO: 35. In other examples, the CD3ζ signaling domain is SEQ ID NO: 35.

In various embodiments: the co-stimulatory domain is selected from the group consisting of: a co-stimulatory domain depicted in Table 3 or a variant thereof having 1-5 (e.g., 1 or 2) amino acid modifications, a CD28 co-stimulatory domain or a variant thereof having 1-5 (e.g., 1 or 2) amino acid modifications, a 4-1 BB co-stimulatory domain or a variant thereof having 1-5 (e.g., 1 or 2) amino acid modifications and an OX40 co-stimulatory domain or a variant thereof having 1-5 (e.g., 1 or 2) amino acid modifications. In certain embodiments, a 4-1 BB co-stimulatory domain or a variant thereof having 1-5 (e.g., 1 or 2) amino acid modifications is present in the CAR polypeptides described herein.

In some embodiments, there are two co-stimulatory domains, for example, a CD28 co-stimulatory domain or a variant thereof having 1-5 (e.g., 1 or 2) amino acid modifications (e.g., substitutions) and a 4-1 BB co-stimulatory domain or a variant thereof having 1-5 (e.g., 1 or 2) amino acid modifications (e.g., substitutions). In various embodiments the 1-5 (e.g., 1 or 2) amino acid modification are substitutions. In various embodiments, the co-stimulatory domain is amino terminal to the CD3ζ signaling domain and a short linker consisting of 2-10, e.g., 3 amino acids (e.g., GGG) can be positioned between the co-stimulatory domain and the CD3ζ signaling domain.

In some cases, the CAR can be produced using a vector in which the CAR open reading frame is followed by a T2A ribosome skip sequence and a truncated EGFR (EGFRt), which lacks the cytoplasmic signaling tail, or a truncated CD19R (also called CD19t). In this arrangement, co-expression of EGFRt or CD19t provides an inert, non-immunogenic surface marker that allows for accurate measurement of gene modified cells, and enables positive selection of gene-modified cells, as well as efficient cell tracking of the therapeutic T cells in vivo following adoptive transfer. Efficiently controlling proliferation to avoid cytokine storm and off-target toxicity is an important hurdle for the success of T cell immunotherapy. The EGFRt or the CD19t incorporated in the CAR lentiviral vector can act as suicide gene to ablate the CAR+ T cells in cases of treatment-related toxicity.

The CD3ζ signaling domain can be followed by a ribosomal skip sequence (e.g., LEGGGEGRGSLLTCGD-VEENPGPR; SEQ ID NO: 45) and a truncated EGFR having a sequence that is at least 90%, at least 95%, at least 98% identical to or identical to:

(SEQ ID NO: 46)
LVTSLLLCELPHPAFLLIPRKVCNGIGIGEFKDSLSINATNIKHFKNCT

SISGDLHILPVAFRGDSFTHTPPLDPQELDILKTVKEITGFLLIQAWPE

NRTDLHAFENLEIIRGRTKQHGQFSLAVVSLNITSLGLRSLKEISDGDV

IISGNKNLCYANTINWKKLFGTSGQKTKIISNRGENSCKATGQVCHALC

SPEGCWGPEPRDCVSCRNVSRGRECVDKCNLLEGEPREFVENSECIQCH

PECLPQAMNITCTGRGPDNCIQCAHYIDGPHCVKTCPAGVMGENNTLVW

KYADAGHVCHLCHPNCTYGCTGPGLEGCPTNGPKIPSIATGMVGALLLL

LVVALGIGLFM.

In some cases, the truncated EGFR has 1, 2, 3, 4 of 5 amino acid changes (preferably conservative) compared to SEQ ID NO: 46.

Alternatively the CD3ζ signaling domain can be followed by a ribosomal skip sequence (e.g., LEGGGEGRGSLLTCGDVEENPGPR; SEQ ID NO: 45) and a truncated CD19R (also called CD19t) having a sequence that is at least 90%, at least 95%, at least 98% identical to or identical to:

(SEQ ID NO: 47)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCVPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKR.

The CAR or polypeptide described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, overlapping PCR, primer-assisted ligation, site-directed mutagenesis, etc.) as is convenient. The resulting coding region is preferably inserted into an expression vector and used to transform a suitable expression host cell line, preferably a T lymphocyte, and most preferably an autologous T lymphocyte.

Various T cell subsets isolated from the patient can be transduced with a vector for CAR or polypeptide expression. Central memory T cells are one useful T cell subset. Central memory T cell can be isolated from peripheral blood mononuclear cells (PBMC) by selecting for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a lentiviral vector that directs the expression of the CAR or as well as a non-immunogenic surface marker for in vivo detection, ablation, and potential ex vivo selection. The activated/genetically modified central memory T cells can be expanded in vitro with IL-2/IL-15 and then cryopreserved. Additional methods of preparing CAR T cells can be found in PCT/US2016/043392.

Methods for preparing useful T cell populations are described in, for example, WO 2017/015490 and WO 2018/102761. In some cases, it may be useful to use natural killer (NK) cells, e.g., allogenic NK cells derived from peripheral blood or cord blood. In other cases, NK cells can be derived from human embryonic stem cells (hESCs) or induced pluripotent stem cells (iPSCs).

In some embodiments, described herein is a composition comprising the iPSC-derived CAR T cells or CAR NK cells. In some embodiments, a composition comprising iPSC-derived CAR T cells or CAR NK cells has enhanced therapeutic properties. In some embodiments, the iPSC-derived CAR T cells or CAR NK cells demonstrate enhanced functional activity including potent cytokine production, cytotoxicity and cytostatic inhibition of tumor growth, e.g., as activity that reduces the amount of tumor load.

The CAR can be transiently expressed in a T cell population by an mRNA encoding the CAR. The mRNA can be introduced into the T cells by electroporation (Wiesinger et al. 2019 Cancers (Basel) 11:1198).

In some embodiments, a composition comprising the CAR T cells comprise one or more of helper T cells, cytotoxic T cells, memory T cells, naïve T cells, regulatory T cells, natural killer T cells, or combinations thereof.

Suitable TAG-72 targeted CAR are described in, e.g., WO 2020/028721. Suitable HER2 targeted CAR are described in, e.g., WO 2017/079694; suitable PSCA targeted CAR are described in WO 2017/062628.

In some cases, the TAG-72 CAR comprises the amino acid sequence:

(SEQ ID NO: 61)
QVQLVQSGAEVVKPGASVKISCKASGYTFTDHAIHWVKQNPGQRLEWIGY

FSPGNDDEKYSQKFQGKATLTADTSASTAYVELSSLRSEDTAVYFCTRSL

NMAYWGQGTLVTVSSGSTSGGGSGGGSGGGGSSDIVMSQSPDSLAVSLGE

RVTLNCKSSQSVLYSSNSKNYLAWYQQKPGQSPKLLIYWASTRESGVPDR

FSGSGSGTDFTLTISSVQAEDVAVYYCQQYYSYPLSFGAGTKLELKESKY

GPPCPPCPGGGSSGGGSGGQPREPQVYTLPPSQEEMTKNQVSLTCLVKGF

YPSDIAVEWESNGQPENNYKTTPPVLDSDGSFFLYSRLTVDKSRWQEGNV

FSCSVMHEALHNHYTQKSLSLSLGK<u>MFWVLVVVGGVLACYSLLVTVAFII</u>

<u>FWVKRGRKKLLYIFKQPFMRPVQTTQEEDGCSCRFPEEEEGGCELGGGRV</u>

KFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYD

ALHMQALPPR

Thus, it includes, from amino to carboxy terminus, an scFv (underlined) and spacer (not underlined) a CD28 transmembrane domain (MFWVLVVVGGVLACYSLL-VTVAFIIFWV, SEQ ID NO:17; underlined), a 4-1 BB co-stimulatory domain (KRGRKKLLY-IFKQPFMRPVQTTQEEDGCSCRFPEEEEGGCEL, SEQ ID NO:38; not underlined), a GGG linker (GGG; underlined) and a CD3zeta domain (RVKFSRSADAPA-YQQGQNQLYNELNLGRREEYDVLDKRR-GRDPEMGGKPRRKNPQEGL YNELQKDKMAEAYSEIGMKGERRRGKGHDG-LYQGLSTATKDTYDALHMQALPPR, SEQ ID NO:35; not underlined). The scFv includes a VH chain comprising the amino acid sequence: QVQLVQSGAEVVKP-GASVKISCKASGYTFTDHAIHWVKQNPGQRLEWI-GYFSPGNDDFKY SQKFQGKATLTADTSASTAYV-ELSSLRSEDTAVYFCTRSLNMAYWGQGTLVTVSS (SEQ ID NO: 63). This VH chain includes: VH CDR1 (DHAIH, SEQ ID NO:64); VH CDR2 (YFSPGNDDFKYSQKFQG, SEQ ID NO:65); and VH CDR3 (SLNMAY, SEQ ID NO:66). The scFv includes a VL chain comprising the amino acid sequence: DIVMSQSPD-SLAVSLGERVTLNCKSSQSVLYSSNSK-NYLAWYQQKPGQSPKLLIYWASTRE SGVPDRFSGSGSGTDFTLTISSVQAEDVA-VYYCQQYYSYPLSFGAGTKLELK (SEQ ID NO:67). This VL chain includes VL CDR1 (KSSQSVLYSSNSK- NYLA, SEQ ID NO:68); VL CDR2 (WASTRES, SEQ ID NO:69); and VL CDR3 (QQYYSYPLS, SEQ ID NO:70).

The spacer includes: an IgG4 hinge with a S to P mutation (ESKYGPPCPECP, SEQ ID NO:25; mutation in bold, underline), a linker (GGGSSGGGSG, SEQ ID NO:24), and an IgG4 CH3 domain (GQPREPQVYTLPPSQEEMT-KNQVSLTCLVKGFYPSDIAVEWESNGQPEN-NYKTTPPVLDS DGSFFLY-SRLTVDKSRWQEGNVFSCSVMHEALHNHYTQKSLS-LSLGK, SEQ ID NO:34).

In some cases, the mCD28 transmembrane domain can be replaced by the following CD28 transmembrane domain: FWVLVVVGGVLACYSLLVTVAFIIFWV (SEQ ID NO:16).

In some cases, the TAG72 includes a signal sequence at the amino terminus, e.g. a GMCSF signal sequence (MLLLVTSLLLCELPHPAFLLIP; SEQ ID NO:11). Thus, the TAG72 CAR with a signal sequence can be:

(SEQ ID NO: 62)
MLLLVTSLLLCELPHPAFLLIPQVQLVQSGAEVVKPGASVKISCKASGYT

FTDHAIHWVKQNPGQRLEWIGYFSPGNDDEKYSQKFQGKATLTADTSAST

AYVELSSLRSEDTAVYFCTRSLNMAYWGQGTLVTVSSGSTSGGGSGGGSG

GGGSSDIVMSQSPDSLAVSLGERVTLNCKSSQSVLYSSNSKNYLAWYQQK

PGQSPKLLIYWASTRESGVPDRESGSGSGTDETLTISSVQAEDVAVYYCQ

QYYSYPLSFGAGTKLELKESKYGPPCPPCPGGGSSGGGSGGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKMFW

VLVVVGGVLACYSLLVTVAFIIFWVKRGRKKLLYIFKQPFMRPVQTTQEE

DGCSCRFPEEEEGGCELGGGRVKFSRSADAPAYQQGQNQLYNELNLGRRE

EYDVLDKRRGRDPEMGGKPRRKNPQEGLYNELQKDKMAEAYSEIGMKGER

RRGKGHDGLYQGLSTATKDTYDALHMQALPPR

In some cases, the TAG72 CAR can be followed by a T2A skip sequence and a truncated CD19 have can serve as a marker:

(SEQ ID NO: 71)
LEGGGEGRGSLLTCGDVEENPGPTRMPPPRLLFFLLFLTPMEVRPEEPLV

VKVEEGDNAVLQCLKGTSDGPTQQLTWSRESPLKPFLKLSLGLPGLGIHM

RPLAIWLFIFNVSQQMGGFYLCQPGPPSEKAWQPGWTVNVEGSGELFRWN

VSDLGGLGCGLKNRSSEGPSSPSGKLMSPKLYVWAKDRPEIWEGEPPCVP

PRDSLNQSLSQDLTMAPGSTLWLSCGVPPDSVSRGPLSWTHVHPKGPKSL

LSLELKDDRPARDMWVMETGLLLPRATAQDAGKYYCHRGNLTMSFHLEIT

ARPVLWHWLLRTGGWKVSAVTLAYLIFCLCSLVGILHLQRALVLRRKR

HER2 CAR

In some cases the HER2 CAR comprises the amino acid sequence:

(SEQ ID NO: 72)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKGSTSGGGSGGGSGGGGSSEVQLVESGGGLVQPGGSLRLSCAAS

GFNIKDTYIHWVRQAPGKGLEWVARIYPTNGYTRYADSVKGRFTISADTS

KNTAYLQMNSLRAEDTAVYYCSRWGGDGFYAMDYWGQGTLVTVSSESKYG

PPCPPCPAPEFEGGPSVFLFPPKPKDTLMISRTPEVTCVVVDVSQEDPEV

QFNWYVDGVEVHNAKTKPREEQFQSTYRVVSVLTVLHQDWLNGKEYKCKV

SNKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNVF

SCSVMHEALHNHYTQKSLSLSLGKIYIWAPLAGTCGVLLLSLVITKRGRK

KLLYIFKQPFMRPVQTTQEEDGCSCRFPEEEEGGCELGGGRVKFSRSADA

PAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALP

PR

Thus, it includes, from amino to carboxy terminus, an scFv (underlined) and spacer (not underlined) a CD8 transmembrane domain (underlined), a 4-1 BB co-stimulatory domain (not underlined), a GGG linker (underlined) and a CD3zeta domain (not underlined). The spacer in this HER2 CAR is IgG4(S228P, L235E, N297Q).

PSCA CAR

Suitable PSCA CAR include:

PSCAscFv-IgG4(HL-CH3)-CD4tm-41BB-Zeta
(SEQ ID NO: 73)
DIQLTQSPSTLSASVGDRVTITCSASSSVRFIHWYQQKPGKAPKRLIYDT

SKLASGVPSRFSGSGSGTDFTLTISSLOPEDFATYYCQQWGSSPFTFGQG

TKVEIKGSTSGGGSGGGSGGGGSSEVQLVEYGGGLVQPGGSLRLSCAASG

FNIKDYYIHWVRQAPGKGLEWVAWIDPENGDTEFVPKFQGRATMSADTSK

NTAYLQMNSLRAEDTAVYYCKTGGFWGQGTLVTVSSESKYGPPCPPCPGG

GSSGGGSGGQPREPQVYTLPPSQEEMTKNQVSLTCLVKGFYPSDIAVEWE

SNGQPENNYKTTPPVLDSDGSFFLYSRLTVDKSRWQEGNVFSCSVMHEAL

HNHYTQKSLSLSLGKMALIVLGGVAGLLLFIGLGIFFKRGRKKLLYIFKQ

PFMRPVQTTQEEDGCSCRFPEEEEGGCELGGGRVKFSRSADAPAYQQGQN

QLYNELNLGRREEYDVLDKRRGRDPEMGGKPRRKNPQEGLYNELQKDKMA

EAYSEIGMKGERRRGKGHDGLYQGLSTATKDTYDALHMQALPPR

PSCAscFv-Linker-CD4tm-41BB-Zeta
(SEQ ID NO: 74)
DIQLTQSPSTLSASVGDRVTITCSASSSVRFIHWYQQKPGKAPKRLIYDT

SKLASGVPSRFSGSGSGTDFTLTISSLEPEDFATYYCQQWGSSPFTFGQG

TKVEIKGSTSGGGSGGGSGGGGSSEVELVEYGGGLVQPGGSLRLSCAASG

FNIKDYYIHWVRQAPGKGLEWVAWIDPENGDTEFVPKFQGRATMSADTSK

NTAYLQMNSLRAEDTAVYYCKTGGFWGQGTLVTVSSGGGSSGGGSGMALI

VLGGVAGLLLFIGLGIFFKRGRKKLLYIFKQPFMRPVQTTQEEDGCSCRF

-continued

PEEEEGGCELGGGRVKFSRSADAPAYQQGQNQLYNELNLGRREEYDVLDK

RRGRDPEMGGKPRRKNPQEGLYNELQKDKMAEAYSEIGMKGERRRGKGHD

GLYQGLSTATKDTYDALHMQALPPR

PSCAscFv-IgG4(S228P, L235E, N297Q)-
CD4tm-41BB-Zeta (SEQ ID NO: 75)
DIQLTQSPSTLSASVGDRVTITCSASSSVRFIHWYQQKPGKAPKRLIYDT

SKLASGVPSRFSGSGSGTDFTLTISSLQPEDFATYYCQQWGSSPFTFGQG

TKVEIKGSTSGGGSGGGSGGGGSSEVQLVEYGGGLVQPGGSLRLSCAASG

FNIKDYYIHWVRQAPGKGLEWVAWIDPENGDTEFVPKFQGRATMSADTSK

NTAYLQMNSLRAEDTAVYYCKTGGFWGQGTLVTVSSESKYGPPCPPCPAP

EFEGGPSVFLFPPKPKDTLMISRTPEVTCVVVDVSQEDPEVQFNWYVDGV

EVHNAKTKPREEQFQSTYRVVSVLTVLHQDWLNGKEYKCKVSNKGLPSSI

EKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEAL

HNHYTQKSLSLSLGKMALIVLGGVAGLLLFIGLGIFFKRGRKKLLYIFKQ

PFMRPVQTTQEEDGCSCRFPEEEEGGCELGGGRVKFSRSADAPAYQQGQN

QLYNELNLGRREEYDVLDKRRGRDPEMGGKPRRKNPQEGLYNELQKDKMA

EAYSEIGMKGERRRGKGHDGLYQGLSTATKDTYDALHMQALPPR

Treatment of Cancer

Aspects of the present disclosure provide methods for treating a subject having a cancer by administering immune cells, e.g., T cells that express mb(28)IL-12 and a chimeric antigen receptor.

(a) Subjects

The subject to be treated by the methods described can be a human patient having solid tumor, e.g., gastrointestinal cancer, breast cancer, lung cancer, bladder cancer, thyroid cancer, endometrial cancer, esophageal cancer, and ovarian cancer. Non-limiting examples of gastrointestinal cancers include colon cancer, gastric cancer, rectal cancer, colorectal cancer, pancreatic cancer, and combinations thereof.

A subject at risk of having cancer might show one or more symptoms of a cancer, e.g., unexplained weight loss, fatigue, pain, persistent cough, lumps under the skin, or unusual bleeding. A subject at risk of having cancer might have one or more risk factors of a cancer, e.g., family history of cancer, age, tobacco use, obesity, or exposure to sun or carcinogens. A subject who needs the treatment described herein can be identified by routine medical examination, e.g., laboratory tests, biopsy, magnetic resonance imaging (MRI), or ultrasound exams.

(b) Treatment Regimens

Aspects of the present disclosure provide methods of treating a solid tumor comprising administering a lymphodepletion treatment (e.g., cyclophosphamide) in combination with immune cells expressing mb(28)IL-12 and an appropriate chimeric antigen receptor. In some cases, the treatment also includes an inhibitor of PD-L1 activity such as an anti-PD-L1 antibody of an anti-PD-1 antibody or some other therapeutic that reduces immunosuppression. The two components can be administered the same day or on different days.

Any subject suitable for the treatment methods described herein can receive a lymphodepleting therapy to reduce or deplete the endogenous lymphocytes of the subject. Lymphodepletion refers to the destruction of endogenous lymphocytes and/or T cells, which is commonly used prior to immunotransplantation and immunotherapy. Lymphodepletion can be achieved by administering a lymphodepleting agent and/or irradiation (e.g., stereotactic radiation). A lymphodepleting agent can be any molecule capable of reducing, depleting, or eliminating endogenous lymphocytes and/or T cells when administered to a subject. In some examples, the lymphodepleting agents are cytotoxic agents that specifically kill lymphocytes. Non-limiting examples of lymphodepleting agents include cyclophosphamide, fludarabine, gemcitabine, methotrexate, doxorubicin, and etopside phosphate. In some cases the lymphodepletion treatment is non-myeloablative.

Methods described herein can include a conditioning regimen comprising a single lymphodepleting agent (e.g., cyclophosphamide) or multiple lymphodepleting agents (e.g., cyclophosphamide and fludarabine). The subject to be treated by the methods described herein can receive one or more doses of the one or more lymphodepleting agents for a period suitable for reducing or depleting the endogenous lymphocytes of the subject (e.g., 1-5 days).

The subject can then be administered any of CAR immune cells described herein after administration of the lymphodepleting therapy as described herein. For example, the one or more lymphodepleting agents can be administered to the subject 1-5 days (e.g., 1, 2, 3, 4, or 5 days) prior to administering the CAR immune cells, e.g., CAR T cells.

Methods described herein can include redosing the subject with CAR immune cells. In some examples, the subject is administered a lymphodepleting treatment prior to redosing of the anti-CAR immune cells. Each dose of the CAR immune cells can be the same or the doses can be ascending or descending.

Methods described herein can be used in combination with another anti-cancer therapy (e.g., chemotherapy) or with another therapeutic agent that reduces side effects of the therapy described herein.

(c) Administration

An effective amount of a therapy (e.g., lymphodepleting agent, T cells expressing a CAR) can be administered to a subject (e.g., a human) in need of the treatment via any suitable route (e.g., administered locally or systemically to a subject). Suitable modes of administration include injection, infusion, instillation, or ingestion. Injection includes, without limitation, intravenous, intramuscular, intra-arterial, intrathecal, intraventricular, intradermal, intraperitoneal, and subcutaneous injection and infusion.

An effective amount refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of treatment, the nature of concurrent therapy, if any, the specific route of administration and like factors.

The materials, methods, and examples are illustrative only and not intended to be limiting. All publications, patent applications, patents, sequences, database entries, and other references mentioned herein are incorporated by reference in their entirety for any and all purposes.

Other features and advantages of the described compositions and methods will be apparent from the following detailed description and figures, and from the claims.

EXAMPLES

In order that the invention described may be more fully understood, the following examples are set forth. The materials and method used in the Examples below are detailed following the Examples. The examples described in this application are offered to illustrate the methods and compositions provided herein and are not to be construed in any way as limiting their scope.

Figure 1:
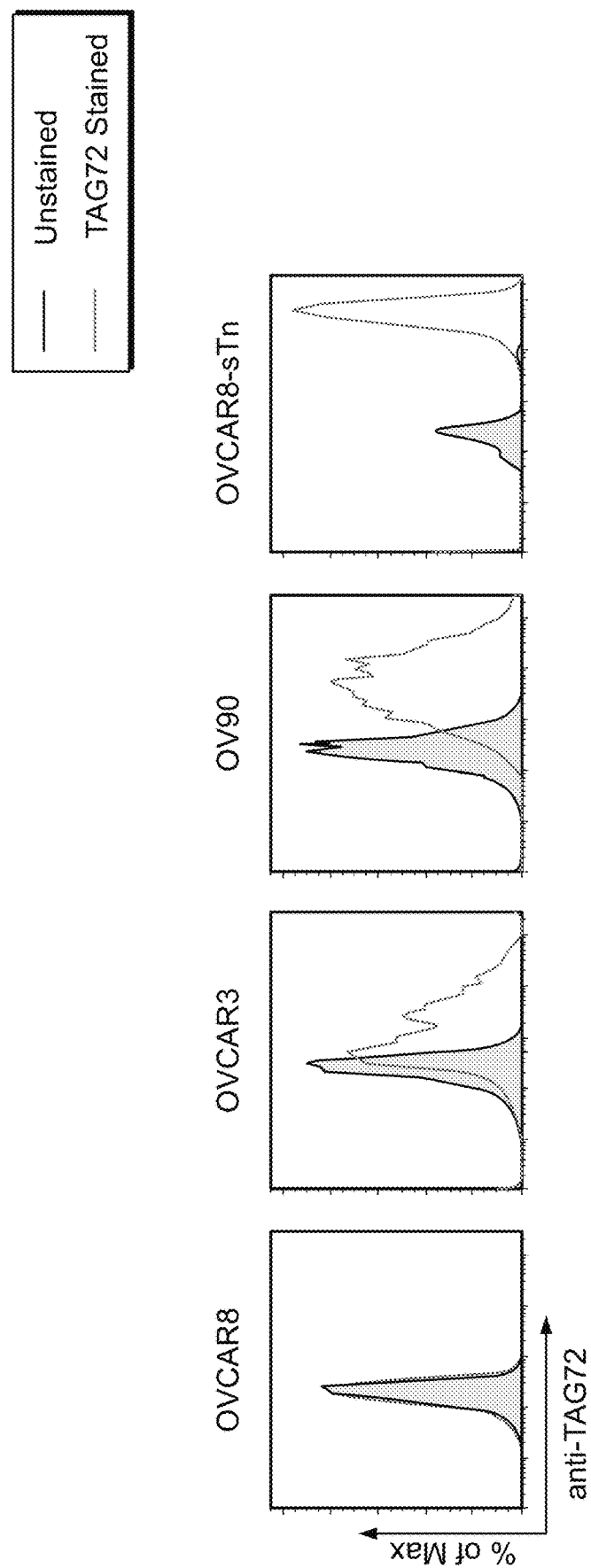
FIG. 1. TAG72 expression on ovarian tumor cell lines. Flow cytometric analysis of TAG72 expression on human OVCAR8 (TAG72-negative), human OVCAR3 (TAG72-positive), human OV90 (TAG72-positive), human OVCAR8-sTn (TAG72-positive) tumor cell lines.
Figure 2:
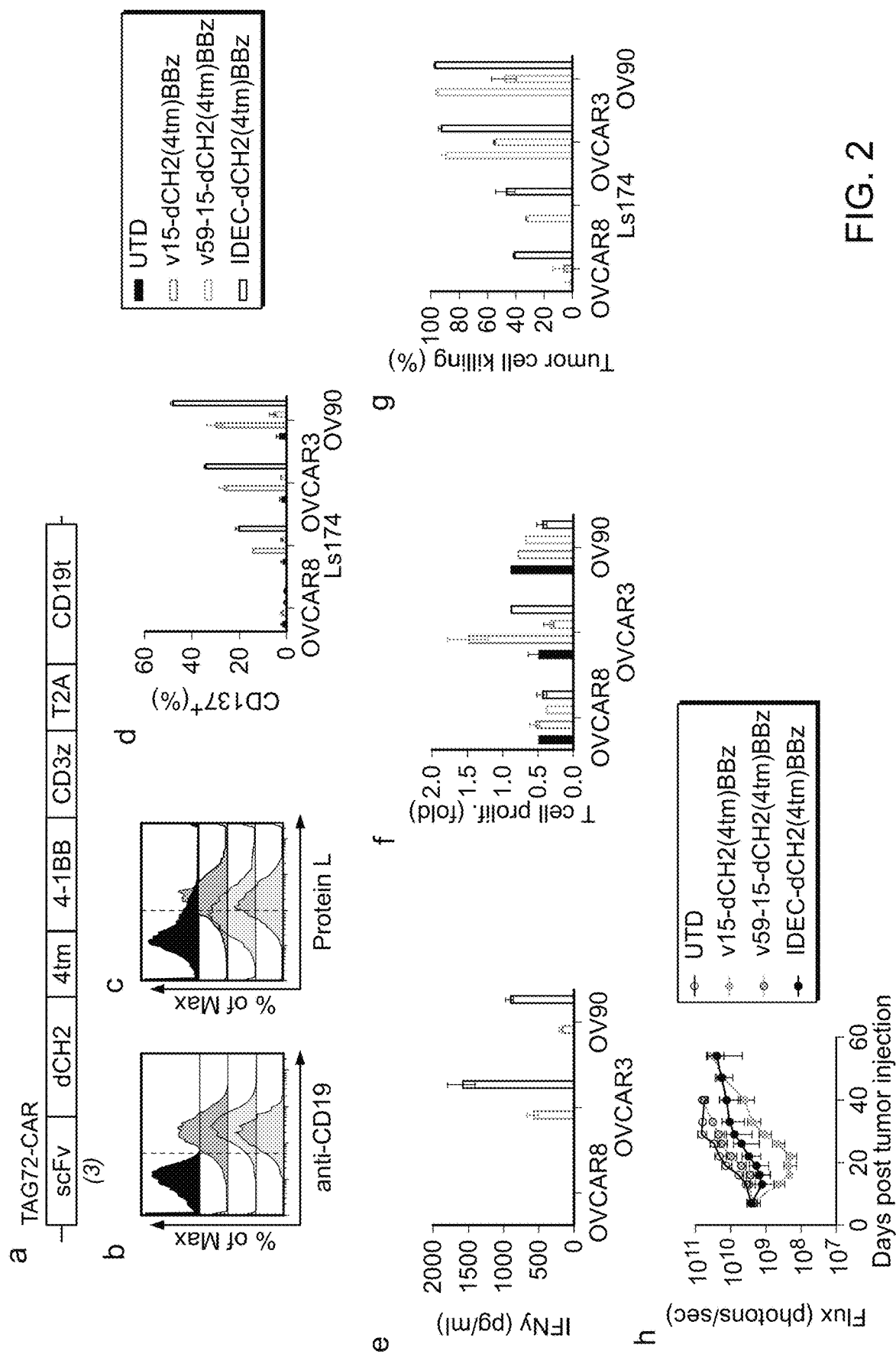
FIG. 2. In vitro and in vivo analysis of TAG72-CAR T cells with varying scFv. (a) Diagram of the lentiviral construct with a TAG72-CAR containing three different humanized scFvs (based on CC49 clone) targeting TAG72, with dCH2 extracellular spacer domain (dCH2), CD4 transmembrane (4tm), and intracellular 4-1 BB costimulatory domain (BBz) followed by a cytolytic domain (CD3z). A truncated non-signaling CD19 (CD19t), separated from the CAR sequence by a ribosomal skip sequence (T2A), was expressed for identifying lentivirally transduced T cells. (b-c) Untransduced (UTD) and three TAG72-CAR T cells positively enriched for CD19t were evaluated by flow cytometry for CD19t expression to detect lentiviral transduction of CARs (b), or Protein L to detect the scFv (c). (d-g) Quantification of tumor cell killing (d), IFNγ production (e), T cell proliferation (f), and tumor cell killing (g) by the three TAG72-CAR T cells relative to UTD T cells at an E:T ratio of 1:2, following a 24 or 72 hour co-culture with antigen-positive and -negative tumor targets as described in Materials and Methods. (h) Quantification of flux from i.p. OV90(eGFP/ffluc) tumor-bearing mice treated i.p. with UTD or TAG72-CAR T cells. n=6-7 per group.

Example 1: CD28 Transmembrane in TAG72-CARs Containing a 4-1 BB Costimulatory Domain Enhances Anti-Tumor Activity In Vitro We previously generated and pre-clinically evaluated second-generation TAG72-specific CAR T cells containing a 4-1 BB intracellular costimulatory domain, which demonstrated potent anti-tumor activity using human xenograft peritoneal ovarian tumor models[31]. Based on our preclinical studies showing a lack of curative anti-tumor activity, and early phase 1 data using first-generation TAG72-CAR T cells[33] demonstrating anti-idiotype antibody production in patients likely contributing to a lack of durable therapeutic responses, we decided to redesign the CAR molecule for optimal functionality. First, we re-assessed the antigen-binding single chain variable fragment (scFv) domain of our TAG72-CAR construct in attempts to minimize the potential for anti-CAR immunogenicity and improve T cell persistence. We utilized two additional scFvs (v15, and v59-15: a fusion between v15 and v59) based on the original humanized CC49 scFv (IDEC) that through affinity maturation showed reduced potential for anti-idiotype immunogenicity[34,35]. Two of three scFvs exhibited similar high binding affinities toward TAG72 antigen (IDEC, $K_D$=33±20 nM; v15, $K_D$=35±10 nM; v59-15, not determined). For all related in vitro and in vivo studies, we use human ovarian cancer cell lines that are TAG72-negative (OVCAR8) or are varying in cell surface expression levels of TAG72 (OVCAR3, OV90, and OVCAR8-sTn) (FIG. 1). We incorporated these scFvs into the same CAR backbone we originally published[31], and evaluated their anti-tumor activity in vitro and in vivo (FIG. 2a-2h). TAG72-CAR T cells with the v15 scFv was the most optimal in terms of anti-tumor activity as compared with IDEC and v59-15.

Figure 3:
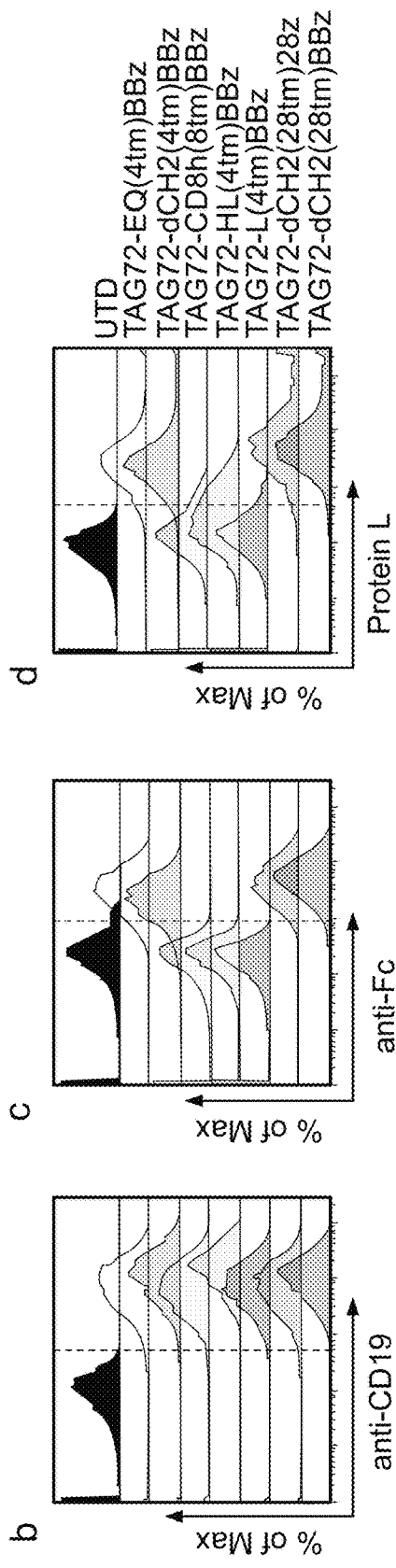
FIG. 3 In vitro optimization of TAG72-CAR T cells. (a) Diagram of the lentiviral construct with TAG72-CAR containing the humanized scFv targeting TAG72, varying extracellular spacer domains (EQ, dCH2, CD8h, HL, L), transmembrane domains (CD4tm, CD8tm, CD28tm), and intracellular costimulatory domains (4-1 BB, CD28) followed by a cytolytic domain (CD3z). A truncated non-signaling CD19 (CD19t), separated from the CAR sequence by a ribosomal skip sequence (T2A), was expressed for identifying lentivirally transduced T cells. (b-d) Untransduced (UTD) and 7 different TAG72-CAR T cells positively enriched for CD19t were evaluated by flow cytometry for CD19t expression to detect lentiviral transduction of CARs (b), fragment constant (Fc) derived spacer containing CARs (c), or Protein L to detect the scFv (d). (e-j) In vitro tumor cell killing activity relative to UTD (e), expression of CD137 activation and PD-1 exhaustion (f-g), and T cell proliferation in fold change (h) by flow cytometry, and IFNγ and IL-2 cytokine production by ELISA (i-j), of CAR T cells against tumor targets (TAG72− OVCAR8; TAG72+ OVCAR3, OV90, and OVCAR8-sTn) after 72 hours of coculture at an effector:target (E:T) ratio of 1:4. (k) TAG72-CAR T cell killing of OV90 cells measured by xCELLigence over 10 days (E:T=1:20). (l) Schema of repetitive tumor cell challenge assay (top). TAG72-CAR T cells were cocultured with OV90 cells (E:T=1:2) and rechallenged with OV90 cells every two days. Remaining viable tumor cells and fold change in TAG72-CAR T cells were quantified as described in Materials and Methods prior to each tumor cell rechallenge.
Figure 3:
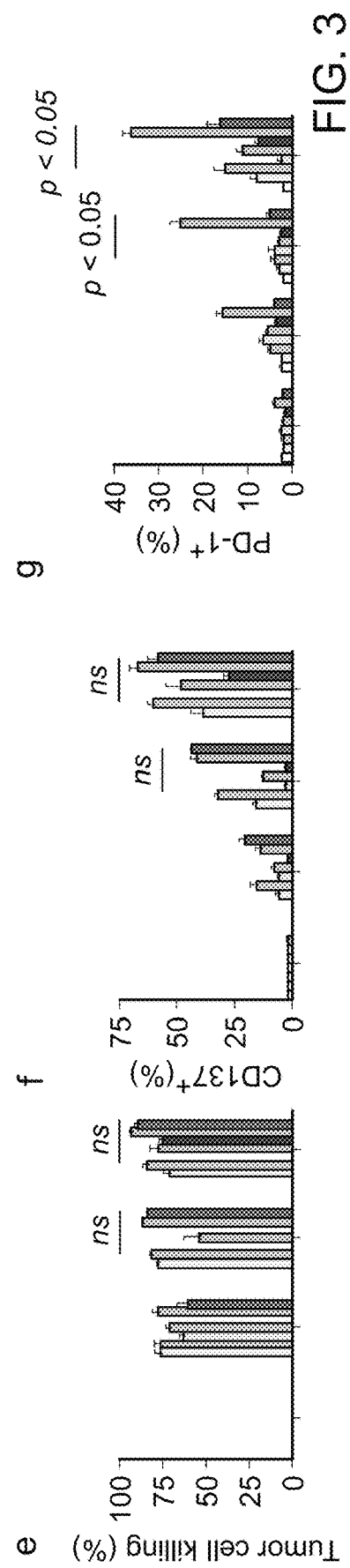
Figure 3:
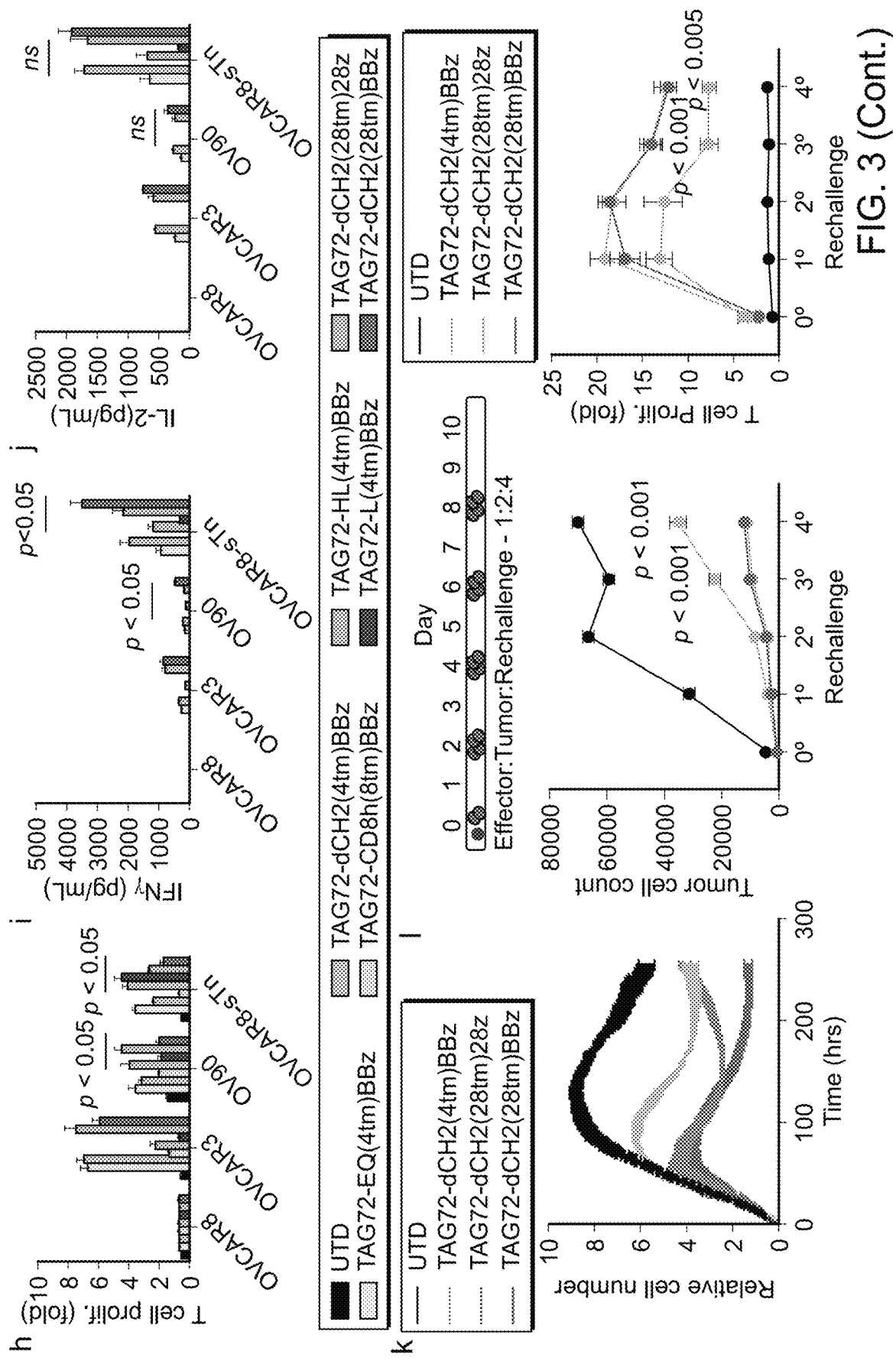

Next, we generated seven v15 scFv-based TAG72-CAR constructs with varying extracellular spacer domains and lengths (termed EQ, dCH2, CD8h, HL, and L), transmembrane domains (CD4tm, CD8tm, CD28tm), and intracellular costimulatory domains (CD28, 4-1 BB) (FIG. 3a). While all seven CAR molecules comparably expressed CD19t marker, we saw higher cell surface CAR expression with Fc-derived spacers (EQ, dCH2), as measured by Protein L staining of the scFv, which closely matched the staining pattern using anti-Fc antibodies to detect the extracellular spacer domain (FIG. 3b-3d and FIGS. 18a, 18b, and 18d). The three TAG72-CAR leads (dCH2(28tm)28z, dCH2(4tm)BBz, and dCH2(28tm)BBz) showed highest T cell activation and cytokine production. Additionally, we showed the greatest PD-1 exhaustive phenotype in CD28 costimulatory domain-containing CAR T cells (FIG. 18c), in line with previous reports using other CARs. Interestingly, we showed the lowest PD-1 and highest IFNγ with TAG72-CAR T cells that contained the CD28tm and 4-1 BB costimulatory domain. Some of these data were confirmed using HER2-CAR T cells, showing the greatest tumor cell killing, highest CD137 activation, and enhanced antigen-dependent T cell proliferation when CD28tm was coupled with the 4-1 BB costimulatory domain (FIG. 18e-18h).

We next evaluated cytotoxicity function of these TAG72-CAR T cells using in vitro coculture killing assays against cancer cell lines with varying TAG72 expression. In general, we found that TAG72-CAR T cells containing the dCH2 spacer domain showed superior functionality with the greatest tumor cell killing, highest CD137 activation, reduced PD-1 expression, enhanced antigen-dependent T cell proliferation, and robust IFNγ and IL-2 cytokine production (FIG. 3e-i). The three TAG72-CAR leads (dCH2(4tm)BBz, dCH2 (28tm)BBz, and dCH2(28tm)28z) showed highest antigen density-dependent T cell activation and cytokine production. Additionally, we showed the greatest PD-1 exhaustive phenotype in CD28 costimulatory domain-containing CAR T cells, similar to prior reports with other CARs[16,36-38]. Unexpectedly, while TAG72-CAR variants with CD8h and HL spacers showed an apparent lack of CAR cell surface expression, they showed varying tumor cell killing potential with some capacity, albeit suboptimal, to induce antigen-dependent T cell proliferation. Finally, we showed the lowest PD-1 expression and highest IFNγ production with our TAG72-CAR T cells that contained the CD28tm and 4-1 BB costimulatory domain.

From these studies, we proceeded to further "stress-test" the three TAG72-CAR T cell lead candidates. We first evaluated cytotoxicity potential of CAR T cells over an extended 10-day coculture assay with OV90 tumor cells. Using xCELLigence as a readout, TAG72-CAR T cells containing the CD28tm and 4-1 BB costimulatory domain displayed the greatest anti-tumor activity (FIG. 3k). We then performed recursive tumor cell killing assays by rechallenging TAG72-CAR T cells with OV90 tumor cells. We observed two intriguing patterns; both 4-1 BB costimulatory domain-containing CAR showed superior antigen-dependent T cell expansion profiles, whereas the CD28 transmembrane domain-containing CAR T cells achieved better control of tumors over the rechallenge time points (FIG. 3l). Collectively, our in vitro studies have identified three TAG72-CAR T cell lead candidates with potent but varying anti-tumor functional profiles, which we selected for further assessment of their in vivo preclinical therapeutic activity.

Figure 4:
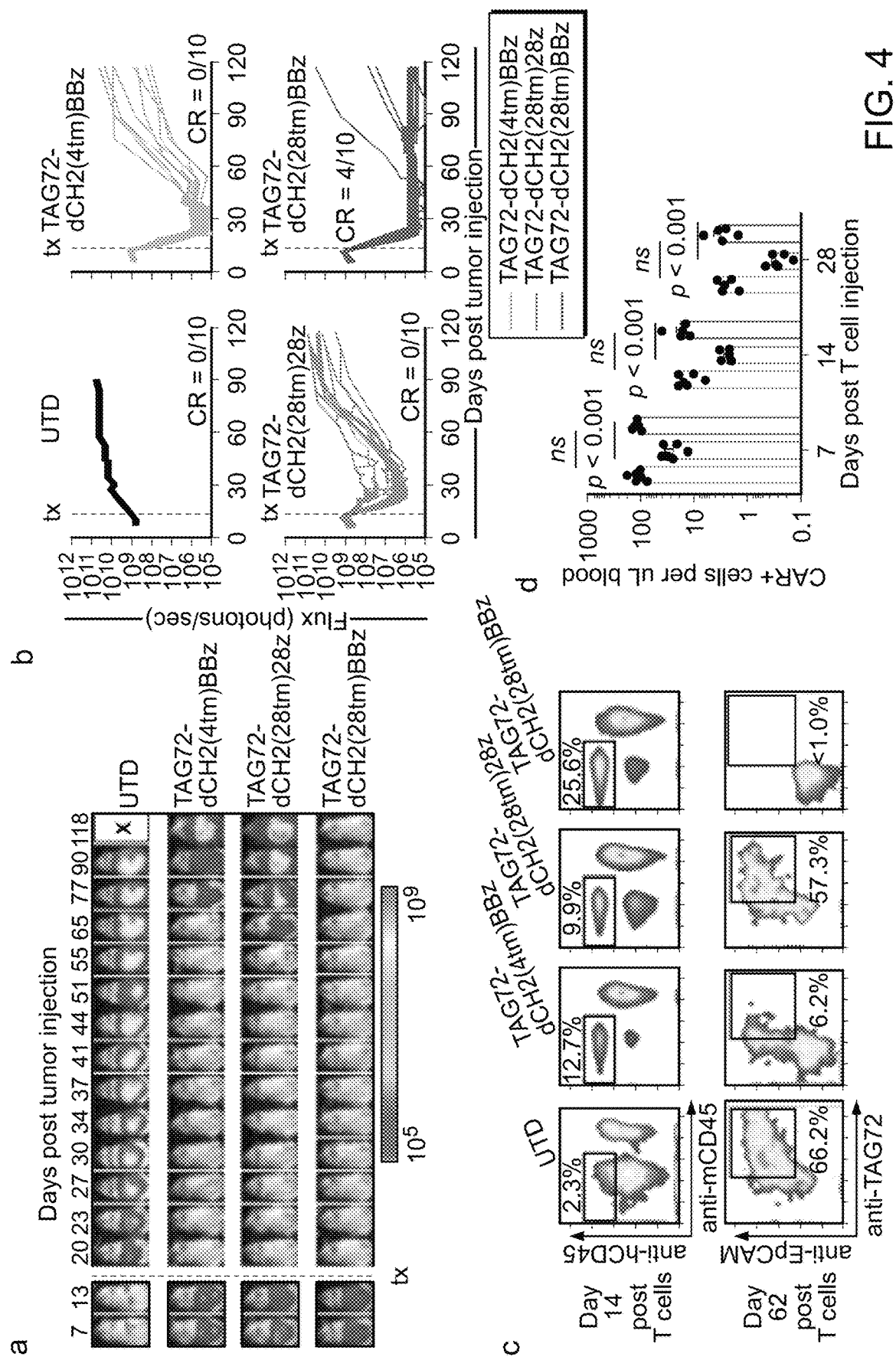
FIG. 4 Locoregional intraperitoneal delivery of TAG72-dCH2(28tm)BBz CAR T cells reduces tumor burden and extends overall survival in vivo. (a) Bioluminescent flux imaging of intraperitoneal (i.p.) OVCAR3 (eGFP/ffluc) tumor-bearing female NSG mice treated i.p. with UTD or indicated TAG72-CAR T cells. (b) Quantification of flux (individual mice in each group) from treated OVCAR3 tumor-bearing mice. UTD (n=8/group); TAG72-CAR T cells (n=10/group). (c) Flow cytometric analysis of the frequency of human CD45+ (hCD45) and mouse CD45+ (mCD45) cells in the peritoneal cavity of tumor-bearing mice at day 14 post-treatment (top); human epithelial cell adhesion molecule+ (EpCAM) and tumor associated glycoprotein-72+ (TAG72) tumor cells in the i.p. cavity of tumor-bearing mice at day 62 post-treatment (bottom). (d) Quantification of TAG72-CAR T cells per uL of peripheral blood at 7, 14, and 28 days post-treatment. N=5/group.

Example 2: CD28 Transmembrane Domain in 4-1 BB-Based TAG72-CAR T Cells Induces Durable Therapeutic Responses In Vivo Anti-tumor efficacy of these three TAG72-CAR leads was evaluated using previously established human peritoneal ovarian tumor xenograft models[31]. At day 14 following intraperitoneal (i.p.) OVCAR3 tumor injection, mice were treated with untransduced (UTD), TAG72-dCH2(4tm)BBz, TAG72-dCH2(28tm)28z, or TAG72-dCH2(28tm)BBz CAR T cells (5.0×10$^6$) by regional i.p. delivery. Dramatic anti-tumor responses were shown with all three CAR T cells, which was sustained for up to 6 weeks in treated mice (FIG. 4a). However, we observed tumor recurrences after 6-8 weeks post-treatment in mice treated with TAG72-dCH2 (4tm)BBz or TAG72-dCH2(28tm)28z CAR T cells, whereas TAG72-dCH2(28tm)BBz durably controlled tumors resulting in 4 out of 10 mice achieving complete therapeutic responses (FIG. 4b).

Figure 5:
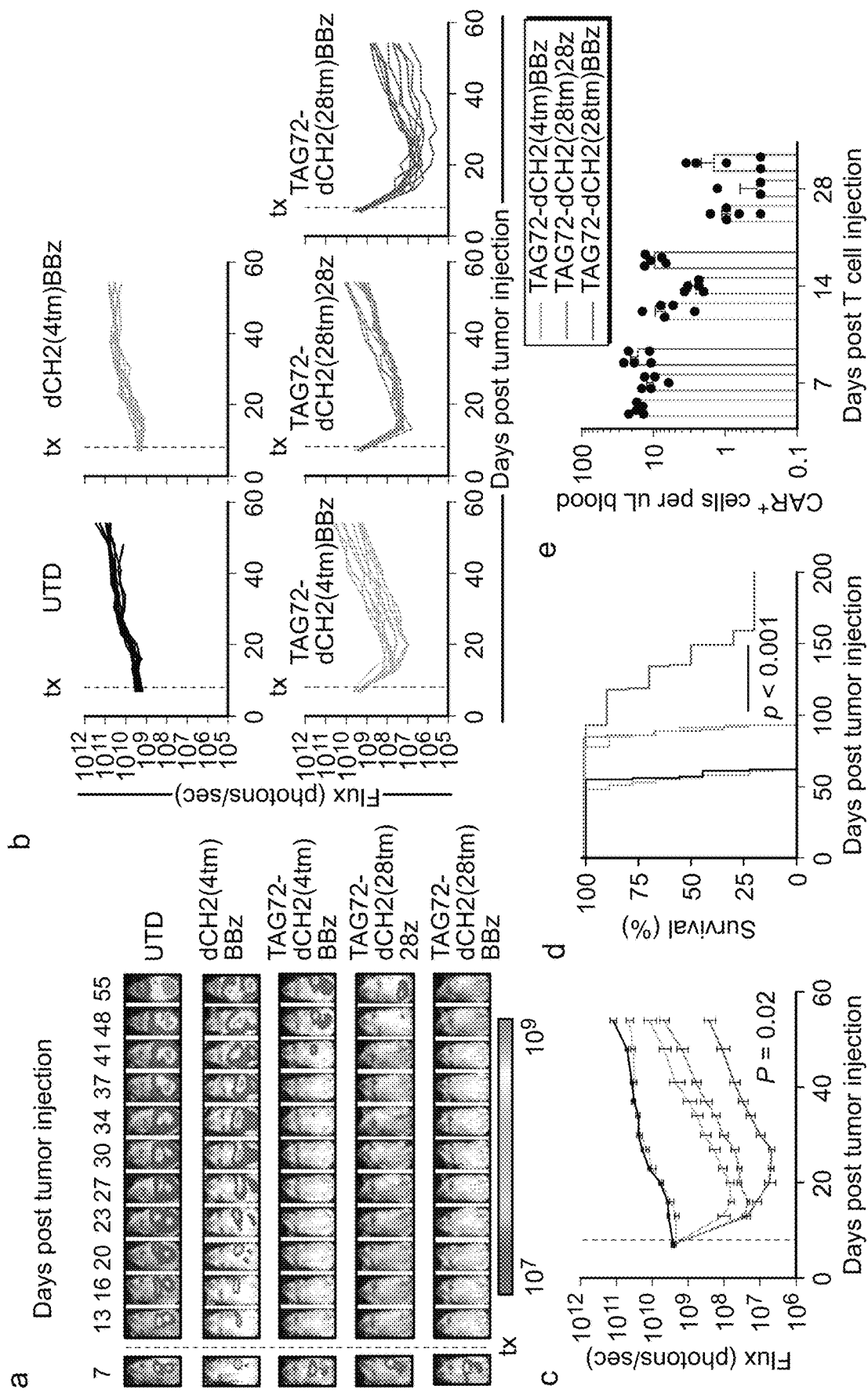
FIG. 5 Regional intraperitoneal delivery of TAG72-dCH2 (28tm)BBz CAR T cells reduces tumor burden and extends overall survival in vivo. (a) Bioluminescent flux imaging of mice treated i.p. with UTD or TAG72-CAR T cells. (b-c) Quantification of flux (b, individual mice per group; c, averages) from i.p. OV90(eGFP/ffluc) tumor-bearing mice treated i.p. with UTD or TAG72-CAR T cells. n=9 mice per group. (d) Kaplan-Meier survival for UTD, scFv-less, and TAG72-CAR T cell treated mice. n=8-9 mice/group. (e) Quantification of TAG72-CAR T cells per uL of peripheral blood at 7, 14, and 28 days post-treatment. n=5/group.

To uncover the potential differences observed between the three TAG72-CAR T cell leads, we quantified CAR T cells in the peritoneal ascites and peripheral blood of mice following therapy. CAR T cells were seen in peritoneal ascites in treated mice, with TAG72-dCH2(28tm)BBz CAR T cells showing the greatest proportion of cells collected from the ascites 14 days after CAR T cell injection, compared with the other two CAR T cells (FIG. 4c). We additionally collected peritoneal ascites at 62 days post-treatment, at the time of tumor recurrences, and showed elimination of TAG72+ tumor cells in TAG72–dCH2(28tm) BBz CAR T cell-treated mice, but the presence of TAG72+ tumor cells with the other two CAR T cells (FIG. 4c). We observed similar number of 4-1 BB costimulatory domain-containing CAR T cells in the blood of mice at all three timepoints, higher than CD28 costimulatory domain-containing CAR T cells (FIG. 4d). These data largely matched the T cell proliferation pattern in our in vitro functional assays. We further observed similar anti-tumor kinetics of the three CAR T cell lead candidates using a second, more aggressive, human OV90 peritoneal ovarian tumor xenograft model (FIG. 5).

To better address potential safety concerns of this optimized TAG72–CAR containing a new anti-TAG72 scFv and CAR backbone, we evaluated the on- and off-target normal cell killing potential of TAG72–dCH2(28tm)BBz CAR T cells. Little to no TAG72 expression was observed across 10 primary human normal cells evaluated by flow cytometry, with minimal CD137+ T cell activation and cell killing by TAG72–CAR T cells, a finding that was consistent across five independent human CAR T cell donors (FIG. 6). In sum, the TAG72–dCH2(28tm)BBz CAR construct showed the most optimal anti-tumor functionality in vitro with safe, potent, and durable anti-tumor efficacy in vivo.

Figure 7:
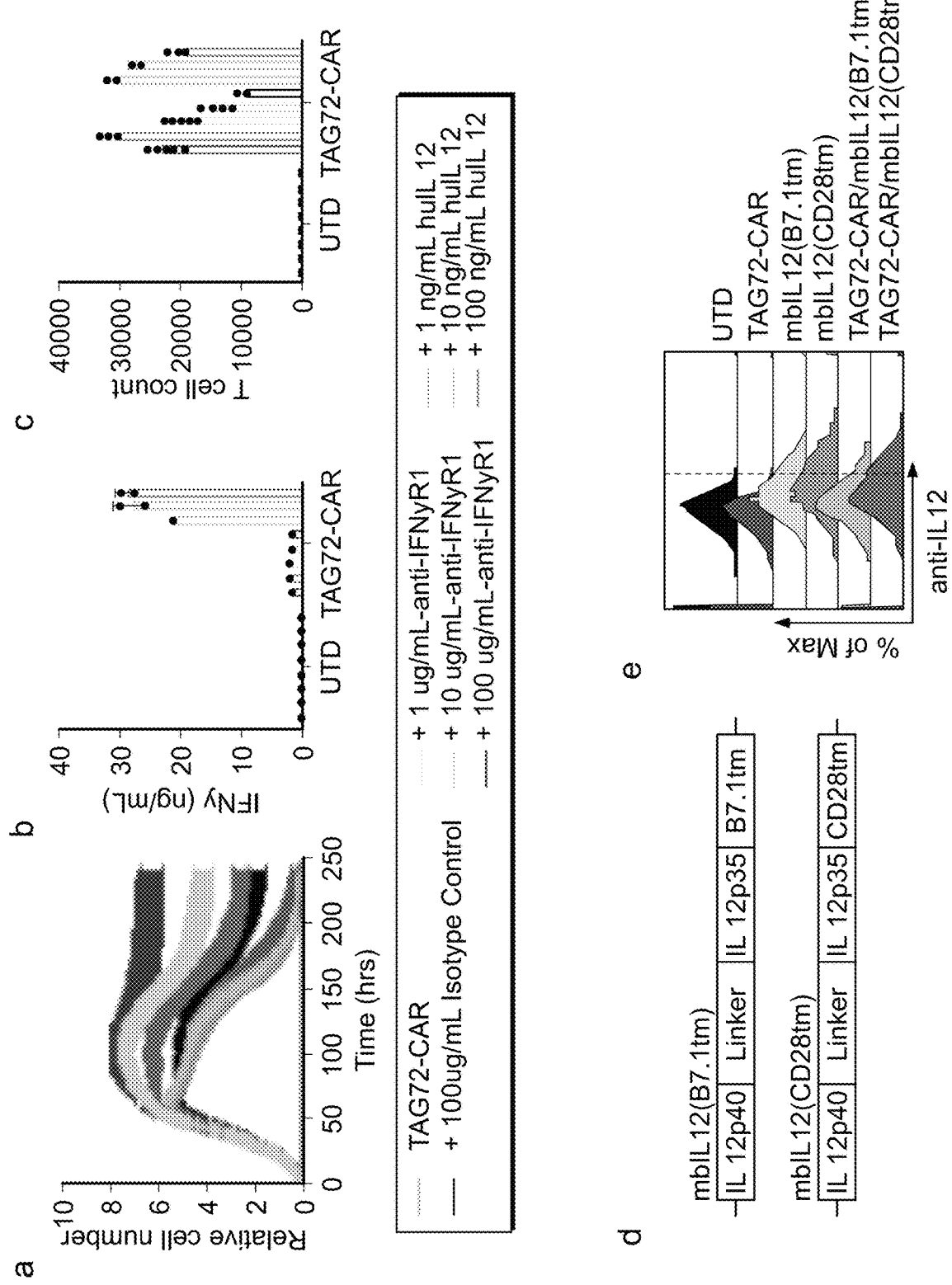
FIG. 7 Membrane-bound IL-12 engineered TAG72-CAR T cells induce higher IFNγ, T cell expansion, and anti-tumor activity in vitro. (a-c) Tumor cell killing of OV90 cells by TAG72-CAR T cells (E:T=1:20) with addition of varying concentrations of anti-IFNγR1 blocking antibody, isotype control, and recombinant human IL-12 cytokine measured by xCELLigence over 10 days (a). At day 10, IFNγ levels in supernatants were quantified by ELISA (b) and remaining T cell counts were analyzed by flow cytometry (c). (d-h) Diagram of the lentiviral construct with two versions of membrane-bound IL-12 (mbIL12) containing B7.1 or CD28 transmembrane domains (d). Flow cytometric analysis of IL-12 surface expression on indicated T cells (e). TAG72-CAR/mbIL12 T cell killing of OV90 cells (E:T=1:20) measured by xCELLigence over 10 days (f). At day 10, remaining T cell counts were analyzed by flow cytometry (g) and IFNγ levels in supernatants were quantified by ELISA (h).
Figure 7:
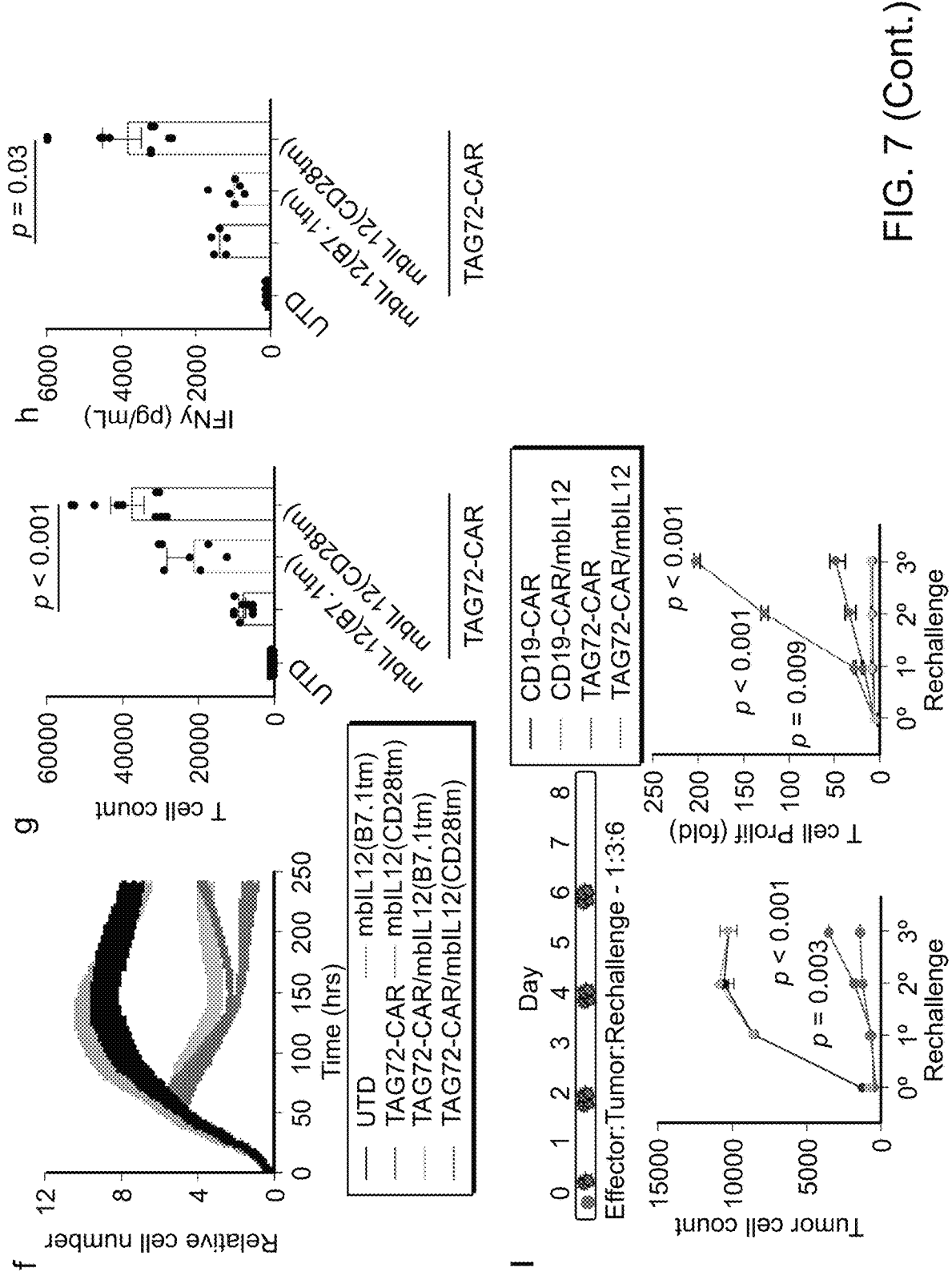

Example 3: IL-12/IFNγ Signaling Regulates the Anti-Tumor Activity of CAR T Cells Based on accumulating evidence that IFNγ signaling impacts therapeutic activity of CAR T cells[39-41] along with our observation that TAG72–dCH2(28tm)BBz CAR T cells secreted the highest levels of IFNγ in our studies, we hypothesized that IFNγ signaling contributed to the superior anti-tumor activity of TAG72–dCH2(28tm)BBz CAR T cells. To test this hypothesis, we inhibited IFNγ signaling using an anti-IFNγR1 blocking antibody or enhanced IFNγ secretion with a human recombinant interleukin-12 (IL-12) in our extended in vitro coculture tumor cell killing assay (FIGS. 19a and 7a-c). Strikingly, we saw dose-dependent dampening of tumor cell killing with blockade of IFNγ signaling using OV90 tumors 234 cells (FIG. 19b, left and FIG. 7A) and OVCAR3 tumor cells (FIG. 8). We also observed dose-dependent enhancement of tumor cell killing with increasing concentrations of recombinant huIL12, which resulted in increased production of IFNγ by CAR T cells as determined by ELISA at the assay endpoint (FIG. 19b, right and 2c). We also observed dose-dependent enhancement of tumor cell killing with increasing concentrations of recombinant huIL-12, which resulted in the significant secretion of IFNγ by CAR T cells as determined by ELISA at the assay endpoint (FIG. 7b). Interestingly, only modest impact was observed in T cell proliferation following IFNγ blockade or addition of huIL-12 in this assay (FIG. 7c). We further corroborated our findings using a recursive tumor cell killing assay, showing a requirement of IFNγ in promoting sustained anti-tumor activity in vitro (FIG. 9).

We sought to better understand the signaling kinetics downstream of IL-12 and in the context of CAR T cell antigen stimulation. We first optimized an assay to confirm phosphorylated STAT4 (pSTAT4) downstream of huIL12 in TAG72–CAR T cells. Interestingly, we observed that while pSTAT4 levels peaked at 1 hr and declined over the 24 hr time course with recombinant huIL12 alone; pSTAT4 was sustained over the 24 hr period in CAR T cells that were stimulated with plate-bound TAG72 antigen and huIL12 in combination (FIGS. 10A-10B). These data suggest that IL-12 signaling enhanced CAR T cell 247 activation and cytotoxicity, and conversely CAR T cell activation enhances persistent IL12/pSTAT4 signaling Example 4: Engineered Membrane-Bound IL-12 Signaling Drives Robust CAR T Cell-Mediated Tumor Cell Killing and Antigen-Dependent T Cell Proliferation Building on our in vitro findings that IL-12-induced IFNγ signaling is critical for CAR T cell anti-tumor activity, we engineered IL-12 into our TAG72–CAR T cells. Due to the potential off-target toxicity induced by secreted IL-12[42], we aimed to spatially restrict IL-12's effect by building membrane-bound IL-12 (mbIL12) constructs with varying transmembrane domains (FIG. 7d). When we checked for their cell surface expression, we observed slightly enhanced expression of mbIL12(CD28tm) (SEQ ID NO: 6 or 7) compared to mbIL12(B7.1tm), although both showed appreciable expression on TAG72–CAR T cells (FIG. 7e). We then evaluated tumor cell killing activity of TAG72–CAR T cells expressing either of the two versions of mbIL12, and found that TAG72–CAR/mbIL12(CD28tm) T cells displayed the highest tumor cell killing activity, T cell expansion and IFNγ production (FIG. 7f-7h). In these in vitro assays, the T cell cytotoxicity benefits with mbIL12 relied on IFNγ signaling (FIG. 23d). Similar enhancement of activation and IFNγ production with mbIL12 was shown against human patient-derived TAG72+ gastric and ovarian cancer ascites cells, with little to no impact on targeting of normal primary human cells (FIG. 23a-23c). T cell functional benefits were also observed using HER2− and PSCA-targeting CAR T cells engineered with mbIL12(CD28tm) (FIG. 14a-14h). mbIL12-engineered CAR T cells showed little/no changes in CD4/CD8 ratios, or markers of naïve/memory phenotypes (CD62L, 269 CCR7) in the in vitro functional assays (FIG. 14i-14k). We further assessed activity of CAR T cells with mbIL12(CD28tm) in recursive tumor cell killing, in which we again observed enhanced tumor cell killing and CAR antigen-dependent T cell expansion over multiple rechallenge time points (FIG. 7i).

We then compared the expression of cell-surface mbIL12 on TAG72–CAR T cells that were rested in the absence of serum or exogenous cytokines prior to stimulation with plate-bound TAG72 antigen or control antigen. Without T cell stimulation, cell-surface mbIL12 was detected at low levels on T cells, but was rather found largely intracellularly (FIGS. 10c-10d). We showed comparable mRNA transcripts of mbIL12 in stimulated and non-stimulated T cells, suggesting that low cell-surface mbIL12 expression was likely due to subcellular localization and not driven by differential EF1alpha promoter activity (FIG. 10h). Interestingly, significant dose-dependent increases in cell-surface expression of mbIL12 was observed in antigen-stimulated CAR T cells, in particular in CD137+-activated T cell subsets (FIG. 10d-10e).

Example 5: Antigen-Dependent IL-12 Signaling in CAR T Cells

We sought to better understand the signaling kinetics downstream of IL-12 with phosphoflow cytometry. We first optimized an assay to confirm phosphorylated STAT4 (pSTAT4) downstream of recombinant human IL-12 (huIL12) in TAG72–CAR T cells. Interestingly, we observed that while pSTAT4 levels peaked at 1 hr and declined over the 24 hr timecourse with recombinant huIL12 alone, pSTAT4 was sustained over the 24 hr period in CAR T cells that were stimulated with plate-bound TAG72 antigen and huIL12 in combination (FIG. 10a-b). We then compared the expression of cell surface mbIL12 on TAG72-CAR T cells that were rested in the absence of serum or exogenous cytokines prior to stimulation with plate-bound TAG72 antigen or control antigen. We observed that without stimulation, mbIL12 was detected at very low levels in engineered T cells. However, a significant increase in cell surface expression of mbIL12 was seen in antigen-stimulated TAG72-CAR T cells (FIG. 10c). Next, we interrogated pSTAT4 expression in TAG72-CAR/mbIL12 T cells in response to CAR stimulation. We observed the expected phosphorylation of STAT3 in response to TAG72 antigen in both TAG72-CAR and TAG72-CAR/mbIL12 T cells, which was only slightly activated by huIL12. However, CAR stimulation showed dose-dependent increases in pSTAT4 in TAG72-CAR/mbIL12 T cells compared to TAG72-CAR T cells alone (FIG. 10d). We further evaluated the potential for trans signaling in TAG72-CAR/mbIL12 T cells. We transduced HT1080 (TAG72-) cells with mbIL12 and cocultured them with T cells in the presence of soluble CD3/CD28 stimulation. Increased pSTAT4 in T cells was observed when cultured with both HT1080-mbIL12 and soluble CD3/CD28 and not with HT1080-mbIL12 alone or HT1080-WT with CD3/CD28 (FIG. 10e). Collectively, these data suggest that mbIL12 engineered CAR T cells demonstrate improved in vitro anti-tumor activity and unexpectedly rely on CAR antigen stimulation, which we termed antigen-dependent IL-12 signaling.

Next, we interrogated downstream pSTAT4 expression in TAG72-CAR/mbIL12 T cells in response to CAR stimulation. We observed the expected phosphorylation of STAT3 in response to TAG72 antigen in both TAG72-CAR and TAG72-CAR/mbIL12 T cells, which was only slightly activated by huIL12. However, CAR stimulation showed dose-dependent increases in pSTAT4 in TAG72-CAR/mbIL12 T cells compared to TAG72-CAR T cells alone (FIG. 1f). We further evaluated the potential for trans signaling in TAG72-CAR/mbIL12 T cells. We transduced HT1080 (TAG72-) cells with mbIL12 and co-cultured them with T cells in the presence of soluble CD3/CD28 stimulation. Increased pSTAT4 in T cells was observed when cultured with both HT1080-mbIL12 and soluble CD3/CD28 and not with HT1080-mbIL12 alone or HT1080-WT with CD3/CD28 (FIG. 10g). Anti-tumor activity was further assessed in recursive tumor cell killing assays, in which we again observed enhanced tumor cell killing and CAR antigen-dependent T cell expansion over multiple rechallenge timepoints in CAR T cells engineered with mbIL12 (FIG. 7i). Importantly, no expansion or survival benefits were observed in the absence of CAR antigen stimulation (FIGS. 13a-13b). Collectively, these data suggest that mbIL12-engineered CAR T cells demonstrate improved in vitro anti-tumor activity and unexpectedly rely on CAR antigen stimulation, which we termed antigen-dependent IL-12 signaling.

Example 6: Superior Anti-Tumor Activity by Antigen-Dependent IL-12 Signaling in CAR T Cells We next evaluated the therapeutic potential of TAG72-CAR T cells with antigen-dependent IL-12 signaling. Using the i.p. OVCAR3 tumor xenograft model, mice treated with TAG72- CAR/mbIL12 T cells sustained more durable anti-tumor responses as compared to TAG72- CAR T cells, achieving a greater incidence of durable complete responses (FIG. 11a-b). Importantly, tumor-bearing mice treated with CD19-CAR T cells and CD19-CAR/mbIL12 T cells showed little differences in therapy, supporting the antigen-dependent nature of mbIL12. We observed a higher frequency of hCD45+ cells in the peritoneal ascites of mice treated with TAG72-CAR/mbIL12 T cells as compared to mice treated with TAG72-CAR T cells alone at 2 and 4 weeks post-treatment (FIGS. 11c-11d and 19c-19d). We also observed significantly higher and sustained levels of TAG72-CAR/mbIL12 T cells in peripheral blood as compared with TAG72-CAR T cells alone (FIGS. 11d and 19d). We replicated these findings using the more challenging i.p. OV90 tumor xenograft model, where the differences in therapy and T cell persistence between TAG72-CAR and TAG72-CAR/mbIL12 T cells were even more pronounced (FIG. 11e-f).

Example 7: Improved Systemic Disease Targeting by CAR T Cells with Antigen-Dependent IL-12 Signaling One prevailing argument against the locoregional administration of CAR T cells is their potential spatial confinement, thereby preventing systemic therapy in patients with widespread metastatic disease[43]. However, our data suggest that regional intraperitoneally-administered mbIL12-engineered CAR T cells may have a greater capacity to target disease outside of the peritoneum. To test this, we established a xenograft OV90 tumor model with both a regional i.p. and systemic s.c. tumor in the same mouse. OV90 (fluc-negative) tumor cells were injected subcutaneously (s.c.) to track with calipers measurement, and OV90 (eGFP/ffluc-expressing) tumor cells were i.p. injected and tracked with bioluminescent flux imaging (FIG. 12a). As we observed in previous experiments, i.p. anti-tumor responses were greater in mice regionally treated with TAG72-CAR/mbIL12 T cells as compared to TAG72- CAR T cells alone (FIG. 12b-c). While s.c. tumors initially regressed similarly in both treatment groups, all tumors recurred following TAG72-CAR T cell treatment alone, whereas s.c. tumors were completely eradicated in all mice followingTAG72-CAR/mbIL12 T cell treatment (FIG. 12d). We corroborated this phenomenon by again observing higher levels of CAR T cells in the peripheral blood and peritoneal ascites of mice treated with TAG72- CAR/mbIL12 T cells (FIG. 12e-f). Furthermore, immunohistochemistry (IHC) analysis of s.c. tumors at day 12 post treatment demonstrated significantly greater infiltration of TAG72- CAR/mbIL12 T cells as compared with TAG72-CAR T cells alone (FIG. 12g). Overall, these data support logoregional delivery of CAR T cells with engineered antigen-dependent IL-12 signaling in durable targeting both regional and systemic disease.

Example 8: Membrane-Bound IL-12 Improves Anti-Tumor Activity of Various CAR

We further engineered CAR T cells targeting HER2 or PSCA, with a membrane-bound IL-12 molecule mbIL12 (CD28tm) (SEQ ID NO:F) and showed similar improvements in anti-tumor activity (FIG. 14a-f). To extend our finding that mbIL12 signaling enhances regional to systemic disease targeting by CAR T cells, we used the patient-derived HER2+ BBM1 tumor model we previously published in developing our HER2-CAR T cells. Using this model system, we established a BBM1 tumor xenograft model with both regional intracranial (i.c.) brain metastasis and intratibial (i.ti.) bone metastasis in the same mouse.

BBM1-ZsGreen-ffluc tumor cells were i.e. and i.ti. injected and tracked with bioluminescent flux imaging (FIG. 16a). Mice were treated with a single dose of HER2–CAR T cells by regional intracerebroventricular (i.c.v.) delivery corresponding to day 8 post i.e. tumor injection and day 23 post i.ti. tumor injection. We observed potent therapeutic responses in the brain using either HER2–CAR T cells alone or HER2–CAR T cells engineered with mbIL12 (FIGS. 16b and 16c, top row). However, only mbIL12-engineered HER2–CAR T cells demonstrated curative responses in i.ti. bone metastases in the majority of treated mice, compared with heterogeneous responses with HER2–CAR T cells alone (FIGS. 16b and 16c, bottom row). Similar to our observations in the dual-tumor ovarian cancer model above, we observed significant expansion and greater persistence of HER2–CAR/mbIL12 T cells in the peripheral blood of regional i.c.v. treated mice, as compared with HER2–CAR T cells alone (FIG. 16d-16e), with persisting HER2–CAR/mbIL12 T cells in the blood showing a greater central memory phenotype (FIG. 16g-16h), along with greater T cell infiltration in both brain and bone metastases (FIG. 16f). Collectively, these two models strongly support the benefits of mbIL12 in targeting systemic disease following regional administration of CAR T cells.

Example 9: mbIL12-Engineered CAR T Cells Demonstrate Safety and Efficacy in an Immunocompetent Mouse Model of Ovarian Cancer Peritoneal Metastasis The safety concerns of IL-12 have limited its therapeutic applications in humans to date. Infusion of soluble recombinant IL-12 in patients has resulted in unwanted toxicities, including colitis. Additionally, engineering adoptive T cell therapies with soluble IL-12, even under NFAT inducible promoter systems to limit IL-12 production to activated T cells has resulted in similar toxicities. To test whether mbIL12-engineered CAR T cells is a safe therapeutic approach compared with soluble IL-12, we built a fully immunocompetent mouse model of TAG72+ ovarian cancer peritoneal metastasis, along with a murine version of our TAG72–CAR and mbIL12 constructs (FIG. 20a). TAG72–CAR T cells were efficiently manufactured as previously described using retrovirus transduction of murine splenic T cells, and were further engineered to express mbIL12 (FIG. 20b-20c). Murine ID8 ovarian cancer cells were stably transduced and cloned to express TAG72 using the mouse sialyltransferase (mSTn) were used as tumor targets for our studies (FIG. 20d). Murine TAG72– CAR/mbIL12 T cells demonstrated increased activity and cytotoxicity against TAG72+ID8 tumor cells, as compared with TAG72–CAR T cells alone (FIG. 20e-20g). We observed a bias towards antigen-dependent expansion of CD8+CAR T cells, relative to the starting product, during the tumor cell killing assays in vitro (FIGS. 20c and 20h).

We performed a head-to-head safety and efficacy comparison of CAR T cells either engineered with mbIL12 or in combination with soluble IL-12 injections. TAG72+ID8 (ffluc-positive) tumor cells were injected i.p. and tracked with bioluminescent flux imaging, and on day 14 post tumor injection were regionally i.p. treated with either TAG72–CAR T cells alone, TAG72–CAR/mbIL12 T cells, or TAG72–CAR T cells along with soluble IL-12 (sIL12) injections for 5 days (FIG. 21a). Potent therapeutic responses were seen in all treated mice, but were greater in mice regionally treated with TAG72–CAR/mbIL12 T cells or TAG72–CAR T cells with sIL12, as compared to TAG72–CAR T cells alone (FIGS. 17a, 21b-21c). Interestingly, at later time points, we observed recurrences in mice treated with CAR T cells and sIL12 injections, but durable tumor control in mice treated with CAR T cells engineered with mbIL12. While IL-12 benefited CAR T cell therapy by injection or with T cell engineering, we observed significant body weight loss in mice following TAG72–CAR T cells and sIL12 injections, and not in TAG72–CAR/mbIL12 treated mice (FIGS. 17a, 21d). We confirmed systemic toxicities associated with sIL12 injections, with mice showing signs of splenomegaly (FIGS. 21e, 21k, top), signs of liver abnormalities and greater T cell infiltration in the liver (FIGS. 21f and 21k, bottom), along with increased serum ALT and AST levels and changes in peripheral blood lymphocyte counts (FIGS. 17b, 21g-21h), while no appreciable systemic effects were observed with TAG72–CAR/mbIL12 T cells. Importantly, sIL12 injections resulted in increases in systemic IFNγ levels in serum of TAG72–CAR T cell treated mice, which was undetectable in TAG72–CAR/mbIL12 treated mice (FIGS. 17c, 21i-21j). These data support the safety and efficacy of regionally administered mbIL12-engineered CAR T cells in an immunocompetent mouse tumor model.

Example 10: mbIL12-Engineered CAR T Cells Modify the Immunosuppressive Tumor Microenvironment in Peritoneal Metastasis IL-12 has numerous effects on the tumor microenvironment, including reshaping the myeloid cell compartment, promoting antigen-presentation, and enhancing adoptive T cell therapies. We therefore assessed the impact of mbIL12-engineering of CAR T cells and its role in the tumor microenvironment in the ovarian cancer peritoneal metastasis model. Peritoneal tumors harvested from mice treated with TAG72–CAR/mbIL12 T cells showed increased T cell infiltration as compared with TAG72–CAR T cells alone (FIG. 22a). At this early timepoint post therapy, both treated groups showed comparable potency in clearing tumor cells in the peritoneal ascites (FIGS. 22b-22c). We further evaluated the peritoneal ascites for changes in immune cell subsets by flow cytometry (FIG. 22l), which showed increases in overall CD45+ immune cell counts, comprised of T cells, myeloid cells, and NK cells, with little change in total B cell counts (FIGS. 22d and 22m). TAG72–CAR T cells engineered with mbIL12 showed increased persistence of CD8+ T cells in the peritoneal ascites (FIGS. 22e-22f), and a small but significant increase in CD137 activation (FIG. 22g). Interestingly, while TAG72–CAR/mbIL12 T cells persisting showed little change in CD62L+CD44+ naïve/memory phenotypes, there was an increase in naïve/memory phenotypes of non-CAR T cells in the peritoneal ascites (FIG. 22h). We then evaluate changes in the myeloid cell compartment in the peritoneal ascites, showing significant increases in total 17 F4/80+ tumor-associated macrophages (TAM), along with increases in Ly6C+ inflammatory monocytes, without changes in Ly6G+ neutrophil and CD11c+DC populations (FIG. 22i). However, we observed significant increases in MHC-II expression among the CD11c+CD103+ 414 DCs, suggesting an improved mature antigen-presenting phenotype. Collectively, these findings demonstrate beneficial modulation of the immunosuppressive tumor microenvironment in this model by mbIL12-engineered CAR T cells Materials and Methods Used in Examples Cell Lines The epithelial ovarian cancer line OVCAR3 (ATCC HTB-161) was cultured in RPMI-1640 (Lonza) containing 20% fetal bovine serum (FBS, Hyclone) and 1× antibiotic-antimycotic (1× AA, Gibco) (complete RPMI). The epithelial ovarian cancer line derived from metastatic ascites OV90 (CRL-11732) was cultured in a 1:1 mixture of MCDB 105 medium (Sigma) and Medium 199 (Thermo) adjusted to pH of 7.0 with sodium hydroxide (Sigma) and final 20% FBS and 1× AA. The epithelial ovarian cancer line OVCAR8 was a generous gift from Dr. Carlotta Glackin at City of Hope and was cultured in complete RPMI-1640. All cells were cultured at 37° C. with 5% $CO_2$. The breast-to-brain metastasis patient-derived line BBM1 was cultured as previously described[64]. The mouse ovarian cancer cell line ID8 was cultured in Dulbecco's Modified Eagles Medium (DMEM) supplemented with 10% FBS, 2 mM L-Glutamine (Fisher Scientific), and 25 mM HEPES (Irvine Scientific) (cDMEM). The human breast cancer cell line MDA-MB-468 (ATCC HTB-132) was engineered to express HER2 (Accession: NM_004448.4) under the control of the EF1a promotor via epHIV7 lentivirus transduction (468-HER2). All cells were cultured at 37° C. with 5% C02. Human primary cell lines were obtained from Cell Biologics (Human Primary Colonic Epithelial Cells H-6047, Human Primary Esophageal Epithelial Cells H-6046, Human Primary Kidney Epithelial Cells H-6034, Human Primary Ovarian Epithelial Cells H-6036, Human Primary Pancreatic Epithelial Cells H-6037, Human Primary Proximal Tubular Epithelial Cells H-6015, Human Primary Small Intestine Epithelial Cells H-6051, Human Primary Stomach Epithelial Cells H-6039), Promocell (Human Cardiac Myocytes C-12810), and Lonza (Human Bronchial Epithelial Cells CC-2541) and cultured according to vendor's specifications.

DNA Constructs, Tumor Lentiviral Transduction, and Retrovirus Production

Tumor cells were engineered to express enhanced green fluorescent protein and firefly luciferase (eGFP/ffluc) by transduction with epHIV7 lentivirus carrying the eGFP/ffluc fusion under the control of the EF1α promoter as described previously[23]. The humanized scFv sequence used in the CAR construct was obtained from a monoclonal antibody clone huCC49 that targets TAG72[31]. The extracellular spacer domain included the 129-amino acid middle-length CH2-deleted version (ΔCH2) of the IgG4 Fc spacer[31]. The intracellular co-stimulatory signaling domain contained was a 4-1 BB with a CD4 transmembrane domain. The CD3ζ cytolytic domain was previously described[31]. Variations in extracellular spacer domains, transmembrane domains, and intracellular co-stimulatory signaling domains were described previously[11,23,38]. The CAR sequence was separated from a truncated CD19 gene (CD19t) by a T2A ribosomal skip sequence, and cloned in an epHIV7 lentiviral backbone under the control of the EF1α promoter. The PSCA-BBC CAR construct was described previously[38]. The membrane-bound IL-12 (mbIL12) construct was generated using the p35 and p40 genes (p35, NC_000003.12; p40, NC_000005.10) separated by a G4S spacer (SEQ ID NO: 14), and linked to either the B7.1 or CD28 transmembrane domain. Lentivirus was generated as previously described[38]. Lentiviral titers were quantified using HT1080 cells based on CD19t or IL-12 cell surface expression using flow cytometry. Human and murine tumor cells were engineered to express enhanced green fluorescent protein and firefly luciferase (eGFP/ffluc), or ffluc alone, by transduction with epHIV7 lentivirus carrying the eGFP/ffluc fusion or ffluc alone under the control of the EF1α promoter as described previously[23]. Murine ovarian cancer cell line ID8 was also engineered to express target antigen TAG72 via transduction with epHIV7 lentivirus carrying the murine st6galnac-I gene (mSTn) under the control of the EF1a. mSTn is the unique sialyltransferase responsible for generating surface expression of aberrant glycosylation sialyl-Tn (TAG72). The humanized scFv sequence used in the CAR construct was obtained from a monoclonal antibody clone huCC49 that targets TAG7231

The extracellular spacer domain included the 129-amino acid middle-length CH2-deleted version (ΔCH2) of the IgG4 Fc spacer[31]. The intracellular co-stimulatory signaling domain contained was a 4-1 BB with a CD4 transmembrane domain. The CD3ζ cytolytic domain was previously described[31]. Variations in extracellular spacer domains, transmembrane domains, and intracellular co-stimulatory signaling domains were described previously[11,23,38]. The CAR sequence was separated from a truncated CD19 gene (CD19t) by a T2A ribosomal skip sequence, and cloned in an epHIV7 lentiviral backbone under the control of the EF1α promoter. The PSCA-BBC CAR and HER2-BBC CAR constructs were described previously[38]. The membrane-bound IL-12 (mbIL12) construct was generated using the p35 and p40 genes (p35, 532 NC_000003.12; p40, NC_000005.10) separated by a G4S spacer (SEQ ID NO: 14), and linked to either the B7.1 or CD28 transmembrane domain. Lentivirus was generated as previously described[38]. Lentiviral titers were quantified using HT1080 cells based on CD19t or IL-12 cell surface expression using flow cytometry.

The scFv sequence from the mouse anti-human TAG72 antibody clone (CC49) was used to develop the murine CAR (mTAG72–CAR) construct. The extracellular spacer domain included the murine IgG1 region followed by a murine CD28 transmembrane domain66,67. The intracellular costimulatory signaling domain contained the murine 4-1 BB followed by a murine CD3ζ cytolytic domain as previously described[68]. The CAR sequence was separated from a truncated murine CD19 gene (mCD19t) by a T2A ribosomal skip sequence. Murine membrane-bound IL12 was generated using murine p40 and p35 subunits sequences linked to a cell membrane anchoring murine CD28 transmembrane domain sequence. All retrovirus constructs were cloned into the pMYs retrovirus backbone under the control of a hybrid MMLV/MSCV promoter (Cell Biolabs Inc). Production of retrovirus used to transduce primary murine T cells were performed as previously described[69]. Retrovirus was produced by transfecting the ecotropic retroviral packaging cell line, PLAT-E, with addition of mTAG72– CAR retrovirus backbone plasmid DNA using FuGENE HD transfection reagent (Promega). Viral supernatants were collected after 24, 36, and 48 h, pooled, and stored at −80° C. in aliquots for future T cell transductions. Control non-targeting murine mPSCA-CAR was generated as previously described.[70]

T Cell Isolation, Lentiviral Transduction, and Ex Vivo Expansion

Leukapheresis products were obtained from consented research participants (healthy donors) under protocols approved by the City of Hope Internal Review Board (IRB), and enriched for T cells as previously described[38,58]. T cell activation and transduction was performed as described previously[38]. Where indicated, we performed a second lentiviral transduction followed 24 hr after the first transduction. Cells were then ex vivo manufactured, enriched for CAR, and frozen as described previously[38]. Purity and cell surface phenotype of CAR T cells were analyzed by flow cytometry using antibodies and methods as described below.

For mouse T cells, splenocytes were obtained by manual digestion of spleens from female C57BL/6j mice. Enrichment of T cells was performed by EasySep™ mouse T cell isolation kit per manufacturer's protocol (StemCell Technologies). Single or dual retroviral transductions with mTAG72-CAR, mPSCA-CAR and/or murine mbIL12 and subsequent expansion were performed as previously described, and cultured in cRPMI[69].

Flow Cytometry

For flow cytometric analysis, cells were resuspended in FACS buffer (Hank's balanced salt solution without $Ca^{2+}$, $Mg^{2+}$, or phenol red ($HBSS^{-/-}$, Life Technologies) containing 2% FBS and 1×AA). Cells were incubated with primary antibodies for 30 min at 4° C. in the dark. For secondary staining, cells were washed twice prior to 30 min incubation at 4° C. in the dark with either Brilliant Violet 510 (BV510), fluorescein isothiocyanate (FITC), phycoerythrin (PE), peridinin chlorophyll protein complex (PerCP), PerCP-Cy5.5, PE-Cy7, allophycocyanin (APC), or APC-Cy7 (or APC-eFluor780)-conjugated antibodies. Antibodies against CD3 (BD Biosciences, Clone: SK7), CD4 (BD Biosciences, Clone: SK3), CD8 (BD Bosciences, Clone: SK1), CD19 (BD Biosciences, Clone: SJ25C1), mouse CD45 (BioLegend, Clone: 30-F11), CD45 (BD Biosciences, Clone: 2D1), CD69 (BD Biosciences, Clone: L78), CD137 (BD Biosciences, Clone: 4B4-1), biotinylated Protein L (GenScript USA) (25), TAG72 (Clone, muCC49), Donkey Anti-Rabbit Ig (Invitrogen), Goat Anti-Mouse Ig (BD Biosciences), and streptavidin (BD Biosciences) were used. Cell viability was determined using 4',6-diamidino-2-phenylindole (DAPI, Sigma). Flow cytometry was performed on a MACSQuant Analyzer 10 (Miltenyi Biotec), and the data was analyzed with FlowJo software (v10, TreeStar).

For intracellular flow cytometry, CAR T cells were thawed and rested in IL-2 (50 U/mL) & IL-15 (0.5 ng/mL) overnight at $1\times10^6$ cells/mL. On the following day, CAR T cells were washed twice in 1× PBS and suspended at $1\times10^6$ cells/mL in media without serum or cytokines. $1\times10^5$ cells were plated per well in a 96-well plate to rest overnight. The next day, cells were stimulated with either soluble cytokine [IL-2 (50 U/mL), IL-15 (0.5 ng/mL), IL-12 (10 ng/mL)] or transferred to a high-binding 96-well plate pre-coated with indicated amounts of control or TAG72 antigen (BioRad). Reagents and buffers for flow cytometry processing were pre-chilled on ice unless otherwise stated. Following antigen stimulation, cells were washed with FACS buffer (supplemented with 0.1% sodium azide) and then fixed in pre-warmed 1× BD Phosflow Lyse/Fix buffer (558049) at 37° C. for 10 minutes. Cells were then washed with FACS buffer and if required, stained with the extracellular antibodies on ice for 30 minutes in the dark. Stained cells were washed and suspended in pre-chilled (-20° C.) BD Perm Buffer Ill (558050) and kept on ice for 30 minutes. Following a wash, cells were suspended in human FC block (Miltenyi Biotec Inc., FLP3330) and kept on ice for 30 minutes, washed and stained with intracellular antibodies: PE-pSTAT3, PE-pSTAT4, PE-pSTAT5 (Biolegend). Data was acquired on a MACSQuant Analyzer 16 cytometer (Miltenyi) and analyzed with FlowJo v10.8.

In Vitro Tumor Killing and T Cell Functional Assays

For tumor cell killing assays, CAR T cells and tumor targets were co-cultured at indicated effector:tumor (E:T) ratios in complete X-VIVO (for human T cell assays) or cRPMI (for murine T cell assays) without cytokines in 96-well plates for the indicated time points and analyzed by flow cytometry as described above. Tumor cells were plated overnight prior to addition of T cells. Tumor cell killing by CAR T cells was calculated by comparing CD45– negative DAPI-negative (viable) cell counts relative targets co-cultured with untransduced (UTD) T cells. For tumor cell challenge assays, TAG72-CAR T cells engineered with or without mbIL12 were co-cultured with OV90 cells at 1:2 E:T ratio and rechallenged with OV90 cells every two days for up to five times. Similarly, HER2-CAR T cells engineered with or without mbIL12 were co-cultured with 468-HER2 tumor cells at 1:10 E:T ratio and rechallenged with 468-HER2 cells every three days. Remaining viable tumor cells and T cells were quantified by flow cytometry prior to every rechallenge and two or three days after the last rechallenge with tumor cells. For xCELLigence tumor cell killing assays, CAR T cells and tumor targets were co-cultured at indicated effector:tumor (E:T) ratios in complete X-VIVO without cytokines in 96-well plates for up to 10 days and analyzed by flow cytometry as described above.

To evaluate CAR T cell activity against normal tissue, normal tissue cells were co-cultured with CAR T cells at indicated E:T ratios. Patient-derived primary gastric cancer ascites (GAS1) and ovarian cancer ascites (OAS3 and OAS4) were thawed immediately and evaluated in T cell functional assays. After 48 hours, CD137 expression and cell killing was evaluated by flow cytometry, and supernatant was collected to quantify IFNγ by ELISA For T cell activation assays, CAR T cells and tumor targets were co-cultured at the indicated E:T ratios in complete X-VIVO without cytokines in 96-well plates for the indicated time points and analyzed by flow cytometry for indicated markers of T cell activation. For T cell activation assays on plate-bound antigen, purified soluble TAG72 antigen (BioRad) was plated in duplicate at indicated TAG72 units overnight at 4° C. in 1×PBS in 96-well flat bottom high-affinity plates (Corning). Using a Bradford protein assay, the 20,000 units/mL stock solution of soluble TAG72 antigen was determined to be approximately 1.234 mg/mL of total protein. A designated number of TAG72-CAR T cells were then added in a fixed volume of 100 uL to each well and incubated for indicated times prior to collection of cells for analysis of activation markers (CD69, CD137) by flow cytometry. Supernatants were also collected for analysis of cytokine production. For T cell survival assays, T cells were plated at $1\times10^6$ cells/mL in X-VIVO 10% FBS with or without cytokines and counted every two days. Cell concentration was adjusted to $1\times10^6$ cells/mL with fresh media following each count day.

ELISA Cytokine Assays

Supernatants from tumor cell killing assays or CAR T cell activation assays on plate-bound TAG72 antigen were collected at indicated times and frozen at -20° C. for further use. Supernatants were then analyzed for secreted human IFNγ and IL-2 according to the Human IFNγ and IL-2 ELISA Ready-SET-GO!®; ELISA kit manufacturer's protocol, respectively. Plates were read at 450 nm using a Wallac Victor3 1420 Counter (Perkin-Elmer) and the Wallac 1420 Workstation software.

Western Blotting Analysis

Cell pellets were thawed on ice. After thaw, cell pellets were resuspended in RIPA buffer consisting of 25 mM Tris-HCl (pH 8.5), 150 mM NaCl, 1 mM EDTA (pH 8.0), 1% (v/v) NP-40 substitute, 0.5% (w/v) Sodium Deoxycholate, 0.1% (w/v) SDS, 10 mM NaF, 1 mM NaOV, 10 mM β-glycerophosphate, and 1× of Halt Protease and Phosphotase Inhibitor Cocktail (Thermo Scientific). Lysates were incubated on ice for 30 min then centrifuged at 17,200 g for 20 minutes at 4° C. Lysate supernatant was transferred to a new tube and analyzed for total protein concentration by Braford protein assay. Laemmli sample buffer (BioRad) containing DTT (Sigma Aldrich) was added to proportional quantities of total protein and samples were boiled at 95° C. for 5 minutes. Protein was separated on a 7.5% Criterion TGX Precast Midi Protein Gel (BioRad) using the Criterion Cell (BioRad) and transferred to 0.2 um nitrocellulose blotting membrane (Genesee) in Tris-Glycine Transfer Buffer (Thermo Scientific) using the Trans-Blot Turbo Electrophoretic Transfer Cell (BioRad). Membranes were washed in deionized water, incubated in Ponceau S solution (Sigma Aldrich) to confirm protein transfer, and then washed in Tris-buffered saline containing 0.05% Tween20 (Sigma Aldrich) (TBST) for 1 minute. Membranes were then blocked for 1 hour at room temperature in blocking buffer containing 5% PhosphoBLOCKER blocking reagent (Cell Biolabs) in TBST. After blocking, membranes were transferred to blocking buffer containing primary antibodies and incubated overnight at 4° C. All primary antibodies were sourced from Cell Signaling Technology and included actin (1:2000), p44/42 MAPK (ERK1/2) (1:1000), pp44/42 MAPK (pERK1/2) (1:1000), SLP76 (1:1000), pSLP76 (1:1000), PLCγ1 (1:1000), and pPLCγ1 (1:1000). Membranes were washed in TBST and then incubated for 45 min at room temperature in blocking buffer containing either anti-rabbit or anti-mouse HRP-linked secondary antibody (Cell Signaling Technology). Membranes were washed in TBST and imaged on the ChemiDoc Imaging System using SuperSignal chemiluminescent substrate (Thermo 684 Scientific).

In Vivo Studies

All animal experiments were performed under protocols approved by the City of Hope Institutional Animal Care and Use Committee. For in vivo intraperitoneal (i.p.) tumor studies, OVCAR3 and OV90 cells ($5.0 \times 10^6$) were prepared in a final volume of 500 uL HBSS$^{-/-}$ and engrafted in >6 weeks old female NSG mice by i.p. injection. For subcutaneous (s.c.) tumor studies, OV90 cells ($5 \times 10^6$) were prepared in a final volume of 100 uL HBSS$^{-/-}$ and injected under the skin of the abdomen of 6-8 weeks old female NSG mice. Tumor growth was monitored at least once a week via non-invasive bioluminescence imaging (Xenogen, LagoX) and flux signals were analyzed with Living Image software (Xenogen). For imaging, mice were i.p. injected with 150 uL D-luciferin potassium salt (Perkin Elmer) suspended in PBS at 4.29 mg/mouse. At day 8 for OV90 and day 14 for OVCAR3, mice were i.p. treated with indicated T cells ($5 \times 10^6$) in 500 uL final volume. Humane endpoints were used in determining survival. Mice were euthanized upon signs of distress such as a distended belly due to peritoneal ascites, labored or difficulty breathing, apparent weight loss, impaired mobility, or evidence of being moribund. At predetermined time points or at moribund status, mice were euthanized and tissues and/or peritoneal ascites were harvested and processed for flow cytometry and immunohistochemistry as described herein.

Peripheral blood was collected from isoflurane-anesthetized mice by retro-orbital (RO) bleed through heparinized capillary tubes (Chase Scientific) into polystyrene tubes containing a heparin/PBS solution (1000 units/mL, Sagent Pharmaceuticals). Total volume of each RO blood draw (approximately 120 uL/mouse) was recorded. Red blood cells (RBCs) were lysed with 1× Red Cell Lysis Buffer (Sigma) according to manufacturer's protocol and then washed, stained, and analyzed by flow cytometry as described above. Cells from peritoneal ascites were collected from euthanized mice by injecting 5 mL cold 1× PBS into the i.p. cavity, which was drawn up via syringe and stored on ice until further processing. RBC-depleted ascites cells were washed, stained, and analyzed by flow cytometry using antibodies and methods as described above.

Serum from immune competent mouse studies was collected from non-heparinized blood collected by RO bleed as described above. Blood was kept at room temperature for 30 minutes followed by centrifugation at 6000×g for 10 minutes at 4° C., then aliquoted to multiple tubes and frozen at −80° C. until used for serum cytokine ELISA or chemistry analyses. Serum chemistry analysis was performed by running samples on a VETSCAN® VS2 Chemistry Analyzer (Zoetis), using the phenobarbital chemistry panel rotor (Zoetis) for ALT and AST quantification as described by manufacturer's protocol. Complete blood counts (CBC) analysis on whole blood collected from RO bleed, as described previously, was performed using a VETSCAN® HM5 Hematology Analyzer per manufacturer's protocol.

Immunohistochemistry

Tumor tissue was fixed for up to 3 days in 4% paraformaldehyde (4% PFA, Boston BioProducts) and stored in 70% ethanol until further processing. Immunohistochemistry was performed by the Pathology Core at City of Hope. Briefly, paraffin-embedded sections (10 um) were stained with hematoxylin & eosin (H&E, Sigma-Aldrich), mouse anti-human CD3 (DAKO), mouse anti-human CD4 (DAKO), mouse anti-human CD8 (DAKO), and mouse anti-human TAG72 (AB16838, Abcam). Images were obtained using the Nanozoomer 2.0HT digital slide scanner and the associated NDP.view2 software (Hamamatzu).

Statistical Analysis

Data are presented as means±standard error mean (SEM), unless otherwise stated. Statistical comparisons between groups were performed using the unpaired two-tailed Student's t test to calculate p value, unless otherwise stated.

Additional Sequences

Examples of nucleotide sequences useful in a human mbIL-12 construct:

Promotor Ef1a (SEQ ID NO: 77)

GGATCTGCGATCGCTCCGGTGCCCGTCAGTGGGCAGAGCGCACATCGCCC

ACAGTCCCCGAGAAGTTGGGGGGAGGGGTCGGCAATTGAACCGGTGCCTA

GAGAAGGTGGCGCGGGGTAAACTGGGAAAGTGATGTCGTGTACTGGCTCC

GCCTTTTTCCCGAGGGTGGGGAGAACCGTATATAAGTGCAGTAGTCGCC

GTGAACGTTCTTTTTCGCAACGGGTTTGCCGCCAGAACACAGCTGAAGCT

TCGAGGGGCTCGCATCTCTCCTTCACGCGCCCGCCGCCCTACCTGAGGCC

GCCATCCACGCCGGTTGAGTCGCGTTCTGCCGCCTCCCGCCTGTGGTGCC

TCCTGAACTGCGTCCGCCGTCTAGGTAAGTTTAAAGCTCAGGTCGAGACC

GGGCCTTTGTCCGGCGCTCCCTTGGAGCCTACCTAGACTCAGCCGGCTCT

-continued
CCACGCTTTGCCTGACCCTGCTTGCTCAACTCTACGTCTTTGTTTCGTTT

TCTGTTCTGCGCCGTTACAGATCCAAGCTGTGACCGGCGCCTAC

GMCSFRa\ss
(SEQ ID NO: 78)
GGCTAGCGCCACCATGCTGCTGCTCGTGACCAGCCTGCTGCTGTGCGAGC

TGCCCCACCCCGCCTTTCTGCTGATCCCC hIL12\p40
(SEQ ID NO: 79)
ATATGGGAACTGAAGAAAGATGTTTATGTCGTAGAATTGGATTGGTATCC

GGATGCCCCTGGAGAAATGGTGGTCCTCACCTGTGACACCCCTGAAGAAG

ATGGTATCACCTGGACCTTGGACCAGAGCAGTGAGGTCTTAGGCTCTGGC

AAAACCCTGACCATCCAAGTCAAAGAGTTTGGAGATGCTGGCCAGTACAC

CTGTCACAAAGGAGGCGAGGTTCTAAGCCATTCGCTCCTGCTGCTTCACA

AAAAGGAAGATGGAATTTGGTCCACTGATATTTTAAAGGACCAGAAAGAA

CCCAAAAATAAGACCTTTCTAAGATGCGAGGCAAGAATTATTCTGGACG

TTTCACCTGCTGGTGGCTGACGACAATCAGTACTGATTTGACATTCAGTG

TCAAAAGCAGCAGAGGCTCTTCTGACCCCCAAGGGGTGACGTGCGGAGCT

GCTACACTCTCTGCAGAGAGTCAGAGGGGACAACAAGGAGTATGAGTA

CTCAGTGGAGTGCCAGGAGGACAGTGCCTGCCCAGCTGCTGAGGAGAGTC

TGCCCATTGAGGTCATGGTGGATGCCGTTCACAAGCTCAAGTATGAAAAC

TACACCAGCAGCTTCTTCATCAGGGACATCATCAAACCTGACCCACCCAA

GAACTTGCAGCTGAAGCCATTAAAGAATTCTCGGCAGGTGGAGGTCAGCT

GGGAGTACCCTGACACCTGGAGTACTCCACATTCCTACTTCTCCCTGACA

TTCTGCGTTCAGGTCCAGGGCAAGAGCAAGAGAGAAAAGAAAGATAGAGT

CTTCACGGACAAGACCTCAGCCACGGTCATCTGCCGCAAAAATGCCAGCA

TTAGCGTGCGGGCCCAGGACCGCTACTATAGCTCATCTTGGAGCGAATGG

GCATCTGTGCCCTGCAGT linker
(SEQ ID NO: 80)
GTTCCTGGAGTAGGGGTACCTGGGGTGGGC hIL12\p35
(SEQ ID NO: 81)
GCCAGAAACCTCCCCGTGGCCACTCCAGACCCAGGAATGTTCCCATGCCT

TCACCACTCCCAAAACCTGCTGAGGGCCGTCAGCAACATGCTCCAGAAGG

CCAGACAAACTCTAGAATTTTACCCTTGCACTTCTGAAGAGATTGATCAT

GAAGATATCACAAAAGATAAAACCAGCACAGTGGAGGCTGTTTACCATT

GGAATTAACCAAGAATGAGAGTTGCCTAAATTCCAGAGAGACCTCTTTCA

TAACTAATGGGAGTTGCCTGGCCTCCAGAAAGACCTCTTTTATGATGGCC

CTGTGCCTTAGTAGTATTTATGAAGACTCGAAGATGTACCAGGTGGAGTT

CAAGACCATGAATGCAAAGCTTCTGATGGATCCTAAGAGGCAGATCTTTC

TAGATCAAAACATGCTGGCAGTTATTGATGAGCTGATGCAGGCCCTGAAT

TTCAACAGTGAGACTGTGCCACAAAAATCCTCCCTTGAAGAACCGGATTT

-continued
TTATAAAACTAAAATCAAGCTCTGCATACTTCTTCATGCTTTCAGAATTC

GGGCAGTGACTATTGATAGAGTGATGAGCTATCTGAATGCTTCC g3 linker
GGCGGAGGG hCD28tm
(SEQ ID NO: 82)
TTCTGGGTGCTGGTGGTGGTGGGGGGGGTGCTGGCCTGCTACAGCCTGCT

GGTGACAGTGGCCTTCATCATCTTTTGGGTG hCD28 cytoplasmic end
(SEQ ID NO: 83)
CGGAGCAAGCGG Examples of nucleotide sequences useful in a murine mbIL-12 construct Retrovirus backbone Promotor LTR/gag/pol/psi+
(specific to retrovirus packaging plasmid):
(SEQ ID NO: 84)
CTAGAGAACCATCAGATGTTTCCAGGGTGCCCCAAGGACCTGAAATGACC

CTGTGCCTTATTTGAACTAACCAATCAGTTCGCTTCTCGCTTCTGTTCGC

GCGCTTCTGCTCCCCGAGCTCAATAAAAGAGCCCACAACCCCTCACTCGG

GGCGCCAGTCCTCCGATTGACTGAGTCGCCCGGGTACCCGTATTCCCAAT

AAAGCCTCTTGCTGTTTGCATCCGAATCGTGGACTCGCTGATCCTTGGGA

GGGTCTCCTCAGATTGATTGACTGCCCACCTCGGGGGTCTTTCATTTGGA

GGTTCCACCGAGATTTGGAGACCCCAGCCCAGGGACCACCGACCCCCCCG

CCGGGAGGTAAGCTGGCCAGCGGTCGTTTCGTGTCTGTCTCTGTCTTTGT

GCGTGTTTGTGCCGGCATCTAATGTTTGCGCCTGCGTCTGTACTAGTTAG

CTAACTAGCTCTGTATCTGGCGGACCCGTGGTGGAACTGACGAGTTCGGA

ACACCCGGCCGCAACCCTGGGAGACGTCCCAGGGACTTCGGGGGCCGTTT

TGTGGCCCGACCTGAGTCCAAAAATCCCGATCGTTTTGGACTCTTTGGT

GCACCCCCTAATAGGAGGGATATGTGGTTCTGGTAGGAGACGAGAACCT

AAAACAGTTCCCGCCTCCGTCTGAATTTTTGCTTTCGGTTTGGGACCGAA

GCCGCGCCGCGCGTCTTGTCTGCTGCAGCATCGTTCTGTGTTGTCTCTGT

CTGACTGTGTTTCTGTATTTGTCTGAAAATTAGGGCCAGACTGTTACCAC

TCCCTTAAGTTTGACCTTAGGTCACTGGAAAGATGTCGAGCGGATCGCTC

ACAACCAGTCGGTAGATGTCAAGAAGAGACGTTGGGTTACCTTCTGCTCT

GCAGAATGGCCAACCTTTAACGTCGGATGGCCGCGAGACGGCACCTTTAA

CCGAGACCTCATCACCCAGGTTAAGATCAAGGTCTTTTCACCTGGCCCGC

ATGGACACCCAGACCAGGTCCCCTACATCGTGACCTGGGAAGCCTTGGCT

TTTGACCCCCCTCCCTGGGTCAAGCCCTTTGTACACCCTAAGCCTCCGCC

TCCTCTTCCTCCATCCGCCCCGTCTCTCCCCCTTGAACCTCCTCGTTCGA

CCCCGCCTCGATCCTCCCTTTATCCAGCCCTCACTCCTTCTCTAGGCGCC

CCCATATGGCCATATGAGATCTTATATGGGGCACCCCCGCCCCTTGTAAA

CTTCCCTGACCCTGACATGACAAGAGTTACTAACAGCCCCTCTCTCCAAG

CTCACTTACAGGCTCTCTACTTAGTCCAGCACGAAGTCTGGAGACCTCTG

GCGGCAGCCTACCAAGAACAACTGGACCGACCGGTGGTACCTCACCCTTA

```
CCGAGTCGGCGACACAGTGTGGGTCCGCCGACACCAGACTAAGAACCTAG

AACCTCGCTGGAAAGGACCTTACACAGTCCTGCTGACCACCCCCACCGCC

CTCAAAGTAGACGGCATCGCAGCTTGGATACACGCCGCCCACGTGAAGGC

TGCCGACCCCGGGGGTGGACCATCCTCTAGACTGCCG
```

Murine IL12 (p40 subunit)
(SEQ ID NO: 85)
```
ATGTGTCCTCAGAAGCTAACCATCTCCTGGTTTGCCATCGTTTTGCTGGT

GTCTCCACTCATGGCCATGTGGGAGCTGGAGAAAGACGTTTATGTTGTAG

AGGTGGACTGGACTCCCGATGCCCTGGAGAAACAGTGAACCTCACCTGT

GACACGCCTGAAGAAGATGACATCACCTGGACCTCAGACCAGAGACATGG

AGTCATAGGCTCTGGAAAGACCCTGACCATCACTGTCAAAGAGTTTCTAG

ATGCTGGCCAGTACACCTGCCACAAAGGAGGCGAGACTCTGAGCCACTCA

CATCTGCTGCTCCACAAGAAGGAAAATGGAATTTGGTCCACTGAAATTTT

AAAAAATTTCAAAAACAAGACTTTCCTGAAGTGTGAAGCACCAAATTACT

CCGGACGGTTCACGTGCTCATGGCTGGTGCAAAGAAACATGGACTTGAAG

TTCAACATCAAGAGCAGTAGCAGTTCCCCTGACTCTCGGGCAGTGACATG

TGGAATGGCGTCTCTGTCTGCAGAGAAGGTCACACTGGACCAAAGGGACT

ATGAGAAGTATTCAGTGTCCTGCCAGGAGGATGTCACCTGCCCAACTGCC

GAGGAGACCCTGCCCATTGAACTGGCGTTGGAAGCACGGCAGCAGAATAA

ATATGAGAACTACAGCACCAGCTTCTTCATCAGGGACATCATCAAACCAG

ACCCGCCCAAGAACTTGCAGATGAAGCCTTTGAAGAACTCACAGGTGGAG

GTCAGCTGGGAGTACCCTGACTCCTGGAGCACTCCCCATTCCTACTTCTC

CCTCAAGTTCTTTGTTCGAATCCAGCGCAAGAAAGAAAAGATGAAGGAGA

CAGAGGAGGGTGTAACCAGAAAGGTGCGTTCCTCGTAGAGAAGACATCT

ACCGAAGTCCAATGCAAAGGCGGGAATGTCTGCGTGCAAGCTCAGGATCG

CTATTACAATTCCTCATGCAGCAAGTGGGCATGTGTTCCCTGCAGGGTCC

GATCC
```

Linker
(SEQ ID NO: 86)
```
GGCGGCGGCGGGAGTGGCGGCGGGGGTTCTGGCGGAGGCGGTAGC
```

Murine IL12 (p35 subunit)
(SEQ ID NO: 87)
```
AGGGTCATTCCAGTCTCTGGACCTGCCAGGTGTCTTAGCCAGTCCCGAAA

CCTGCTGAAGACCACAGATGACATGGTGAAGACGGCCAGAGAAAACTGA

AACATTATTCCTGCACTGCTGAAGACATCGATCATGAAGACATCACACGG

GACCAAACCAGCACATTGAAGACCTGTTTACCACTGGAACTACACAAGAA

CGAGAGTTGCCTGGCTACTAGAGAGACTTCTTCCACAACAAGAGGGAGCT

GCCTGCCCCACAGAAGACGTCTTTGATGATGACCCTGTGCCTTGGTAGC

ATCTATGAGGACTTGAAGATGTACCAGACAGAGTTCCAGGCCATCAACGC

AGCACTTCAGAATCACAACCATCAGCAGATCATTCTAGACAAGGGCATGC

TGGTGGCCATCGATGAGCTGATGCAGTCTCTGAATCATAATGGCGAGACT

CTGCGCCAGAAACCTCCTGTGGGAGAAGCAGACCCTTACAGAGTGAAAAT

GAAGCTCTGCATCCTGCTTCACGCCTTCAGCACCCGCGTCGTGACCATCA

ACAGGGTGATGGGCTATCTGAGCTCCGCC
``` g3 linker
```
GGCGGAGGG
``` mCD28tm
(SEQ ID NO: 88)
```
TTTTGGGCACTGGTCGTGGTTGCTGGAGTCCTGTTTTGTTATGGCTTGCT

AGTGACAGTGGCTCTTTGTGTTATCTGGACA
``` mCD28 cytoplasmic end
(SEQ ID NO: 89)
```
AATAGTAGAAGG
```

1 Frigault, M. J. & Maus, M. V. State of the art in CAR T cell therapy for CD19+ B cell malignancies. *J Clin Invest* 130, 1586-1594, doi:10.1172/JCI129208 (2020).

2 June, C. H. & Sadelain, M. Chimeric Antigen Receptor Therapy. *N Engl J Med* 379, 64-73, doi:10.1056/NEJMra1706169 (2018).

3 Hong, M., Clubb, J. D. & Chen, Y. Y. Engineering CAR-T Cells for Next-Generation Cancer Therapy. *Cancer Cell* 38, 473-488, doi:10.1016/j.ccell.2020.07.005 (2020).

4 Priceman, S. J., Forman, S. J. & Brown, C. E. Smart CARs engineered for cancer immunotherapy. *Curr Opin Oncol* 27, 466-474, doi:10.1097/CCO.0000000000000232 (2015).

5 Schmidts, A. & Maus, M. V. Making CAR T Cells a Solid Option for Solid Tumors. *Front Immunol* 9, 2593, doi:10.3389/fimmu.2018.02593 (2018).

6 Sterner, R. C. & Sterner, R. M. CAR-T cell therapy: current limitations and potential strategies. *Blood Cancer J* 11, 69, doi:10.1038/s41408-021-00459-7 (2021).

7 van der Stegen, S. J., Hamieh, M. & Sadelain, M. The pharmacology of second-generation chimeric antigen receptors. *Nat Rev Drug Discov* 14, 499-509, doi:10.1038/nrd4597 (2015).

8 Larson, R. C. & Maus, M. V. Recent advances and discoveries in the mechanisms and functions of CAR T cells. *Nat Rev Cancer* 21, 145-161, doi:10.1038/s41568-020-00323-z (2021).

9 Liu, X. et al. Affinity-Tuned ErbB2 or EGFR Chimeric Antigen Receptor T Cells Exhibit an Increased Therapeutic Index against Tumors in Mice. *Cancer Res* 75, 3596-3607, doi:10.1158/0008-5472.CAN-15-0159 (2015).

10 Heitzeneder, S. et al. GPC2-CAR T cells tuned for low antigen density mediate potent activity against neuroblastoma without toxicity. *Cancer Cell* 40, 53-69 e59, doi:10.1016/j.ccell.2021.12.005 (2022).

11 Jonnalagadda, M. et al. Chimeric antigen receptors with mutated IgG4 Fc spacer avoid fc receptor binding and improve T cell persistence and antitumor efficacy. *Mol Ther* 23, 757-768, doi:10.1038/mt.2014.208 (2015).

12 Lee, S. Y. et al. Preclinical Optimization of a CD20-specific Chimeric Antigen Receptor Vector and Culture Conditions. *J Immunother* 41, 19-31, doi:10.1097/CJI.0000000000000199 (2018).

13 Kunkele, A. et al. Functional Tuning of CARs Reveals Signaling Threshold above Which CD8+ CTL Antitumor Potency Is Attenuated due to Cell Fas-FasL-Dependent AICD. *Cancer Immunol Res* 3, 368-379, doi:10.1158/2326-6066.CIR-14-0200 (2015).

14 Fujiwara, K. et al. Hinge and Transmembrane Domains of Chimeric Antigen Receptor Regulate Receptor Expression and Signaling Threshold. *Cells* 9, doi:10.3390/cells9051182 (2020).

15. Bridgeman, J. S. et al. The optimal antigen response of chimeric antigen receptors harboring the CD3zeta transmembrane domain is dependent upon incorporation of the receptor into the endogenous TCR/CD3 complex. *J Immunol* 184, 6938-6949, doi:10.4049/jimmunol.0901766 (2010).
16. Zhao, Z. et al. Structural Design of Engineered Costimulation Determines Tumor Rejection Kinetics and Persistence of CAR T Cells. *Cancer Cell* 28, 415-428, doi:10.1016/j.ccell.2015.09.004 (2015).
17. Guedan, S. et al. Single residue in CD28-costimulated CAR-T cells limits long-term persistence and antitumor durability. *J Clin Invest* 130, 3087-3097, doi:10.1172/JCI133215 (2020).
18. Salter, A. I. et al. Phosphoproteomic analysis of chimeric antigen receptor signaling reveals kinetic and quantitative differences that affect cell function. *Sci Signal* 11, doi:10.1126/scisignal.aat6753 (2018).
19. Yu, S., Yi, M., Qin, S. & Wu, K. Next generation chimeric antigen receptor T cells: safety strategies to overcome toxicity. *Mol Cancer* 18, 125, doi:10.1186/s12943-019-1057-4 (2019).
20. Lim, W. A. & June, C. H. The Principles of Engineering Immune Cells to Treat Cancer. *Cell* 168, 724-740, doi:10.1016/j.cell.2017.01.016 (2017).
21. Bell, M. & Gottschalk, S. Engineered Cytokine Signaling to Improve CAR T Cell Effector Function. *Front Immunol* 12, 684642, doi:10.3389/fimmu.2021.684642 (2021).
22. Brown, C. E. et al. Regression of Glioblastoma after Chimeric Antigen Receptor T-Cell Therapy. *N Engl J Med* 375, 2561-2569, doi:10.1056/NEJMoa1610497 (2016).
23. Priceman, S. J. et al. Regional Delivery of Chimeric Antigen Receptor-Engineered T Cells Effectively Targets HER2(+) Breast Cancer Metastasis to the Brain. *Clin Cancer Res* 24, 95-105, doi:10.1158/1078-0432.CCR-17-2041 (2018).
24. Wang, X. et al. The Cerebroventricular Environment Modifies CAR T Cells for Potent Activity against Both Central Nervous System and Systemic Lymphoma. *Cancer Immunol Res* 9, 75-88, doi:10.1158/2326-6066.CIR-20-0236 (2021).
25. Brown, C. E. et al. Optimization of IL13Ralpha2-Targeted Chimeric Antigen Receptor T Cells for Improved Anti-tumor Efficacy against Glioblastoma. *Mol Ther* 26, 31-44, doi:10.1016/j.ymthe.2017.10.002 (2018).
26. Vitanza, N. A. et al. Locoregional infusion of HER2-specific CAR T cells in children and young adults with recurrent or refractory CNS tumors: an interim analysis. *Nat Med* 27, 1544-1552, doi:10.1038/s41591-021-01404-8 (2021).
27. Adusumilli, P. S. et al. Regional delivery of mesothelin-targeted CAR T cell therapy generates potent and long-lasting CD4-dependent tumor immunity. *Sci Transl Med* 6, 261 ra151, doi:10.1126/scitranslmed.3010162 (2014).
28. Adusumilli, P. S. et al. A Phase I Trial of Regional Mesothelin-Targeted CAR T-cell Therapy in Patients with Malignant Pleural Disease, in Combination with the Anti-PD-1 Agent Pembrolizumab. *Cancer Discov* 11, 2748-2763, doi:10.1158/2159-8290.CD-21-0407 (2021).
29. Tchou, J. et al. Safety and Efficacy of Intratumoral Injections of Chimeric Antigen Receptor (CAR) T Cells in Metastatic Breast Cancer. *Cancer Immunol Res* 5, 1152-1161, doi:10.1158/2326-6066.CIR-17-0189 (2017).
30. Yeku, O. O., Purdon, T. J., Koneru, M., Spriggs, D. & Brentjens, R. J. Armored CAR T cells enhance antitumor efficacy and overcome the tumor microenvironment. *Sci Rep* 7, 10541, doi:10.1038/s41598-017-10940-8 (2017).
31. Murad, J. P. et al. Effective Targeting of TAG72(+) Peritoneal Ovarian Tumors via Regional Delivery of CAR-Engineered T Cells. *Front Immunol* 9, 2268, doi:10.3389/fimmu.2018.02268 (2018).
32. Luo, H. et al. Coexpression of IL7 and CCL21 Increases Efficacy of CAR-T Cells in Solid Tumors without Requiring Preconditioned Lymphodepletion. *Clin Cancer Res* 26, 5494-5505, doi:10.1158/1078-0432.CCR-20-0777 (2020).
33. Hege, K. M. et al. Safety, tumor trafficking and immunogenicity of chimeric antigen receptor (CAR)-T cells specific for TAG-72 in colorectal cancer. *J Immunother Cancer* 5, 22, doi:10.1186/s40425-017-0222-9 (2017).
34. Yoon, S. O. et al. Construction, affinity maturation, and biological characterization of an anti-tumor-associated glycoprotein-72 humanized antibody. *J Biol Chem* 281, 6985-6992, doi:10.1074/jbc.M511165200 (2006).
35. De Pascalis, R. et al. In vitro affinity maturation of a specificity-determining region-grafted humanized anti-carcinoma antibody: isolation and characterization of minimally immunogenic high-affinity variants. *Clin Cancer Res* 9, 5521-5531 (2003).
36. Abate-Daga, D. & Davila, M. L. CAR models: next-generation CAR modifications for enhanced T-cell function. *Mol Ther Oncolytics* 3, 16014, doi:10.1038/mto.2016.14 (2016).
37. Long, A. H. et al. 4-1 BB costimulation ameliorates T cell exhaustion induced by tonic signaling of chimeric antigen receptors. *Nat Med* 21, 581-590, doi:10.1038/nm.3838 (2015).
38. Priceman, S. J. et al. Co-stimulatory signaling determines tumor antigen sensitivity and persistence of CAR T cells targeting PSCA+ metastatic prostate cancer. *Oncoimmunology* 7, e1380764, doi:10.1080/2162402X.2017.1380764 (2018).
39. Alizadeh, D. et al. IFNgamma Is Critical for CAR T Cell-Mediated Myeloid Activation and Induction of Endogenous Immunity. *Cancer Discov* 11, 2248-2265, doi:10.1158/2159-8290.CD-20-1661 (2021).
40. Jain, M. D. et al. Tumor interferon signaling and suppressive myeloid cells are associated with CAR T-cell failure in large B-cell lymphoma. *Blood* 137, 2621-2633, doi:10.1182/blood.2020007445 (2021).
41. Textor, A. et al. Efficacy of CAR T-cell therapy in large tumors relies upon stromal targeting by IFNgamma. *Cancer Res* 74, 6796-6805, doi:10.1158/0008-5472.CAN-14-0079 (2014).
42. Zhang, L. et al. Tumor-infiltrating lymphocytes genetically engineered with an inducible gene encoding interleukin-12 for the immunotherapy of metastatic melanoma. *Clin Cancer Res* 21, 2278-2288, doi:10.1158/1078-0432.CCR-14-2085 (2015).
43. Sridhar, P. & Petrocca, F. Regional Delivery of Chimeric Antigen Receptor (CAR) T-Cells for Cancer Therapy. *Cancers (Basel)* 9, doi:10.3390/cancers9070092 (2017).
44. Koneru, M., Purdon, T. J., Spriggs, D., Koneru, S. & Brentjens, R. J. IL-12 secreting tumor-targeted chimeric antigen receptor T cells eradicate ovarian tumors in vivo. *Oncoimmunology* 4, e994446, doi:10.4161/2162402X.2014.994446 (2015).
45. Henry, C. J., Ornelles, D. A., Mitchell, L. M., Brzoza-Lewis, K. L. & Hiltbold, E. M. IL-12 produced by dendritic cells augments CD8+ T cell activation through the production of the chemokines CCL1 and CCL17. *J Immunol* 181, 8576-8584, doi:10.4049/jimmunol.181.12.8576 (2008).

46 Guedan, S., Calderon, H., Posey, A. D., Jr. & Maus, M. V. Engineering and Design of Chimeric Antigen Receptors. *Mol Ther Methods Clin Dev* 12, 145-156, doi: 10.1016/j.omtm.2018.12.009 (2019).
47 Miller, I. C. et al. Enhanced intratumoural activity of CAR T cells engineered to produce immunomodulators under photothermal control. *Nat Biomed Eng* 5, 1348-1359, doi:10.1038/s41551-021-00781-2 (2021).
48 Huang, Z. et al. Engineering light-controllable CAR T cells for cancer immunotherapy. *Sci Adv* 6, eaay9209, doi:10.1126/sciadv.aay9209 (2020).
49 Prinzing, B. & Krenciute, G. Hypoxia-inducible CAR expression: An answer to the on-target/off-tumor dilemma? *Cell Rep Med* 2, 100244, doi:10.1016/j.xcrm.2021.100244 (2021).
50 Roybal, K. T. et al. Precision Tumor Recognition by T Cells With Combinatorial Antigen-Sensing Circuits. *Cell* 164, 770-779, doi:10.1016/j.cell.2016.01.011 (2016).
51 Srivastava, S. et al. Logic-Gated ROR1 Chimeric Antigen Receptor Expression Rescues T Cell-Mediated Toxicity to Normal Tissues and Enables Selective Tumor Targeting. *Cancer Cell* 35, 489-503 e488, doi:10.1016/j.ccell.2019.02.003 (2019).
52 Giordano-Attianese, G. et al. A computationally designed chimeric antigen receptor provides a small-molecule safety switch for T-cell therapy. *Nat Biotechnol* 38, 426-432, doi:10.1038/s41587-019-0403-9 (2020).
53 Zhang, L. et al. Improving adoptive T cell therapy by targeting and controlling IL-12 expression to the tumor environment. *Mol Ther* 19, 751-759, doi:10.1038/mt.2010.313 (2011).
54 Zhang, L. et al. Enhanced efficacy and limited systemic cytokine exposure with membrane-anchored interleukin-12 T-cell therapy in murine tumor models. *J Immunother Cancer* 8, doi:10.1136/jitc-2019-000210 (2020).
55 Hurton, L. V. et al. Tethered IL-15 augments antitumor activity and promotes a stemcell memory subset in tumor-specific T cells. *Proc Natl Acad Sci USA* 113, E7788-E7797, doi:10.1073/pnas.1610544113 (2016).
56 Hu, J. et al. Cell membrane-anchored and tumor-targeted IL-12 (attIL12)-T cell therapy for eliminating large and heterogeneous solid tumors. *J Immunother Cancer* 10, doi:10.1136/jitc-2021-003633 (2022).
57 Agarwal, Y. et al. Intratumourally injected alum-tethered cytokines elicit potent and safer local and systemic anti-cancer immunity. *Nat Biomed Eng* 6, 129-143, doi: 10.1038/s41551-021-00831-9 (2022).
58 Siddiqi, T. et al. CD19-directed CAR T-cell therapy for treatment of primary CNS lymphoma. *Blood Adv* 5, 4059-4063, doi:10.1182/bloodadvances.2020004106 (2021).
64 Neman, J. et al. Human breast cancer metastases to the brain display GABAergic properties in the neural niche. Proceedings of the National Academy of Sciences of the United States of America 111, 984-989, doi:10.1073/pnas.1322098111 (2014).
65 Ogawa, T. et al. ST6GALNAC1 plays important roles in enhancing cancer stem phenotypes of colorectal cancer via the Akt pathway. Oncotarget 8, 112550-112564, doi: 10.18632/oncotarget.22545 (2017).
66 Kern, P., Hussey, R. E., Spoerl, R., Reinherz, E. L. & Chang, H.-C. Expression, Purification, and Functional Analysis of Murine Ectodomain Fragments of CD8aa and CD8αβ Dimers. Journal of Biological Chemistry 274, 27237-27243, doi:10.1074/jbc.274.38.27237 (1999).
67 Classon, B. J. et al. The hinge region of the CD8 alpha chain: structure, antigenicity, and utility in expression of immunoglobulin superfamily domains. Int Immunol 4, 215-225, doi:10.1093/intimm/4.2.215 (1992).
68 Kochenderfer, J. N., Yu, Z., Frasheri, D., Restifo, N. P. & Rosenberg, S. A. Adoptive transfer of syngeneic T cells transduced with a chimeric antigen receptor that recognizes murine CD19 can eradicate lymphoma and normal B cells. Blood 116, 3875-3886, doi:10.1182/blood-2010-01-265041 (2010).
69 Park, A. K. et al. Effective combination immunotherapy using oncolytic viruses to deliver CAR targets to solid tumors. Sci Transl Med 12, doi:10.1126/scitranslmed.aaz1863 (2020).
70 Murad, J. P. et al. Pre-conditioning modifies the TME to enhance solid tumor CAR T;cell efficacy and endogenous protective immunity. Molecular Therapy, doi:10.1016/j.ymthe.2021.02.024.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid molecule comprising a nucleotide sequence encoding a polypeptide comprising the amino acid sequence of SEQ ID NO: 6 or SEQ ID NO:7.

2. The nucleic acid molecule of claim 1, wherein the nucleotide sequence encodes a polypeptide comprising the amino acid sequence of SEQ ID NO: 6.

3. The nucleic acid molecule of claim 1, wherein the nucleotide sequence encodes a polypeptide comprising the amino acid sequence of SEQ ID NO: 7.

4. The nucleic acid molecule of claim 1, wherein the polypeptide further comprises a signal sequence.

5. The nucleic acid molecule of claim 4, wherein the signal sequence comprises the amino acid sequence of SEQ ID NO: 10 or SEQ ID NO: 11.

6. The nucleic acid molecule of claim 1, wherein the polypeptide comprises the amino acid sequence of SEQ ID NO: 8 or SEQ ID NO: 9.

7. A population of human immune cells comprising the nucleic acid molecule of claim 1.

8. The population of human immune cells of claim 7, wherein the immune cells are T cells.

9. The nucleic acid molecule of claim 1, wherein the polypeptide consists of the amino acid sequence of SEQ ID NO: 6.

10. The nucleic acid molecule of claim 1, wherein polypeptide consists of the amino acid sequence of SEQ ID NO: 7.

11. The nucleic acid molecule of claim 6, wherein the polypeptide consists of the amino acid sequence of SEQ ID NO: 8.

12. The nucleic acid molecule of claim 6, wherein the polypeptide consists of the amino acid sequence of SEQ ID NO: 9.

13. A population of human immune cells comprising the nucleic acid molecule of any of claims 6 and 9-12.

14. The population of human immune cells of claim 13, wherein the immune cells are T cells.

* * * * *